US012209115B2

(12) United States Patent
Ishii et al.

(10) Patent No.: US 12,209,115 B2
(45) **Date of Patent: *Jan. 28, 2025**

(54) EXOSOME-TARGETED DNA VACCINE

(71) Applicant: EXORPHIA, INC., Tokyo (JP)

(72) Inventors: Ken Ishii, Tokyo (JP); Kouji Kobiyama, Ibaraki (JP); Tomohiro Kanuma, Ibaraki (JP)

(73) Assignee: EXORPHIA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/587,925

(22) Filed: Jan. 28, 2022

(65) Prior Publication Data

US 2022/0153810 A1 May 19, 2022

Related U.S. Application Data

(62) Division of application No. 16/091,073, filed as application No. PCT/JP2016/001900 on Apr. 4, 2016.

(51) Int. Cl.

| | |
|---|---|
| ***C07K 14/705*** | (2006.01) |
| ***A61K 31/713*** | (2006.01) |
| ***A61K 39/00*** | (2006.01) |
| ***A61K 48/00*** | (2006.01) |
| ***A61P 35/00*** | (2006.01) |
| ***C07K 14/47*** | (2006.01) |
| ***C07K 14/77*** | (2006.01) |
| ***C12N 15/09*** | (2006.01) |

(52) U.S. Cl.

CPC ...... *C07K 14/70596* (2013.01); *A61K 31/713* (2013.01); *A61K 39/00* (2013.01); *A61K 39/0011* (2013.01); *A61K 48/00* (2013.01); *A61P 35/00* (2018.01); *C07K 14/47* (2013.01); *C07K 14/77* (2013.01); *C12N 15/09* (2013.01); *A61K 2039/53* (2013.01); *A61K 2039/572* (2013.01); *A61K 2039/575* (2013.01); *A61K 2039/6031* (2013.01); *C07K 2319/00* (2013.01); *C07K 2319/43* (2013.01)

(58) Field of Classification Search

CPC .. C07K 14/70596; C07K 14/47; C07K 14/77; C07K 2319/00; C07K 2319/43; A61K 31/713; A61K 39/00; A61K 39/0011; A61K 48/00; A61K 2039/53; A61K 2039/572; A61K 2039/575; A61K 2039/6031; A61P 35/00; C12N 15/09

See application file for complete search history.

(56) References Cited

U.S. PATENT DOCUMENTS

| | | | | |
|---|---|---|---|---|
| 10,233,445 | B2 * | 3/2019 | Seow | C07K 14/705 |
| 2017/0274062 | A1 * | 9/2017 | Romero Ramos | A61K 39/02 |

FOREIGN PATENT DOCUMENTS

| | | | | |
|---|---|---|---|---|
| AU | 2000010514 A1 | | 7/2000 | |
| AU | 2004203482 A1 | * | 8/2004 | A61P 11/06 |
| JP | 2002-529074 A | | 9/2002 | |
| JP | 2015-500825 A | | 1/2015 | |
| WO | 00/28001 A1 | | 5/2000 | |
| WO | 2013/084000 A2 | | 6/2013 | |

OTHER PUBLICATIONS

Hartman, Zachary C., et al. "Increasing vaccine potency through exosome antigen targeting." Vaccine 29.50 (2011): 9361-9367 (Year: 2011).*

Kang, Tae Heung, et al. "Enhancing DNA vaccine potency by co-administration of xenogenic MHC class-I DNA." Gene therapy 17.4 (2010): 531-540 (Year: 2010).*

Pols, Maaike S., and Judith Klumperman. "Trafficking and function of the tetraspanin CD63." Experimental cell research 315.9 (2009): 1584-1592 (Year: 2009).*

Maecker (BMC immunology 4.1 (2003): 1-14) (Year: 2003).*

Hartman et al., "Increasing vaccine potency through exosome antigen targeting," *Vaccine 29*:9361-9367, 2011.

Kanuma et al., "Antigen specific CD8 T cell response by exosome targeting DNA vaccine," *The Japanese Society for Vaccinology Gakujutsu Shukai Program Shorokushu 19*:116, 2015, 4 pages.

Kanuma et al., "Exosome targeting DNA vaccination enhances antigen-specific CD8 T cell responses," Abstract 3D-W37-8-0/P, Oct. 30, 2015, 1 page.

Zeelenberg et al., "Targeting Tumor Antigens to Secreted Membrane Vesicles In vivo Induces Efficient Antitumor Immune Responses," *Cancer Res 68*(4):1228-1235, 2008.

Kalluri et al., "The biology, function, and biomedical applications of exosomes," *Science 367*: eaau6977, Feb. 2020.

* cited by examiner

*Primary Examiner* — Nancy J Leith
*Assistant Examiner* — Kyle T Rega
(74) *Attorney, Agent, or Firm* — Seed IP Law Group LLP

(57) ABSTRACT

In order to further increase antigenicity to provide a DNA vaccine which is clinically usable in humans, the inventors of the present invention focused on exosomes, which are garnering attention as tools for DDS, and discovered that an exosome expressing a fusion antigen of an exosome (extracellular microparticle)-constituent protein and a vaccine antigen has excellent cytotoxic T-cell inducibility. Consequently, the present invention provides a nucleic acid constituent including a nucleic acid sequence coding for an exosome marker protein and a nucleic acid sequence coding for a vaccine antigen.

11 Claims, 25 Drawing Sheets

Specification includes a Sequence Listing.

pCD63-OVA

Empty Vector

Total IgG
IgG1
IgG2c
**
**
**
Anti-OVA titer (10n)
5
4
3
2
1
OVA
CD63-OVA
Cal-OVA
OVA protein
NC Total IgG
IgG1
IgG2c
Anti-OVA titer (10ⁿ)
6
5
4
3
2
IgG2c/IgG1 (ratio)
20
15
10
5
0
**
NS
*
pCD63
pOVA
pCD63-OVA a
b
c
d
IFN-γ (ng/ml)
25
20
15
10
5
0
***
***
**
a b c d
a b c d
pCal-OVA
pCD63-OVA p = 0.0079
p = 0.0079
NS
Tetramer+CD8+ T cells/CD8+ T cells (%)
0
1
2
3
4
5
Empty vector
pOVA
pCD63-OVA PBS
100nm beads
200nm beads
SSC
FSC
CD63-OVA-EGFP
Empty vector
SSC
EGFP
SSC
FSC

EXOSOME-TARGETED DNA VACCINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690188_408D1_SEQUENCE_LISTING.txt. The text file is 63200 B, was created on Jan. 24, 2022, and is being submitted electronically via EFS-Web.

TECHNICAL FIELD

The present invention relates to a novel DNA vaccine. More specifically, the present invention relates to an exosome targeting DNA vaccine and a technology of a novel DNA vaccine with excellent ability to induce cytotoxic T cells for expressing a fusion antigen of an exosome (extracellular microparticle) constituting protein and a vaccine antigen.

BACKGROUND ART

DNA vaccines were developed about 20 years ago, but they still have not been in clinical use on humans. The reasons therefor include: expected immunogenicity cannot be attained; risk of integration into the genome and the associated risk of oncogenesis; risk of inducing an autoimmune disease against the genome after administration of a DNA vaccine; and risk of acquiring drug resistance after administrating a DNA vaccine with a plasmid to which a sequence of an antibiotics is incorporated. Improvement of DNA vaccines is ongoing worldwide.

Non Patent Literature 1 discloses that an antigen is encapsulated into an exosome and the exosome is administered to a mouse to induce a Th1-type T cell response.

Patent Literature 1 discloses a technology related to a complex comprising an exosome and drug delivery.

Non Patent Literature 2 discloses that virus like particles (extracellular microparticles) are released from cells after administration of a DNA vaccine with a plasmid, in which an antigen (OVA) is fused with an HIV-1 Gag protein.

CITATION LIST

Patent Literature

[PTL 1] International Publication No. WO 2014054588 A1

Non Patent Literature

[NPL 1] Blood, 19 Mar. 2009, vol. 113, num. 12, 2673-2683.

[NPL 2] Journal of Extracellular Vesicles, 2014, 3: 24646.

SUMMARY OF INVENTION

Solution to Problem

In order to provide a DNA vaccine that can be used clinically on humans and to further enhance antigenicity, the inventors focused on exosomes, which have drawn attention as a tool for DDS, to find that such a DNA vaccine has excellent ability to induce cytotoxic T cells inducing capability for expressing a fusion antigen of an exosome (extracellular microparticle) constituting protein and a vaccine antigen.

Specifically, a plasmid DNA that expresses an antigen made by fusing an antigen (OVA: ovalbumin) and CD63, which is a tetraspanin family protein that is commonly known and used as a marker for exosomes, was prepared. When a mouse was immunized with this plasmid DNA, enhancement in T cell responses was observed in a DNA vaccine administration group expressing a fusion antigen of CD63, relative to a DNA vaccine administration group expressing OVA alone. An increase in the antigen specific CTL (cytotoxic T cells) count was also observed. Furthermore, tumor cells expressing OVA were transplanted into a mouse, and the prepared plasmid DNA was administered once after 7 days from the transplantation. As a result, tumor growth was significantly suppressed compared to an expression vector administration group. In view of the above, a DNA vaccine expressing a fusion antigen of an exosome marker protein CD63 and a vaccine antigen was found to be useful as a novel prophylactic/therapeutic technology that enhances the ability to induce antigen specific CTLs.

(1) A nucleic acid construct comprising a nucleic acid sequence encoding an exosome marker protein and a nucleic acid sequence encoding a vaccine antigen.

(2) The nucleic acid construct of item 1, wherein the exosome marker protein is a protein that is present in a membrane of an exosome.

(3) The nucleic acid construct of item 1 or 2, wherein the exosome marker protein belongs to the tetraspanin family.

(4) The nucleic acid construct of any one of items 1 to 3, wherein the exosome marker protein is selected from the group consisting of CD63, CD81, CD9, CD31, HLA-G, TSG101, Rab5b, and ALIX.

(5) The nucleic acid construct of any one of items 1 to 4, wherein the exosome marker protein is selected from the group consisting of CD63, CD81, and CD9.

(6) The nucleic acid construct of any one of items 1 to 5, wherein the antigen is selected from a cancer antigen and a viral antigen.

(7) The nucleic acid construct of any one of items 1 to 6, which is a plasmid DNA.

(8) A DNA vaccine comprising the nucleic acid construct of any one of items 1 to 7.

(9) The DNA vaccine of item 8 for improving Th1-type immunity induction.

(10) The DNA vaccine of item 8 or 9, characterized in targeting cancer or a viral disease.

(11) A protein in a form of a vaccine antigen protein fused with an exosome marker protein.

(11A) The protein of item 11, further comprising one or more features of the preceding items.

(12) An exosome comprising a vaccine antigen protein and an exosome marker protein in a fused form.

(12A) The exosome of item 12, further comprising one or more features of the preceding items.

(13) An immune response enhancer comprising the nucleic acid construct of any one of items 1 to 7, the DNA vaccine of items 8 to 10, the protein of item 11 or 11A, or the exosome of item 12 or 12A.

(14) A composition for enhancing a T cell response comprising the nucleic acid construct of any one of items 1 to 7, the DNA vaccine of items 8 to 10, the protein of item 11 or 11A, or the exosome of item 12 or 12A.

(15) A cytotoxic agent comprising the nucleic acid construct of any one of items 1 to 7, the DNA vaccine of items 8 to 10, the protein of item 11 or 11A, or the exosome of item 12 or 12A.

(16) A medicament comprising the nucleic acid construct of any one of items 1 to 7, the DNA vaccine of items 8 to 10, the protein of item 11 or 11A, or the exosome of item 12 or 12A.

(17) A medicament for treating or preventing cancer comprising the nucleic acid construct of any one of items 1 to 9, the DNA vaccine of items 10, the protein of item 11 or 11A, or the exosome of item 12 or 12A.

(18) A method of enhancing an immune response in a subject, comprising administering to the subject an effective amount of the nucleic acid construct of any one of items 1 to 7, the DNA vaccine of items 8 to 10, the protein of item 11 or 11A, or the exosome of item 12 or 12A.

(19) A method of enhancing a T cell response, comprising administering to a subject an effective amount of the nucleic acid construct of any one of items 1 to 7, the DNA vaccine of items 8 to 10, the protein of item 11 or 11A, or the exosome of item 12 or 12A.

(20) A method of treating or preventing cancer, comprising administering to a subject an effective amount of the nucleic acid construct of any one of items 1 to 7, the DNA vaccine of items 8 to 10, the protein of item 11 or 11A, or the exosome of item 12 or 12A.

(21) A composition for improving immunogenicity of a vaccine DNA, comprising a nucleic acid sequence encoding an exosome marker protein.

(22) The composition of item 21, wherein the exosome marker protein is a protein that is present in a membrane of an exosome.

(23) The composition of item 21 or 22, wherein the exosome marker protein belongs to the tetraspanin family.

(24) The composition of any one of items 21 to 23, wherein the exosome marker protein is selected from the group consisting of CD63, CD81, CD9, CD31, HLA-G, TSG101, Rab5b, and ALIX.

(25) The composition of any one of items 21 to 24, wherein the exosome marker protein is selected from the group consisting of CD63, CD81, and CD9.

(26) The composition of any one of items 21 to 25, wherein an antigen contained in the vaccine DNA is selected from a cancer antigen and a viral antigen.

(27) The composition of any one of items 21 to 26, wherein the vaccine DNA is a plasmid DNA.

(27A) The composition of any one of items 21 to 27, further comprising one or more features of items 1 to 11, 11A, 12, 12A, and 13 to 20.

The present invention is intended so that one or more of the above features can be provided as the explicitly disclosed combinations as well as other combinations thereof. Additional embodiments and advantages of the present invention are recognized by those skilled in the art by reading and understanding the following detailed explanation, as needed.

Advantageous Effects of Invention

The present invention achieves an effect of providing a clinically-applicable DNA vaccine, which was not previously attainable. For example, administration of the DNA vaccine of the invention induces a strong antigen specific T cell response such as an antigen specific $CD8^+$ T cell response, which is stronger than administration of a conventional antigen-containing exosome itself. Further, stronger cytotoxic activity is observed from administration of the DNA vaccine of the invention. A high therapeutic effect on tumor is also observed from administration of the DNA vaccine of the invention. It has been elucidated from the above that the immunogenicity of a DNA vaccine can be improved by targeting an antigen of a DNA vaccine to an exosome.

The present invention shows that expression of IgG2(c) increases more than IgG1 by using a protein of the tetraspanin family, and Th1-type immune responses, i.e., cellular immunity (especially $CD8^+$ T cell responses) are enhanced for a DNA vaccine, as shown in the Examples.

The result achieved by the present invention shows that a clinically applicable DNA vaccine, which can strongly induce an antigen specific $CD8^+$ T cell, can be provided by targeting an antigen of the DNA vaccine to an exosome. As demonstrated in the Examples, immunization with a purified OVA-containing exosome can elicit induction of OVA-specific $CD4^+$ and $CD8^+$ T cells in naïve mice. Meanwhile, this was not elicited by immunization with an exosome purified from cells transfected with a control plasmid encoding a calnexin-OVA fusion protein targeting vesicles or only OVA proteins. Vaccination of a mouse with pCD63-OVA induced a potent antigen specific T cell response, especially $CD8^+$ T cell response. In addition, exosome targeting with CD63 resulted in a better $CD8^+$ T cell response than ER targeting with calnexin. As demonstrated in the Examples, vaccination with exosome targeting DNA significantly inhibited tumor growth compared to control DNA vaccine inoculation when the inventors used a mouse tumor transplantation model for evaluating pCD63-OVA as a therapeutic vaccine. The results of the present invention show that antigen targeting to an exosome with DNA vaccine inoculation can be a tool for eliciting a potent $CD8^+$ T cell response to an encoded antigen and can be useful as a cancer vaccine. The same effect with CD63 was also confirmed for tetraspanins CD9 and CD81.

The present invention can be advantageous in terms of better actual immunization method or the like. Although not wishing to be bound by any theory, DNA vaccines are more advantageous than the exosome itself because autologous (e.g., patients' own) exosome may need to be collected and administered in clinical practice, but MHC class I or class II is expressed.

The present invention, in a form of a DNA vaccine, can be readily prepared and administered to basically anyone, which is one of the advantages over single exosome administration. Furthermore, the effect attained by the present invention is higher than the level that can be achieved by conventional art in view of the amount of DNA plasmid used or the like. Further, manufacture of an antigen containing exosome was in itself difficult with conventional methods when manufacturing exosomes, but one of the advantages of the present invention is that an antigen can be readily expressed in an exosome by using a DNA plasmid (vaccine). In this manner, this is superior to administration of exosome itself with respect to various points. Other notably advantages include when an autologous cell is used, an antigen can be readily expressed in an exosome with a DNA vaccine and this can be readily administered as a DNA vaccine, so that a different approach can be used and the applicable scope is broadened.

Since IgG2c increases and IgG1 decreases, this proves that cell-mediated immune response (Th1) is proven to be significant. Thus, it is understood that the present invention can be more advantageously used in treating an infection, cancer, or the like requiring induction of a Th1-type immune response.

DESCRIPTION OF EMBODIMENTS

Figure 1A:
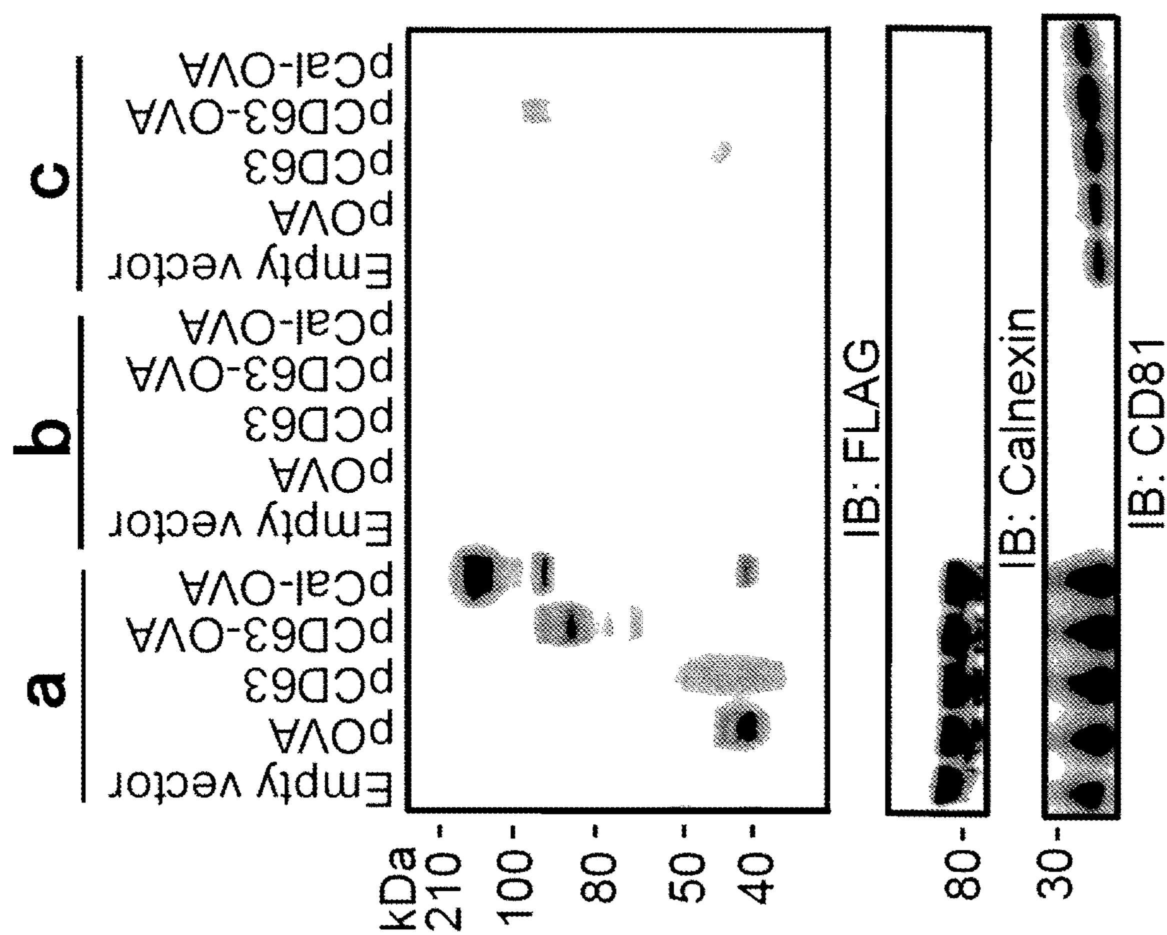
FIG. 1A Evaluation of antigen expressing exosomes as a CTL inducing immunogen. (A, B) An empty vector, pOVA, pCD63, pCD63-OVA, or pCal-OVA was transiently transfected into 293-F cells and 293T cells. After 48 hours from transfection, the supernatant was separated from the cells, and the exosome fraction was purified. (A) The cell, supernatant, and exosome fractions were analyzed by immunoblotting. (B) ELISA was used on the cells and supernatant to analyze the OVA protein concentration. The error bar represents the SD. The labels a, b, and c indicate cell, supernatant, and exosome fractions, respectively.

The present invention is explained hereinafter while describing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definitions of the terms and/or the basic technical content that are particularly used herein are explained hereinafter as appropriate.

As used herein, "vaccine" refers to a substance which comprises or encodes an antigen that does not induce a disease, but provides active immunity against a substance comprising an antigen. As used herein, "DNA vaccine" refers to a nucleic acid encoding a vaccine antigen. Such a common name is used because DNA (especially plasmid DNA) is mainly used. It is understood that an embodiment using a nucleic acid includes an embodiment of a vaccine incorporating a viral vector or the like which is delivered into the body, in which case a vaccine can also be provided in a nucleic acid form other than DNA. In such a case, the vaccine is also called a "nucleic acid vaccine". DNA vaccines are generally in a form of a plasmid DNA. Meanwhile, if a DNA vaccine is subcutaneously administered in a form of a plasmid DNA, the plasmid DNA is incorporated into a subcutaneous cell and produces an antigen protein of interest in the cell.

DNA vaccine inoculation can be a prophylactic and/or therapeutic method for a human disease, which can be applied to not only infectious diseases but also on non-transmittable diseases. The clinical benefit of a DNA vaccine is the low cost, stability and high level of producibility, and the ease of modification of the antigen sequence thereof to be effective against a highly mutated pathogen. In the field of veterinary medicine, DNA vaccines are already approved for West Niles viruses in horses, infectious hematopoietic necrosis viruses in salmons, and melanoma in dogs. The results of early stage clinical trials in humans indicate that a DNA vaccine is safe and well tolerated, but the immunogenicity of a DNA vaccine is much lower than expected based on the results of animal experiments. For example, this has not been able to be solved by a change in use of a promotor or codon in an antigen sequence, insertion of a genetic adjuvant, addition of a boost vaccination, mixing of a vaccine with an external adjuvant, administration of a vaccine through improvement in the pathway or device, or the like.

"Plasmid DNA" is used in the meaning that is commonly used in the art. "Plasmid DNA" refers to a DNA molecule that is present outside the nucleus of bacteria such as *E. coli* or yeast and is inherited by a daughter cell through cell division. Since a plasmid DNA generally has a cyclic double stranded structure and replicates independently from a DNA of a chromosome, a plasmid DNA can be used as a vector in order to introduce a gene. Plasmids include those that play various roles, such as those with a gene of a protein exhibiting resistance to a drug and those that transform other bacteria by inducing cell conjugation called F plasmid. Plasmids can be appropriately selected and utilized in accordance with the objective in the present invention.

As used herein, "nucleic acid construct" refers to a construct comprising a nucleic acid. Nucleic acid constructs include those that are simple nucleic acid fragments as well as those in a form of a plasmid DNA, those with a function of a DNA vaccine, and the like.

As used herein, "antigen" (also referred to as Ag) refers to any substrate that can be specifically bound by an antibody molecule. As used herein, "immunogen" refers to an antigen that can initiate lymphocyte activation which leads to an antigen specific immune response. As used herein, "epitope" or "antigen determinant" refers to a site in an antigen molecule to which an antibody or a lymphocyte receptor binds. A method of determining an epitope is well known in the art. Such an epitope can be determined by those skilled in the art by using a well-known and conventional technique when a primary sequence of an amino acid or a nucleic acid is provided. It is understood that not only the specific antibodies in the Examples, but also antibodies having different sequences can be similarly used as the antibody of the invention, as long as the epitope is the same.

As used herein, "vaccine antigen" refers to an antigen with an ability to induce a response from the immune system when administered to a human or an animal. Such a response from the immune system can induce production of antibodies or activation of a certain type of cells (particularly antigen presenting cells (e.g., dendritic cells), T lymphocytes, or B lymphocytes). In the present invention, examples thereof include, but are not limited to, cancer antigens for therapy targeting cancer. For example, an ovalbumin can be used as a model vaccine antigen.

Anticancer activity can be tested with a test on a model animal. Such a test can be conducted by referring to Onishi M. et al., J Immunol 194: 2673-2682, or the like. CTL activity or the like can be tested by referring to Kobiyama K. et al., Proc Natl Acad Sci USA 111: 3086-3091. As used herein, "vaccine antigen" may be called a "vaccine antigen protein" when referring to only proteins.

"Exosome" is used in the meaning that is commonly used in the art. An exosome is a membrane vesicle that is secreted in a cell with a diameter of generally 30 nm to 150 nm and preferably about 30 to 100 nm. An exosome is a multiprotein complex which degrades various RNAs and is secreted from all types of cells through fusion with a plasma membrane of a multivesicular body. Exosomes are present in various bodily fluids such as the plasma, breast milk, semen, saliva, and urine. Interestingly, many of DNA, RNA, miRNA, protein, and lipids are contained inside an exosome. These vesicles were shown to mediate cell-cell communication and to be closely associated with immunomodulation (Poutsiaka, D. D., D. D. Taylor, E. M. Levy, and P. H. Black. 1985. J Immunol 134: 145-150.) Both MHC class I and II and APC expressing a costimulation molecule that stimulates $CD4^+$ and $CD8^+$ T cells secret exosomes (Robbins, P. D., and A. E. Morelli. 2014. Nat Rev Immunol 14: 195-208, Bobrie, A., M. Colombo, G. Raposo, and C. Thery. 2011. Traffic 12: 1659-1668). In addition, mature dendritic cell (DC) derived exosomes can activate immature dendritic cells and improve the antigen presenting capability thereof (Montecalvo, A., et al., 2012. Blood 119: 756-766.) An antigen containing exosome can also be used as a vaccine for cancer therapy (Raposo, G., et al., 1996. J Exp Med 183: 1161-1172.) However, use of an exosome as a material for DNA vaccines is not suggested.

Tetraspanin family proteins are known as a surface marker of an exosome. While lipids are the main component of exosomes, exosomes comprise various proteins, lipids, and RNA (including miRNA). They are understood to induce a functional or physiological change by being transported to another cell. As used herein, a naturally-occurring exosome expressing the DNA vaccine of the invention is typically used, but an exosome may be further modified. It is understood that such a modification can be any modification, as long as the exosome can be used as a DNA vaccine. It is suggested that exosomes play a role in mediation of an adaptive immune response to infection pathogens or tumor, tissue repair, neurotransmission, transport of pathogenic proteins, and the like. Detailed descriptions can be found by referring to for example Trends Mol Med. 2015 Jul. 28. pii: S1471-49 14(15)00137-9, whose content is incorporated herein by reference.

As used herein, "exosome marker protein" refers to any protein contained in an exosome. Examples of such a protein include tetraspanin family proteins (e.g., CD9, CD63, CD81, and the like), Alix, Tsg101, Hsp70, other heat shock proteins, and the like (see for example Trends Mol Med. 2015 Jul. 28. pii: S1471-1491 4(15)00137-9. (Trends Mol Med. Volume 21, Issue 9, September 2015, Pages 533-542); J. Cell Biol. Vol. 200 No. 4, 373-383, and the like).

As used herein, "tetraspanin family" is a membrane protein family with a structure that penetrates the cell membrane four times. In humans, at least 33 types of members such as CD9, CD63, CD81, CD82, and CD151 are known. In summary, the function of tetraspanin is formation of a complex by binding to another membrane protein. For this reason, this is also called a molecular facilitator or molecular organizer. In the present invention, the same effect as CD63 is also confirmed in the Examples for tetraspanins CD9 and CD81. Thus, it is understood that any tetraspanin family protein can be advantageously used in a DNA vaccine.

CD63 is a member of the tetraspanin family. CD63 is also called LAMP-3, ME491, MLA1, OMA81H, or TSPAN30. The nucleic acid sequence and amino acid sequence of human CD63 are disclosed in NCBI accession numbers NM_001040034 (SEQ ID NO: 1) and NP_001244318 (SEQ ID NO: 2), respectively, and the nucleic acid sequence and the amino acid sequence of mice are disclosed in NM_001042580 (SEQ ID NO: 3) and NP_001036045 (SEQ ID NO: 4), respectively, which are also incorporated herein by reference. CD63 can be identified by the accession number OMIM: 155740 HomoloGene: 375267. When used for the purpose herein, it is understood that "CD63" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

CD9 is a member of the tetraspanin family. CD9 is also called BTCC-1, DRAP-27, MIC3, MRP-1, TSPAN-29, or TSPAN29. The nucleic acid sequence and amino acid sequence of human CD9 are disclosed in NCBI accession numbers NM_001769 (SEQ ID NO: 5) and NP_001760 (SEQ ID NO: 6), respectively, and the nucleic acid sequence and the amino acid sequence of mice are disclosed in NM_007657 (SEQ ID NO: 7) and NP_031683 (SEQ ID NO: 8), respectively, which are also incorporated herein by reference. CD9 can be identified by the accession number OMIM: 143030 MGI: 88348 HomoloGene: 20420 GeneCards: CD9 Gene. When used for the purpose herein, it is understood that "CD9" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

CD81 is a member of the tetraspanin family. CD81 is also called CVID6, S5.7, TAPA1, or TSPAN28. The nucleic acid sequence and amino acid sequence of human CD81 are disclosed in NCBI accession numbers NM_001297649 (SEQ ID NO: 9) and NP_001284578 (SEQ ID NO: 10), respectively, and the nucleic acid sequence and the amino acid sequence of mice are disclosed in NM_133655 (SEQ ID NO: 11) and NP_598416 (SEQ ID NO: 12), respectively, which are also incorporated herein by reference. CD81 can be identified by the accession number OMIM: 186845 MGI: 1096398 HomoloGene: 20915 ChEMBL: 1075180 GeneCards: CD81 Gene. When used for the purpose herein, it is understood that "CD81" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

The same applies to all other proteins mentioned in the present invention. Therefore, the established name of a protein or nucleic acid not only refers to a protein or nucleic acid explicitly disclosed herein, but also functionally active derivatives, functionally active fragments thereof, homologs thereof, and mutants encoded by a nucleic acid that hybridizes with a nucleic acid encoding the protein under conditions with high or low stringency, preferably the aforementioned conditions. As used herein, "derivative", "analog of a constituent protein", or "mutant" preferably includes, without intending to be limiting, molecules comprising a substantially homologous region in a constituent protein. In various embodiments, such a molecule is at least 30%, 40%, 50%, 60%, 70%, 80%, 90%, 95%, or 99% identical compared to an amino acid sequence of the same size or a sequence aligned by a computer homology program known in the art, or a nucleic acid encoding such a molecule can hybridize with a sequence encoding a constituent protein under stringent conditions, moderately stringent conditions, or non-stringent conditions. This is a result of modifying a naturally-occurring protein by an amino acid substitution, deletion, and addition, and refers to a protein whose derivative still exhibits, although not necessarily to the same degree, the biological function of the naturally-occurring protein. For example, the biological function of such a protein can be found by a suitable and available in vitro assay that is described herein or known in the art.

As used herein, "functionally active" refers to a polypeptide, a fragment, or a derivative having a structural function, regulating function, or biochemical function of a protein such as biological activity in accordance with the embodiment associated with the polypeptide, fragment or derivative of the invention. In the present invention, a fragment of an exosome marker protein or a protein belonging to the tetraspanin family is a polypeptide comprising any region of the exosome marker protein or the protein belonging to the tetraspanin family, which does not need to have the biological function of naturally-occurring exosome marker protein or a protein belonging to the tetraspanin family as long as the objective of the present invention can be attained.

A typical nucleotide sequence of CD63 can be:

(a) a polynucleotide having the base sequence set forth in SEQ ID NO: 1 or 3 or a fragment sequence thereof;
(b) a polynucleotide encoding a polypeptide consisting of the amino acid sequence set forth in SEQ ID NO: 2 or 4 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 2 or 4, wherein the variant polypeptide has biological activity;
(d) a polynucleotide, which is a splice mutant or allelic mutant of the base sequence set forth in SEQ ID NO: 1 or 3, or a fragment thereof;
(e) a polynucleotide encoding a species homolog of a polypeptide consisting of the amino acid sequence set forth in SEQ ID NO: 2 or 4 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD63.

The amino acid sequence of CD63 can be:

(a) a polypeptide consisting of the amino acid sequence set forth in SEQ ID NO: 2 or 4 or a fragment thereof;
(b) a polypeptide having one or more amino acids with a mutation selected from the group consisting of substitution, addition, and deletion in the amino acid sequence set forth in SEQ ID NO: 2 or 4, and having biological activity;
(c) a polypeptide encoded by a splice mutant or allelic mutant of the base sequence set forth in SEQ ID NO: 1 or 3;
(d) a polypeptide, which is a species homolog of the amino acid sequence set forth in SEQ ID NO: 2 or 4; or
(e) a polypeptide having an amino acid sequence with at least 70% identity to one of the polypeptides of (a) to (d) and having biological activity.

In this regard, biological activity typically refers to the activity of CD63.

A typical nucleotide sequence of CD9 can be:

(a) a polynucleotide having the base sequence set forth in SEQ ID NO: 5 or 7 or a fragment sequence thereof;
(b) a polynucleotide encoding a polypeptide consisting of the amino acid sequence set forth in SEQ ID NO: 6 or 8 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 6 or 8, wherein the variant polypeptide has biological activity;
(d) a polynucleotide, which is a splice mutant or allelic mutant of the base sequence set forth in SEQ ID NO: 5 or 7, or a fragment thereof;
(e) a polynucleotide encoding a species homolog of a polypeptide consisting of the amino acid sequence set forth in SEQ ID NO: 6 or 8 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD9.

The amino acid sequence of CD9 can be:

(a) a polypeptide consisting of the amino acid sequence set forth in SEQ ID NO: 6 or 8 or a fragment thereof;
(b) a polypeptide having one or more amino acids with a mutation selected from the group consisting of substitution, addition, and deletion in the amino acid sequence set forth in SEQ ID NO: 6 or 8, and having biological activity;
(c) a polypeptide encoded by a splice mutant or allelic mutant of the base sequence set forth in SEQ ID NO: 5 or 7;
(d) a polypeptide, which is a species homolog of the amino acid sequence set forth in SEQ ID NO: 6 or 8; or
(e) a polypeptide having an amino acid sequence with at least 70% identity to one of the polypeptides of (a) to (d) and having biological activity.

In this regard, biological activity typically refers to the activity of CD9.

A typical nucleotide sequence of CD81 can be:

(a) a polynucleotide having the base sequence set forth in SEQ ID NO: 9 or 11 or a fragment sequence thereof;
(b) a polynucleotide encoding a polypeptide consisting of the amino acid sequence set forth in SEQ ID NO: 10 or 12 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 10 or 12, wherein the variant polypeptide has biological activity;
(d) a polynucleotide, which is a splice mutant or allelic mutant of the base sequence set forth in SEQ ID NO: 9 or 11, or a fragment thereof;
(e) a polynucleotide encoding a species homolog of a polypeptide consisting of the amino acid sequence set forth in SEQ ID NO: 10 or 12 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD81.

The amino acid sequence of CD81 can be:

(a) a polypeptide consisting of the amino acid sequence set forth in SEQ ID NO: 10 or 12 or a fragment thereof;
(b) a polypeptide having one or more amino acids with a mutation selected from the group consisting of substitution, addition, and deletion in the amino acid sequence set forth in SEQ ID NO: 10 or 12, and having biological activity;
(c) a polypeptide encoded by a splice mutant or allelic mutant of the base sequence set forth in SEQ ID NO: 9 or 11;
(d) a polypeptide, which is a species homolog of the amino acid sequence set forth in SEQ ID NO: 10 or 12; or
(e) a polypeptide having an amino acid sequence with at least 70% identity to one of the polypeptides of (a) to (d) and having biological activity.

In this regard, biological activity typically refers to the activity of CD81.

Each of them can be identified using an approach that is known in the art. Examples of references that can be referred for such an approach include references that are mentioned elsewhere herein and the like.

As used herein, “protein”, “polypeptide”, “oligopeptide” and “peptide” are used in the same meaning, referring to a polymer of amino acids of any length. Such a polymer may be linear, branched, or cyclic. Amino acids may be naturally-occurring, non-naturally occurring, or altered amino acids. These terms may also encompass those assembled into a complex of multiple polypeptide chains. These term also encompass naturally or artificially-altered amino acid polymers. Examples of such an alteration include disulfide bond formation, glycosylation, lipidation, acetylation, phosphorylation, and any other manipulation or alteration (e.g., conjugation with a label component). This definition also encompasses, for example, polypeptides comprising one or more analogs of amino acids (e.g., including non-naturally-occurring amino acids or the like), peptide-like compounds (e.g., peptoid), and other alterations known in the art. As use herein, “amino acid” may be naturally occurring or non-naturally occurring, as long as the objective of the present invention is met.

As used herein, “polynucleotide”, “oligonucleotide”, and “nucleic acid” are used in the same meaning, referring to a polymer of nucleotides of any length. These terms also encompass “oligonucleotide derivative” and “polynucleotide derivative”. The “oligonucleotide derivative” and “polynucleotide derivative” are interchangeably used and refer to an oligonucleotide or polynucleotide which comprises a derivative of a nucleotide or an oligonucleotide or polynucleotide with a bond between nucleotides that is different from normal bonds. It is understood that these derivatives or the like can be any derivative or the like, as long as they can be used as a DNA vaccine. Specific examples of such oligonucleotides include: 2'-O-methyl-ribonucleotide; oligonucleotide derivatives with a phosphodiester bond in an oligonucleotide converted into phosphorothioate bond; oligonucleotide derivatives with a phosphodiester bond in an oligonucleotide converted into an N3'-P5' phosphoramidate bond; oligonucleotide derivatives with a ribose and a phosphodiester bond in an oligonucleotide converted into a peptide nucleic acid bond; oligonucleotide derivatives with a uracil in an oligonucleotide substituted with a C-5 propynyl uracil; oligonucleotide derivatives with uracil in an oligonucleotide substituted with a C-5 thiazole uracil; oligonucleotide derivatives with a cytosine in an oligonucleotide substituted with a C-5 propynyl cytosine; oligonucleotide derivatives with a cytosine in an oligonucleotide substituted with a phenoxazine-modified cytosine; oligonucleotide derivatives with a ribose in DNA substituted with a 2'-O-propylribose; oligonucleotide derivatives with a ribose in an oligonucleotide substituted with a 2'-methoxyethoxy ribose, and the like. Unless noted otherwise, specific nucleic acid sequences are intended to encompass sequences that are explicitly set forth, as well as their conservatively altered variants (e.g., degenerate codon substitutes) and complementary sequences. Specifically, a degenerate codon substitute can be achieved by making a sequence in which the third position of one or more selected (or all) codons is substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). As used herein, “nucleic acid” is also interchangeably used with gene, cDNA, mRNA, oligonucleotide, and polynucleotide. As used herein, “nucleotide” may be naturally occurring or non-naturally-occurring.

As used herein, “gene” refers to an agent that defines a genetic trait. A “gene” may refer to a “polynucleotide”, “oligonucleotide”, or “nucleic acid”.

As used herein, “homology” of genes refers to identity of two or more genetic sequences with respect to one another, and having “homology” generally refers to having a high degree of identity or similarity. Therefore, the identity or similarity of sequences is higher when homology of two genes is high. Whether two types of genes have homology can be found by direction comparison of sequences or by a hybridization method under stringent conditions for nucleic acids. When two genetic sequences are directly compared, the genes are homologous when DNA sequences are typically at least 50% identical, preferably at least 70% identical, and more preferably at least 80%, 90%, 95%, 96%, 97%, 98%, or 99% identical between the genetic sequences. Thus, as used herein, “homolog” or “homologous gene product” refers to a protein in another species, preferably mammal, exerting the same biological function as a protein constituent of a complex which will be further described herein. Such a homolog is also called "ortholog gene product". It is understood that such a homolog, homologous gene product, ortholog gene product or the like can also be used, as long as they are in alignment with the objective of the invention.

Amino acids may be mentioned herein by either their commonly known three letter symbols or their one character symbols recommended by the IUPAC-IUB Biochemical Nomenclature Commission. Similarly, nucleotides may be mentioned by their commonly recognized one character codes. Comparison of similarity, identity and homology of an amino acid sequence and a base sequence is calculated herein by using a default parameter using a sequence analysis tool, BLAST. For example, identity can be searched using BLAST 2.2.28 (published on Apr. 2, 2013) of the NCBI. Herein, values for identity generally refer to a value obtained when aligned under the default conditions using BLAST. However, when a higher value is obtained by changing a parameter, the highest value is considered the value of identity. When identity is evaluated in a plurality of regions, the highest value thereamong is considered the value of identity. Similarity is a value calculated by taking into consideration a similar amino acid in addition to identity.

In one embodiment of the present invention, "several" may be, for example, 10, 8, 6, 5, 4, 3 or 2, or a value less than any one of the values. It is known that a polypeptide with one or several amino acid residue deletions, additions, insertions, or substitutions by other amino acids maintains its biological activity (Mark et al., Proc Natl Acad Sci USA. 1984 September; 81(18): 5662-5666., Zoller et al., Nucleic Acids Res. 1982 Oct. 25; 10(20): 6487-6500., Wang et al., Science. 1984 Jun. 29; 224 (4656): 1431-1433.) An antibody with a deletion or the like can be made, for example, by site-directed mutagenesis, random mutagenesis, biopanning using an antibody phage library, or the like. For example, KOD-Plus-Mutagenesis Kit (TOYOBO CO., LTD.) can be used for site-directed mutagenesis. An antibody with the same activity as the wild-type can be selected from mutant antibodies introduced with a deletion or the like by performing various characterizations such as FACS analysis and ELISA.

In one embodiment of the present invention, "90% or greater" may be, for example, 90, 95, 96, 97, 98, 99 or 100% or greater or within the range of any two such values. For the "homology", the percentage of the number of homologous amino acids in two or a plurality of amino acid sequences may be calculated in accordance with a known method in the art. Before calculating the percentage, amino acid sequences in a group of amino acid sequences to be compared are aligned. A space is introduced in a portion of amino acid sequences when necessary to maximize the percentage of the same amino acids. An alignment method, method of calculating the percentage, comparison method, and computer programs associated therewith have been well known in the art (e.g., BLAST, GENETYX, and the like). As used herein, "homology" can be represented by a value measured with BLAST of the NCBI, unless specifically noted otherwise. Blastp can be used in the default setting for an algorithm for comparing amino acid sequences with BLAST. Results of measurement are expressed in a numerical form as Positives or Identities.

As used herein, "polynucleotide which hybridizes under a stringent condition" refers to commonly used, well-known conditions in the art. Such a polynucleotide can be obtained by using a method such as colony hybridization, plaque hybridization, or southern blot hybridization while using a polynucleotide selected from the polynucleotides of the inventions as a probe. Specifically, the polynucleotide refers to a polynucleotide that can be identified by using a filter with immobilized DNA from a colony or plaque and performing hybridization at 65° C. in the presence of 0.7 to 1.0 M NaCl and then using an SSC (saline-sodium citrate) solution with 0.1 to 2 times concentration (composition of an SSC solution with 1 time concentration is 150 mM sodium chloride and 15 mM sodium citrate) to wash the filter under the condition of 65° C. For "stringent condition", the following are examples of conditions that can be used. (1) low ionic strength and a high temperature are used for washing (e.g., 0.015 M sodium chloride/0.0015 M sodium citrate/0.1% sodium dodecyl sulfate at 50° C.), (2) a denaturing agent such as formamide is used in hybridization (e.g., 50% (v/v) formamide, 0.1% bovine serum albumin/0.1% ficoll/0.1% polyvinyl pyrrolidone/50 mM sodium phosphate buffer with a pH of 6.5, 750 mM sodium chloride, and 75 mM sodium citrate at 42° C.), or (3) a solution comprising 20% formamide, 5×SSC, 50 mM sodium phosphate (pH 7.6), 5×Denhardt's solution, 10% dextran sulfate, and 20 mg/ml denatured sheared salmon sperm DNA, is incubated overnight at 37° C. and then a filter is washed with 1×SSC at about 37 to 50° C. The formamide concentration may be 50% or greater. Washing time may be 5, 15, 30, 60, 120 minutes, or greater. A plurality of elements are considered to affect stringency in a hybridization reaction such as temperature, salt concentration, and the like. Ausubel et al., Current Protocols in Molecular Biology, Wiley Interscience Publishers, (1995) can be referred for details. "Highly stringent condition", for example, is 0.0015 M sodium chloride, 0.0015 M sodium citrate, and 65-68° C. or 0.015 M sodium chloride, 0.0015 M sodium citrate, 50% formamide, and 42° C. Hybridization can be performed in accordance with the method described in experimental publications such as Molecular Cloning 2nd ed., Current Protocols in Molecular Biology, Supplement 1-38, DNA Cloning 1: Core Techniques, A Practical Approach, Second Edition, Oxford University Press (1995). In this regard, a sequence comprising only an A sequence or only a T sequence is preferably excluded from a sequence that hybridizes under stringent conditions. A moderately stringent condition can be readily determined by those skilled in the art based on, for example, the length of a DNA and is shown in Sambrook et al., Molecular Cloning: A Laboratory Manual, Third Ed., Vol. 1, 7.42-7.45 Cold Spring Harbor Laboratory Press, 2001, including, for a nitrocellulose filters, use of hybridization conditions of a pre-wash solution of 1.0 mM EDTA (pH 8.0), 0.5% SDS, and 5×SSC, and about 50% formamide and 2×SSC−6×SSC at about 40-50° C. (or other similar hybridization solutions such as a Stark's solution in about 50% formamide at about 42° C.) and washing conditions of 0.5×SSC, 0.1% SDS at about 60° C. Thus, the polypeptides used in the invention encompass polypeptides encoded by a nucleic acid molecule that hybridizes under highly or moderately stringent conditions to a nucleic acid molecule encoding a polypeptide described in the present invention in particular.

As used herein, a "purified" substance or biological agent (e.g., DNA vaccine, nucleic acid construct, plasmid DNA, other nucleic acid, protein or the like) refers to a substance or a biological agent from which at least a part of an agent naturally accompanying the substance or biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of a biological agent of the same type. The substance or biological agent used in the present invention is preferably a "purified" substance. An "isolated" substance or biological agent (e.g., nucleic acid, protein, or the like) as used herein refers to a substance or biological agent having agents that naturally accompany the substance or biological agent substantially removed. The term "isolated" as used herein varies depending on the objective. Thus, the term does not necessarily have to be represented by purity. However, when necessary, the term refers to the presence of preferably at least 75% by weight, more preferably at least 85% by weight, still more preferably at least 95% by weight, and most preferably at least 98% by weight of a biological agent of the same type. The substance used in the present invention is preferably an "isolated" substance or biological agent.

As used herein, a "corresponding" amino acid, nucleic acid, or moiety refers to an amino acid or a nucleotide which has or is expected to have, in a certain polypeptide molecule or polynucleotide molecule (e.g., CD63, CD81, CD9 or the like), similar action as a predetermined amino acid, nucleotide or moiety in a benchmark polypeptide or a polynucleotide for comparison, and, particularly in the case of enzyme molecules, refers to an amino acid which is present at a similar position in an active site and makes a similar contribution to catalytic activity and refers to a corresponding moiety in a complex molecule (e.g., heparan sulfate or the like). For example, for an antisense molecule, it can be a similar moiety in an ortholog corresponding to a specific moiety of the antisense molecule. A corresponding amino acid can be a specific amino acid subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case. Such a corresponding region or domain is useful for designing a complex molecule in the present invention.

As used herein, a "corresponding" gene (e.g., polynucleotide sequence or molecule) refers to a gene (e.g., polynucleotide sequence or molecule) of a certain species which has or is expected to have similar action as a predetermined gene in a benchmark species for comparison. When there is a plurality of genes having such action, the corresponding gene refers to a gene having the same evolutionary origin. Hence, a gene corresponding to a certain gene may be an ortholog of such a gene. Thus, a tetraspanin family protein such as CD63 corresponding to a human tetraspanin family protein such as CD63 can be found in other animals (especially mammals). Such a corresponding gene can be identified by using a technique that is well known in the art. For example, a corresponding gene in a certain animal (e.g., mouse) can be found by searching a database comprising sequences of the animal from using the sequence of SEQ ID NO: 1, 2 or the like as a query sequence, as a benchmark gene of the corresponding gene (e.g., tetraspanin family protein such as CD63 or the like).

As used herein, "fragment" refers to a polypeptide or polynucleotide with a sequence length of 1 to n−1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of the length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, such a fragment is understood to be within the scope of the present invention, for example, when a full length version functions as a marker or a target molecule, as long as the fragment itself also functions as a marker or a target molecule.

According to the present invention, the term "activity" as used herein refers to a function of a molecule in the broadest sense. Activity generally encompasses, but is not intended to be limited to, biological function, biochemical function, physical function, and chemical function of a molecule. Examples of activity include enzymatic activity, ability to interact with another molecule, ability to activate, promote, stabilize, inhibit, suppress, or destabilize a function of another molecule, stability, and ability to localize at a specific position in a cell. When applicable, the term is also directed to a function of a protein complex in the broadest sense. As used herein, "biological function", with regard to a gene or a nucleic acid or polypeptide related thereto, refers to a specific function that the gene, nucleic acid, or polypeptide can have in a living body. Examples thereof include, but are not limited to, production of a specific antibody, enzymatic activity, impartation of resistance, and the like. As used herein, "biological activity" refers to activity that a certain agent (e.g., polynucleotide, protein, or the like) can have in a living body, including activity exerting a variety of functions (e.g., transcription promoting activity) such as the activity of activating or deactivating a molecule from interaction with another molecule. When two agents interact, the biological activity thereof can be thought of as the bond between the two molecules and the biological change resulting therefrom, e.g., the two molecules are bound when precipitation of one of the molecules with an antibody results in co-precipitation of the other molecule. Thus, one method of determination includes observing such co-precipitation. When an agent is for instance an enzyme, the biological activity thereof encompasses the enzymatic activity thereof. Another example includes binding of a ligand to a corresponding receptor when an agent is a ligand. Such biological activity can be measured by a well-known technique in the art. Thus, "activity" refers to various measurable indicators that indicate or reveal the bond (either directly or indirectly) or affects a response (i.e., having a measurable effect in response to some exposure or stimulation). Examples thereof include the affinity of a compound that directly binds to the polypeptide or polynucleotide of the invention, the amount of proteins upstream or downstream after some stimulation or event, and a dimension of another similar function.

As used herein, "expression" of a gene, a polynucleotide, a polypeptide, or the like refers to the gene or the like being subjected to a certain action in vivo to be converted into another form. Preferably, expression refers a gene, a polynucleotide, or the like being transcribed and translated into a form of a polypeptide. However, transcription to make an mRNA is also one embodiment of expression. Thus, "expression product" as used herein encompasses such a polypeptide and protein, and mRNA. More preferably, such a polypeptide form can be a form which has undergone post-translation processing. Preferably, this acts as an antigen, so that a polypeptide or protein form is preferably as an expression product. For example, the expression level of a tetraspanin family protein such as CD63 or the like can be determined by any method. Specifically, the expression level of a tetraspanin family protein such as CD63 or the like can be found by evaluating the amount of mRNA of tetraspanin family protein such as CD63 or the like, the amount of protein of a tetraspanin family protein such as CD63 or the like, and the biological activity of the tetraspanin family protein such as CD63 or the like. Such a measurement value can be used in companion diagnosis. The amount of protein or mRNA of a tetraspanin family protein such as CD63 or the like can be determined by the method described in detail in other parts of the specification or a method known in the art.

As used herein, "functional equivalent" refers to any entity having the same function of interest but a different structure relative to the original target entity. Thus, it is understood that a functional equivalent of "tetraspanin family protein such as CD63 or the like" or an antibody thereof encompasses mutants and variants (e.g., amino acid sequence variant or the like) of the tetraspanin family protein such as CD63 or the like or antibody thereof that are not the tetraspanin family protein such as CD63 or the like or antibody thereof itself, which have the biological action of the tetraspanin family protein such as CD63 or the like or antibody thereof or can change, upon action, into the tetraspanin family protein such as CD63 or the like or the antibody thereof itself or a mutant or variant of the tetraspanin family protein such as CD63 or the like or the antibody thereof (e.g., including nucleic acids encoding a tetraspanin family protein such as CD63 or the like or an antibody thereof itself and mutants and variants of the tetraspanin family protein such as CD63 or the like or antibody thereof, and vector, cell and the like comprising such a nucleic acid). It is understood, even without specific mention, that a functional equivalent of a tetraspanin family protein such as CD63 or the like or an antibody thereof can be used in the same manner as the tetraspanin family protein such as CD63 or the like or antibody thereof. A functional equivalent can be found by searching a database or the like.

As used herein, "search" refers to utilizing a certain nucleic acid base sequence electronically, biologically, or by another method to find another nucleic acid base sequence having a specific function and/or property. Examples of electronic search include, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), Needleman and Wunsch method (Needleman and Wunsch, J. Mol. Biol. 48: 443-453 (1970)) and the like. Examples of biological search include, but are not limited to, stringent hybridization, a macroarray with a genomic DNA applied to a nylon membrane or the like or a microarray with a genomic DNA applied to a glass plate (microarray assay), PCR, in situ hybridization and the like. Herein, a gene used in the present invention is intended to include corresponding genes identified by such electronic search or biological search.

As a functional equivalent of the invention, it is possible to use an amino acid sequence with one or more amino acid insertions, substitutions, or deletions, or addition to one or both ends. As used herein, "one or more amino acid insertions, substitutions, or deletions, or addition to one or both ends in an amino acid sequence" refers to an alteration with a substitution of a plurality of amino acids or the like to the extent that can occur naturally by a well-known technical method such as site-directed mutagenesis or natural mutation. An altered amino acid sequence can have, for example, 1 to 30, preferably 1 to 20, more preferably 1 to 9, still more preferably 1 to 5, and especially preferably 1 to 2 amino acid insertions, substitutions, or deletions, or additions to one or both ends. Preferably, an altered amino acid sequence may be an amino acid sequence having one or more (preferably 1 or several, or 1, 2, 3 or 4) conservative substitutions in an the amino acid sequence of a tetraspanin family protein such as CD63 or the like. "Conservative substitution" refers herein to a substitution of one or more amino acid residues with other chemically similar amino acid residue so as not to substantially alter a function of a protein. Examples thereof include substitutions of a hydrophobic residue with another hydrophobic residue, substitutions of a polar residue with another polar residue having the same charge and the like. Functionally similar amino acids that can be substituted in this manner are known in the art for each amino acid. Specific examples include alanine, valine, isoleucine, leucine, proline, tryptophan, phenylalanine, methionine and the like for nonpolar (hydrophobic) amino acids, and glycine, serine, threonine, tyrosine, glutamine, asparagine, cysteine and the like for polar (neutral) amino acids. Examples of positively charged (basic) amino acids include arginine, histidine, lysine and the like. Further, examples of a negatively-charged (acidic) amino acid include aspartic acid, glutamic acid, and the like.

As used herein, an "antibody" includes a molecule capable of specifically bind to a specific epitope on an antigen or a population thereof. An antibody may be a polyclonal antibody or a monoclonal antibody. Antibodies can have various forms such as one or more forms selected from the group consisting of full length antibodies (antibodies with a Fab region and an Fc region), Fv antibodies, Fab antibodies, $F(ab')_2$ antibodies, Fab' antibodies, diabodies, single stranded antibodies (e.g., scFv), dsFv, multispecific antibodies (e.g., bispecific antibodies), peptides or polypeptides with an antigen binding property, chimeric antibodies (e.g., mouse-human chimeric antibodies, chicken-human chimeric antibodies, and the like), mouse antibodies, chicken antibodies, humanized antibodies, human antibodies, or an equivalent thereof. Antibodies also encompass modified and unmodified antibodies. Modified antibodies may be formed by an antibody binding to various molecules such as polyethylene glycol. A chemical modification can be applied to a modified antibody using a known approach. Such an antibody can also be covalently bound, or fused by recombination, to an enzyme such as alkaline phosphatase, horseradish peroxidase, or a galactosidase. The antibodies or the like used in the present invention can be of any origin, type, shape, or the like as long as the antibodies bind to a target thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized, but a monoclonal antibody is preferable. It is preferable that an antibody binds specifically to a target. Further, antibodies encompass modified and unmodified antibodies. Modified antibodies may be formed by an antibody binding to various molecules such as polyethylene glycol. A modified antibody can be obtained by applying a chemical modification to an antibody by using a known approach.

As used herein, "subject (person)" refers to a target subjected to prophylaxis, therapy, or the like of the invention, including humans and mammals excluding humans (e.g., one or more of mice, guinea pigs, hamsters, rats, rabbits, pigs, sheep, goats, cows, horses, cats, dogs, marmosets, monkeys, chimpanzees and the like).

As used herein, "agent" is broadly used interchangeably and may be any substance or other element (e.g., light, radiation, heat, electricity, and other forms of energy) as long as the intended objective can be achieved. Examples of such a substance include, but are not limited to, proteins, polypeptides, oligopeptides, peptides, polynucleotides, oligonucleotides, nucleotides, nucleic acids (including for example DNAs such as cDNAs and genomic DNAs and RNAs such as mRNAs), polysaccharides, oligosaccharides, lipids, organic small molecules (e.g., hormones, ligands, information transmitting substances, organic small molecules, molecules synthesized by combinatorial chemistry, small molecules that can be used as medicine (e.g., small molecule ligands and the like) and a composite molecules thereof. Typical examples of an agent specific to a polynucleotide include, but are not limited to, polynucleotides having complementarity with a certain sequence homology (e.g., 70% or greater sequence identity) to a sequence of the polynucleotide, polypeptides such as transcription factors that bind to a promoter region, and the like. Typical examples of an agent specific to a polypeptide include, but are not limited to, antibodies directed specifically to the polypeptide or a derivative or analog thereof (e.g., single chain antibody), specific ligands or receptors when the polypeptide is a receptor or ligand, substrates when the polypeptide is an enzyme, and the like.

Thus, an "agent" (or detection agent or the like) that "specifically" interacts (or binds) to a biological agent such as a polynucleotide or a polypeptide as used herein encompasses agents with affinity to the biological agent such as a polynucleotide or polypeptide that is typically the same or higher, preferably significantly (e.g., statistically significantly) higher, than the affinity to other unrelated polynucleotides or polypeptides (especially those with less than 30% identity). Such affinity can be measured, for example, by a hybridization assay, binding assay or the like.

As used herein, "therapy" refers to the prevention of exacerbation, preferably maintaining of the current condition, more preferably alleviation, and still more preferably disappearance of a disease or disorder (e.g., cerebral malaria) in case of such a condition, including being capable of exerting a prophylactic effect or an effect of improving a disease of a patient or one or more symptoms accompanying the disease. Preliminary diagnosis with suitable therapy may be referred to as "companion therapy" and a diagnostic agent therefor may be referred to as "companion diagnostic agent".

As used herein, "therapeutic drug (agent)" broadly refers to all agents capable of treating a condition of interest (e.g., disease such as cancer or the like), and refers to an inhibitor (e.g., antibody) provided by the present invention. In one embodiment of the present invention, "therapeutic drug" may be a pharmaceutical composition comprising an active ingredient and one or more pharmacologically acceptable carriers. A pharmaceutical composition can be manufactured, for example, by mixing an active ingredient with the carriers by any method known in the technical field of pharmaceuticals. Further, mode of usage of a therapeutic drug is not limited, as long as it is used for therapy. A therapeutic drug may be an active ingredient alone or a mixture of an active ingredient and any ingredient. Further, the shape of the carriers is not particularly limited. For example, the carrier may be a solid or liquid (e.g., buffer).

As used herein, "prevention" or "prophylaxis" refers to taking an action against a disease or disorder (e.g., cancer) from being in such a condition prior to being in such a condition. A prophylactic effect is also expected especially when used as a vaccine. For example, it is possible to use the agent of the invention to perform diagnosis, and optionally use the agent of the invention to prevent or take measures to prevent cancer or the like.

As used herein, "prophylactic drug (agent)" broadly refers to any agent capable of preventing a condition of interest (e.g., disease such as cancer or the like).

As used herein, "immune response enhancer" refers to any agent for enhancing at least one immune related response such as immune action or immune response. This is also called an immune enhancing drug or immunopotentiator.

Enhancement of immune responses includes T cell growth, enhancement of T cell responses, enhancement of activity of macrophage, and the like. The enhancement also includes reactions for enhancing immune responses that are suppressed by viruses or cancer. Adjuvants used with an antigen to enhance normal immunocompetence are also encompassed in immune response enhancers by definition.

As used herein, "enhancement of T cell response" refers to enhancement of an immune response by T cells, which encompasses antitumor immune responses. This is also referred to as T cell activation. Enhancement of T cell responses produces or grows, for example, memory T cells or effector T cells. Alternatively, such enhancement adjusts the activity of regulatory T cells. Alternatively, such enhancement can induce cytokine secretion by T cells, expand clones, or the like. At the effector stage of responses, effector $CD4^+$ T cells respond to an antigen by producing a cytokine with various actions such as B cell activation or leukocyte mobilization or activation, and $CD8^+$ cytotoxic T lymphocytes kill other cells.

As used herein, "cytotoxic agent" refers to any agent that damages cells. For example, a cytotoxic agent acts on other cells such as cancer cells upon cell division to destroy cells. Therefore, cytotoxic agents can also be used as an anticancer agent.

As used herein, "cancer" refers to any cancer that can be treated or prevented with the DNA vaccine or medicament of the invention. Examples of cancer include, but are not limited to, hepatocellular carcinoma, esophageal squamous cell carcinoma, breast cancer, pancreatic cancer, head and neck squamous cell carcinoma or adenocarcinoma, colorectal cancer, renal cancer, cerebral cancer (tumor), prostate cancer, small cell and non-small cell lung cancer, bladder cancer, bone or joint cancer, uterine cancer, cervical cancer, multiple myeloma, hematopoietic malignancy, lymphoma, Hodgkin's disease, non-Hodgkin's lymphoma, skin cancer, melanoma, squamous cell carcinoma, leukemia, lung cancer, ovarian cancer, gastric cancer, Kaposi's sarcoma, laryngeal cancer, endocrine cancer, thyroid cancer, parathyroid cancer, pituitary cancer, adrenal cancer, bile duct cell cancer, endometriosis, esophageal cancer, liver cancer, NSCLC, osteosarcoma, pancreatic cancer, SCLC, soft tissue tumor, AML, and CML.

As used herein, the terms "cytotoxic T lymphocytes", "cytotoxic T cells", and "CTL" are interchangeable, and refer to a subgroup of T lymphocytes that can recognize non-self cells (e.g., tumor/cancer cells and virally infected cells) and can induce the death of such cells, unless specifically defined otherwise.

As used herein, "kit" refers to a unit providing portions to be provided (e.g., vaccine, testing agent, diagnostic agent, therapeutic agent, antibody, label, manual, and the like), generally in two or more separate sections. This form of a kit is preferred when intending to provide a composition that should not be provided in a mixed state but is preferably mixed immediately before use for safety reasons or the like. Such a kit advantageously comprises instructions or a manual preferably describing how the provided portions (e.g., testing agent, diagnostic agent, or therapeutic agent) should be used or how a reagent should be handled. When the kit is used herein as a reagent kit, the kit generally comprises an instruction describing how to use a vaccine, testing agent, diagnostic agent, therapeutic agent, antibody, and the like.

As used herein, "instruction" is a document with an explanation of the method of use of the present invention for a physician or for other users. The instruction describes a detection method of the invention, how to use a diagnostic agent, or a description instructing administration of a medicament or the like. Further, an instruction may have a description instructing oral administration, or administration to the esophagus (e.g., by injection or the like) as the site of administration. The instruction is prepared in accordance with a format specified by a regulatory authority of the country in which the invention is practiced (e.g., Ministry of Health, Labour and Welfare in Japan, Food and Drug Administration (FDA) in the U.S., or the like), with an explicit description showing approval by the regulatory authority. The instruction is a so-called package insert, and is generally provided in, but not limited to, paper media. The instructions may also be provided in a form such as electronic media (e.g., web sites provided on the Internet or emails).

PREFERRED EMBODIMENTS

The preferred embodiments of the present invention are explained hereinafter. It is understood that the embodiments provided hereinafter are provided to better facilitate the understanding of the present invention, so that the scope of the present invention should not be limited by the following descriptions. Thus, it is apparent that those skilled in the art can refer to the descriptions herein to make appropriate modifications within the scope of the present invention. It is also understood that the following embodiments of the invention can be used individually or as a combination.

SUMMARY

A DNA vaccine is a potent dosage form that can elicit humoral or cell-mediated immune responses to an encoded antigen. However, immunogenicity needs to be improved in order to achieve an antigen specific $CD8^+$ T cell response.

(Exosome-Antigen Nucleic Acid Construct)

In one aspect, the present invention provides a nucleic acid construct (e.g., DNA construct) comprising a nucleic acid sequence encoding an exosome marker protein and a nucleic acid sequence encoding a vaccine antigen. A DNA vaccine, which is a representative embodiment of the nucleic acid construct of the invention, has expectation as a prophylactic vaccine for an infectious disease or cancer therapeutic vaccine because of the capability to strongly induce not only humoral immunity, but also cell-mediated immune response, especially cytotoxic T cells (CTL). Meanwhile, an expected effect was not attained in the past in clinical trials in view of the weak immunogenicity of DNA vaccines and safety issues in humans. As demonstrated in the Examples, the present invention provides a nucleic acid construct comprising a nucleic acid sequence encoding an exosome marker protein and a nucleic acid sequence encoding a vaccine antigen to reduce the immunogenicity of an exosome targeting DNA vaccine to a clinically applicable level. In addition, the clinical effect of an exosome vaccine with an antigen loaded in an exosome using this vaccine is confirmed. In view of the above, such a construct is noteworthy in terms of enabling clinical application of a DNA vaccine. For example, as described in the Examples, stronger CTL induction is confirmed relative to a group without expression of an antigen in an exosome, as a result of administering an exosome targeting DNA vaccine, which is a representative embodiment of the present invention, to a mouse by intramuscular electroporation. In this regard, in vitro transfection using a plasmid DNA (e.g., pCD63-OVA) encoding an OVA antigen which is fused with CD63, CD9, CD81, or the like used in the Examples resulted in transportation of OVA by the exosome. It has been revealed that strong CTL induction is attained as a result of not just localization to a membrane, but exosome targeting from comparison after making a plasmid DNA prepared by fusing CALNEXIN), which is a membrane protein of vesicles, to an ovalbumin (OVA) antigen. The superior effect of the present invention is demonstrated in the Examples and the like. Further, the inventors subcutaneously transplanted E.G-7, which is a type of thymus of mice expressing OVA, into mice using the DNA vaccine shown in the Examples, which are representative embodiments of the invention, and the mice were subsequently inoculated with the DNA vaccine. Consequently, tumor growth is confirmed to be strongly suppressed in a group inoculated with an exosome targeting DNA vaccine compared to a control group, thus demonstrating that a significant effect is also attained as an anticancer agent.

Any protein can be used as the exosome marker protein used in the present invention, as long as the objective of the invention, such as enhancement of the function of a DNA vaccine, can be achieved. Meanwhile in one embodiment, the exosome marker protein is preferably a protein that is present in a membrane of an exosome. Although not wishing to be bound by any theory, this is because use of a protein that is present in a membrane more advantageously achieves targeting to an exosome and advantageously achieve enhancement of a function as a DNA vaccine.

In a preferred embodiment, the exosome marker protein used in the nucleic acid construct of the invention is a protein that belongs to the tetraspanin family. The tetraspanin family is known as a surface marker for exosomes. Although not wishing to be bound by any theory, this is because it is understood that tetraspanin is involved in activation of cells or cell motility by forming a complex with integrin, growth factor receptor, or the like on a cellular membrane and repairing a function, thus targeting to an exosome is more advantageously achieved and enhancement of a function as a DNA vaccine is advantageously achieved.

In a specific embodiment, exosome marker proteins that can be used in the present invention include CD63, CD81, CD9, CD31, HLA-G, TSG101, Rab5b, ALIX, and the like, which are described in a database for exosomes (e.g., ExoCarta) or the like. Proteins described therein are proteins contained in exosomes. Nearly 10000 proteins are registered. In particular, CD63, CD81, CD9, CD31, and the like are known as representative tetraspanin. Since anticancer action and immune enhancing action are shown in experiments using CD63, CD9, or CD81, it is understood that members that are similarly present on another membrane, especially other members of tetraspanin, exhibit the same anticancer action and immune enhancing action. In one particularly preferred embodiment, such a protein is, but not limited to, CD63, CD9, or CD81, and more preferably CD63.

An antigen encoded by a nucleic acid contained in the nucleic acid construct of the invention can be any antigen, as long as the objective is functioning as a vaccine. Of course, an antigen is encoded as a nucleic acid, so that an antigen is a peptide, polypeptide, or a protein.

In a specific embodiment, the antigens used in the present invention include antigens of pathogens such as viral antigens, cancer antigen peptides, viral antigen peptides, virus derived proteins, and the like. Any antigen that can be used for diseases in which protect is expected against infections by CTL can be used.

In one embodiment, the nucleic acid construct of the invention can be a plasmid DNA. There can be an effect of facilitating administration to a subject or the like by using the construct in a form of a plasmid DNA.

In one aspect, the present invention provides a DNA vaccine comprising the nucleic acid construct of plasmid DNA of the invention. The nucleic acid construct or plasmid DNA contained in the DNA vaccine of the invention can comprise a combination of one or more features of the nucleic acid construct and plasmid of any embodiment explained herein as needed.

In another aspect, the present invention provides an exosome comprising a vaccine antigen protein and an exosome marker protein in a fused form. If the nucleic acid construct of the invention is used, this is generated in a form of an exosome marker protein fused with a vaccine antigen protein. An exosome comprising such a fusion protein can in itself be used as a medicament such as a vaccine. Thus, it is understood that the present invention also provides such an exosome itself. Such an exosome is different from a naturally-occurring exosome. This is called the exosome of the invention herein in some cases.

Therefore, the present invention also provides a protein in a form of a vaccine antigen protein fused with an exosome marker protein. As used herein, "fusion" refers to a state where a protein or a polypeptide is attached to another protein or a polypeptide, and mainly a state where two or more genes are integrally transcribed/expressed to form a single protein or a polypeptide in a protein or a polypeptide made artificially (by genetic engineering). In the present invention, fusion thus refers to a state where an exosome marker protein and a vaccine antigen are integrally transcribed/expressed to form a single protein or a polypeptide, which is also called the protein of the invention.

(Medicament or the Like)

In another aspect, the present invention also provides a medicament comprising the nucleic acid construct of the invention, the DNA vaccine of the invention, the protein of the invention, or the exosome of the invention. It is understood that the nucleic acid construct, DNA vaccine, protein, or exosome used in the medicament or the like of the invention can comprise any one or more additional features of the invention discussed in detail in the section of (Exosome-antigen nucleic acid construct) or the like.

In one embodiment, the present invention also provides an immune response enhancer comprising the nucleic acid construct of the invention, the DNA vaccine of the invention, the protein of the invention, or the exosome of the invention.

In another embodiment, the present invention provides a composition for enhancing a T cell response comprising the nucleic acid construct of the invention, the DNA vaccine of the invention, the protein of the invention, or the exosome of the invention.

In another embodiment, the present invention provides a cytotoxic agent comprising the nucleic acid construct of the invention, the DNA vaccine of the invention, the protein of the invention, or the exosome of the invention.

In yet another embodiment, the present invention is a medicament for treating or preventing cancer comprising the nucleic acid construct of the invention, the DNA vaccine of the invention, the protein of the invention, or the exosome of the invention.

In another embodiment, the present invention provides a method of enhancing an immune response in a subject, comprising administering to the subject an effective amount of the nucleic acid construct of the invention, the DNA vaccine of the invention, the protein of the invention, or the exosome of the invention. It is understood that the nucleic acid construct, DNA vaccine, protein, or exosome used in the method of the invention can comprise any one or more additional features of the invention discussed in detail in the section of (Exosome-antigen nucleic acid construct) or the like.

In one embodiment, the present invention provides a method of enhancing a T cell response, comprising administering to a subject an effective amount of the nucleic acid construct of the invention, the DNA vaccine of the invention, the protein of the invention, or the exosome of the invention.

In another embodiment, the present invention provides a method of treating or preventing cancer, comprising administering to a subject an effective amount of the nucleic acid construct of the invention, the DNA vaccine of the invention, the protein of the invention, or the exosome of the invention.

In this manner, the present invention is provided as a medicament (therapeutic drug or prophylactic drug) in various forms described above.

It is preferable that a route of administration of a therapeutic drug that is effective in therapy is used. For example, the route of administration may be intravenous, subcutaneous, intramuscular, intraperitoneal, or oral administration or the like. The dosage form may be, for example, injection, capsule, tablet, granule or the like. When a component of the invention is administered, use thereof as an injection is effective. An aqueous solution for injection may be stored, for example, in a vial or a stainless steel container. Further, an aqueous solution for injection may contain, for example, saline, saccharide (e.g., trehalose), NaCl, NaOH, or the like. Further, a therapeutic drug may contain a buffer (e.g., phosphate buffer), stabilizer, or the like. A dosage form that is suitable as a DNA vaccine is preferable.

The composition, medicament, therapeutic agent, prophylactic agent, and the like of the present invention generally comprise a therapeutically effective amount of therapeutic agent or active ingredient and a pharmaceutically acceptable carrier or excipient. As used herein, "pharmaceutically acceptable" means government regulatory agency-approved or Japanese Pharmacopoeia or other commonly recognized pharmacopoeia-listed for use in animals and more specifically in humans. As used herein, "carrier" refers to a diluent, adjuvant, excipient, or vehicle administered with a therapeutic agent. Such a carrier can be an aseptic liquid such as water or oil, including liquids derived from petroleum, animal, plant or synthesis, such as but not limited to peanut oil, soybean oil, mineral oil, sesame oil, and the like. When a medicament is orally administered, water is a preferred carrier. For intravenous administration of a pharmaceutical composition, saline and aqueous dextrose are preferred carriers. Preferably, aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt, and the like. When desired, the composition can contain a small amount of wetting agent or emulsifier or pH buffer. These compositions can be in a form of solution, suspension, emulsion, tablet, pill, capsule, powder, sustained release mixture, or the like. It is also possible to use traditional binding agents and carriers, such as tryglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U.S.A). Such a composition contains a therapeutically effective amount of therapeutic agent, preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

Examples of "salt" in one embodiment of the present invention include anionic salts formed with any acidic (e.g., carboxyl) group and cationic salts formed with any basic (e.g., amino) group. Salts include inorganic salts and organic salts, as well as salts described in, for example, Berge et al., J. Pharm. Sci., 1977, 66, 1-19. Further examples include metal salts, ammonium salts, salts with organic base, salts with inorganic acid, salts with organic acid, and the like. "Solvate" in one embodiment of the present invention is a compound formed with a solute and solvent. For example, J. Honig et al., The Van Nostrand Chemist's Dictionary P650 (1953) can be referred for solvates. When a solvent is water, a solvate formed is a hydrate. It is preferable that the solvent does not obstruct the biological activity of the solute. Examples of such a preferred solvent include, but not particularly limited to, water and various buffers. Examples of "chemical modification" in one embodiment of the present invention include modification with PEG or a derivative thereof, fluorescein modification, biotin modification, and the like.

When the present invention is administered as a medicament, various delivery systems are known, and such systems can be used to administer a therapeutic agent of the invention to a suitable site (e.g., esophagus). Such a system, for example, can use a recombinant cell that can express encapsulated therapeutic agent (e.g., polypeptide) in microcapsules, microparticles and liposomes, use endocytosis mediated by a receptor, construct a therapeutic nucleic acid as a part of a retrovirus vector or other vector, or the like. The method of introduction includes, but not limited to, intradermal, intramuscular, intraperitoneal, intravenous, subcutaneous, intranasal, epidural, and oral routes. A medicament can be administered by any suitable route, such as by injection, bolus injection, or by absorption through epithelial or mucocutaneous lining (e.g., oral cavity, rectum, intestinal mucosa, or the like). In addition, an inhaler or mistifier using an aerosolizing agent can be used as needed. Moreover, other biological activating agents can also be administered therewith. Administration can be systemic or local. The present invention, when used in cancer, may be administered through any suitable route such as direct injection into cancer (lesion) or the like.

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine, which alleviates the pain at the site of injection, and a solubilizing agent as needed. Generally, components can be supplied individually or by mixing the components together in a unit dosage form, and supplied, for example, in a sealed container such as an ampoule or sachet showing the amount of active agent, or as a lyophilized powder or water-free concentrate. When a composition is to be administered by injection, the composition can be distributed using an injection bottle containing aseptic agent-grade water or saline. When a composition is to be administered by injection, an aseptic water or saline ampoule for injection can also be provided such that the ingredients can be mixed prior to administration.

The composition, medicament, therapeutic agent, and prophylactic agent of the invention can be prepared as a neutral or salt form or other prodrugs (e.g., ester or the like). Pharmaceutically acceptable salts include salts formed with a free carboxyl group, derived from hydrochloric acid, phosphoric acid, acetic acid, oxalic acid, tartaric acid, or the like, salts formed with a free amine group, derived from isopropylamine, triethylamine, 2-ethylaminoethanol, histidine, procaine, or the like, and salts derived from sodium, potassium, ammonium, calcium, ferric hydroxide, or the like.

The amount of therapeutic agent of the invention that is effective in therapy of a specific disorder or condition may vary depending on the properties of the disorder or condition. However, such an amount can be determined by those skilled in the art by a standard clinical technique based on the descriptions herein. Furthermore, an in vitro assay can be used in some cases to assist the identification of the optimal dosing range. The precise dose to be used in a preparation may also vary depending on the route of administration or the severity of the disease or disorder. Thus, the dose should be determined in accordance with the judgment of the attending physician or the condition of each patient. The dosage is not particularly limited, but may be 0.001, 0.01, 0.1, 1, 5, 10, 15, 100, or 1000 mg/kg body weight per dosage or within a range between any two values described above. The dosing interval is not particularly limited, but may be, for example, 1 or 2 administration every 1, 7, 14, 21, or 28 days or 1 or 2 administrations in the range of period between any two values described above. The dosage, dosing interval, and dosing method may be appropriately selected depending on the age, weight, symptom, target organ or the like of the patient. Further, it is preferable that a therapeutic drug contains a therapeutically effective amount, or an amount effective for exerting a desired effect, of active ingredients. If a malignant tumor marker significantly decreases after administration, the presence of a therapeutic effect may be acknowledged. The effective dose can be estimated from a dose-response curve obtained from in vitro or animal model testing systems.

An agent such as the medicament of the invention or a therapeutic agent or a prophylactic agent can be provided as a kit.

In a specific embodiment, the present invention provides an agent pack or kit comprising one or more containers filled with one or more components of the composition, medicament, or the like of the invention. Optionally, information indicating approval of manufacture, use, or sale for administration to humans by a government agency regulating the manufacture, use or sale of medicaments or biological products in a stipulated form can be appended to such a container.

In a specific embodiment, the medicament or the like comprising a component of the invention can be administered via liposomes, microparticles, or microcapsules. In various embodiments of the present invention, it may be useful to use such a composition to achieve sustained release of the component of the invention.

The formulation procedure for the therapeutic drug, prophylactic drug, or the like of the invention as a medicament or the like is known in the art. The procedure is described, for example, in the Japanese Pharmacopoeia, the United States Pharmacopeia, pharmacopeia of other countries, or the like. Thus, those skilled in the art can determine the embodiment, such as the amount to be used, without undue experimentation from the descriptions herein.

(Novel Application of Exosome Marker Protein and Nucleic Acid Sequence Encoding the Same)

In another aspect, the present invention provides a novel application of an exosome marker protein and a nucleic acid sequence encoding the same.

In one aspect, the present invention provides a composition for improving immunogenicity of a vaccine DNA, comprising a nucleic acid sequence encoding an exosome marker protein. In another aspect, the present invention provides a nucleic acid (or nucleic acid molecule comprising a nucleic acid sequence) encoding an exosome marker protein for improving immunogenicity of a vaccine DNA. It is understood that the composition or nucleic acid of the invention can comprise any one or more additional features of the invention discussed in detail in the section of (Exosome-antigen nucleic acid construct) or the like.

In one embodiment, the exosome marker protein is a protein that is present in a membrane of an exosome in the composition or nucleic acid of the invention.

In another embodiment, the exosome marker protein belongs to the tetraspanin family in the composition or nucleic acid of the invention.

In yet another embodiment, the exosome marker protein is selected from the group consisting of any protein described in a database such as ExoCarta, e.g., CD63, CD81, CD9, CD31, HLA-G, TSG101, Rab5b, and ALIX in the composition or nucleic acid of the invention. More preferably, the exosome marker protein is CD63, CD9, or CD81. DNA vaccine inoculation of not only CD63, but also pCD9-OVA or pCD81-OVA resulted in a higher anti-OVA IgG2c/G1 ratio than vaccination with a control pOVA. Furthermore, the antigen specific $CD8^+$ T cell response also increased, and the level thereof was equivalent to pCD63-OVA vaccination. Thus, it is understood that tetraspanin generally exerts an immunologically excellent effect in DNA vaccines.

In yet another embodiment, an antigen contained in the vaccine DNA in the composition or nucleic acid of the invention includes antigens of pathogens such as viral antigens, viral antigen peptides, virus derived proteins, and the like.

In yet another embodiment, the vaccine DNA is a plasmid DNA in the composition or nucleic acid of the invention.

(General Techniques)

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997, and the like. The relevant portions (which can be the entire document) of the above documents are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (I996). Bioconjugate Techniques, Academic Press, and the like, the relevant portions of which are incorporated herein by reference.

For example, the oligonucleotide of the invention can also be synthesized herein by a standard method known in the art, such as using an automated DNA synthesizer (a synthesizer commercially available from Biosearch, Applied Biosystems, or the like). For example, a phosphorothioate-oligonucleotide can also be synthesized by the method of Stein et al. (Stein et al., 1988, Nucl. Acids Res. 16: 3209), and a methyl phosphonate-oligonucleotide can also be prepared using a control pore glass polymer support (Sarin et al., 1988, Proc. Natl. Acad. Sci. USA 85: 7448-7451).

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above explanation and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples are described hereinafter. When necessary, animals used in the following Examples were handled in compliance with the institutional guidelines of the National Institute of Biomedical Innovation, based on the Declaration of Helsinki for all animal experiments. For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, or the like).

Example 1

In this Example, the inventors tested whether a DNA vaccine encoding an antigen fused with CD63 can target an exosome, and whether immunogenicity of the vaccine can be improved by focusing on CD63, which is a tetraspanin protein expressed on various plasma membranes including exosome as an example of an exosome marker protein. The inventors constructed a plasmid expressing an OVA antigen fused with CD63 and made an antigen target exosomes. The inventors also attempted to identify the type of immune responses induced or promoted by exosome targeting of a DNA vaccine via a CD63 fusion antigen. In addition, the usefulness as an anticancer vaccine was evaluated.

(Materials and Methods)

DNA Construct

The cDNA of full-length CD63 (aa 1-238; SEQ ID NO: 3 to 4), CD9 (aa 1 to 226; SEQ ID NOs: 7 to 8), CD81 (aa 1 to 236; SEQ ID NOs: 11 to 12), and calnexin (aa 1 to 591; mouse NM_001110499 and NP_001103969. SEQ ID NOs: 13 to 14 (each from mouse)) was amplified by PCR using a C57BL/6J derived mouse lung cDNA library as a template. A cDNA fragment was investigated by sequencing and then introduced into a pCI mammalian expression vector (Promega), pCIneo-FLAG (Promega), or pEGFP-N1 (Clontech) as described above (Jounai, N., K. Kobiyama, M. Shiina, K. Ogata, K. J. Ishii, and F. Takeshita. 2011. J Immunol 186: 1646-1655.) cDNA (V00383.1; CAA23682.1 SEQ ID NOs: 15 to 16) encoding full length OVA (aa 1 to 386) was amplified by PCR from pCI OVA (pOVA) (Nagata, T., T. Higashi, T. Aoshi, M. Suzuki, M. Uchijima, and Y. Koide. 2001. Vaccine 20: 105-114.). OVA cDNA fragments were investigated by sequencing and then introduced into pCIneo-FLAG. They were named pOVA-FLAG. The full length OVA protein was fused at the N-terminus position with CD63, CD9, CD81, or calnexin. A glycine hexamer (6×glycine) was inserted between the OVA and the fused gene as a linker. Fused genes were investigated by sequencing and then introduced into a pCI vector, pCIneo-FLAG vector, or a pEGFP-N1 vector. They were named pCD63-FLAG (pCD63), pCD63-6×Gly-OVA-FLAG (pCD63-OVA), pCD9-6×Gly-OVA-FLAG (pCD9-OVA), pCD81-6×Gly-OVA-FLAG (pCD81-OVA), pCalnexin-6×Gly-OVA-FLAG (pCal-OVA), or pCD63-6×Gly-OVA-EGFP (pCD63-OVA-EGFP). All plasmids were transformed into *Escherichia coli* DH5a and purified using Qiagen Plasmid Endo-free Maxiprep kits (Qiagen) in accordance with the manufacturer's protocol.

Cells 293T cells and E.G7-OVA cells (E.G7) cells were purchased from American Type Culture Collection. FreeStyle™ 293-F cells (293F cells) were purchased from Life Technologies. 293T cells were cultured at 37° C. under 5% $CO_2$ in a DMEM supplemented with 50 μg/ml of penicillin-streptomycin and 10% FCS. 293F cells were cultured at 37° C. under 8% $CO_2$ in a FreeStyle™ 293 Expression medium (Life Technologies) (free of animal serum derived exosomes). E.G7 cells were cultured at 37° C. under 5% $CO_2$ in RPMI-1640 (Life Technologies) supplemented with 10% FCS, 50 μg/ml of penicillin-streptomycin, 0.05 mM of 2-mercaptoethanol, 1 mM of sodium pyruvate, 10 mM of HEPES, and 1× nonessential amino acid.

Exosome Isolation from Cell Culture Medium

Serum (exosome) free 293F cells were transfected for 48 to 72 hours with various DNA constructs. The supernatant of the medium was then collected and centrifuged for 30 minutes at 2000×g. Total Exosome Isolation kit (Life Technologies) was used according to the manufacturer's protocol to isolate exosomes from the culture medium. In short, 1.5 ml of Total Exosome Isolation reagent was added to 3 ml of cell culture medium, and the medium was incubated overnight at 4° C. and then centrifuged for 1 hour at 10,000×g at 4° C. Exosome pellets were resuspended in 100 μl of PBS. The properties of the collected exosomes were qualitatively and quantitatively evaluated as described below by electron microscopy, Western blotting, and flow cytometry.

Cell Transfection and Western Blotting

Cells were transfected as described previously (Jounai, N., K. Kobiyama, M. Shiina, K. Ogata, K. J. Ishii, and F. Takeshita. 2011. J Immunol 186: 1646-1655.) A transient transfection was performed with Lipofectamine 2000 (Life Technologies) according to the manufacturer's protocol. 293F cells ($1\times10^6$/ml) were transfected with their respective expression plasmids. The transfected cells were collected after 48 hours from transfection. The culture medium comprising the transfected cells were centrifuged for 30 minutes at 2000×g. The cells were dissolved in a RIPA buffer and incubated for 15 hours on ice. The supernatant and the isolated exosome samples were diluted with 3×SDS buffer (125 mM of Tris-HCl: pH 6.8, 4% SDS, 20% glycerol, and 0.01% bromophenol blue) and boiled for 5 minutes at 95° C. Immunoblotting analysis was performed as described above using an anti-CD63 Ab (R5G2, MEDICAL & BIOLOGICAL LABORATORIES CO., LTD), anti-calnexin Ab (ab22595, Abcam), or anti-FLAG M2-peroxidase (HRP) Ab (A8592, Sigma) (Jounai, N., K. Kobiyama, M. Shiina, K. Ogata, K. J. Ishii, and F. Takeshita. 2011. J Immunol 186: 1646-1655.)

Immunogold Electron Microscopy

An immunogold electron microscope assay was conducted as described previously (Thery, C., S. Amigorena, G. Raposo, and A. Clayton. 2006. Current protocols in cell biology/editorial board, Juan S. Bonifacino . . . [et al.] Chapter 3: Unit 3.22.). The isolated exosomes were immunolabeled using mouse anti-FLAG Ab (Sigma) as the primary Ab and gold-labeled anti-mouse IgG (10 nm Gold) (Abcam) as the secondary Ab.

Figure 5:
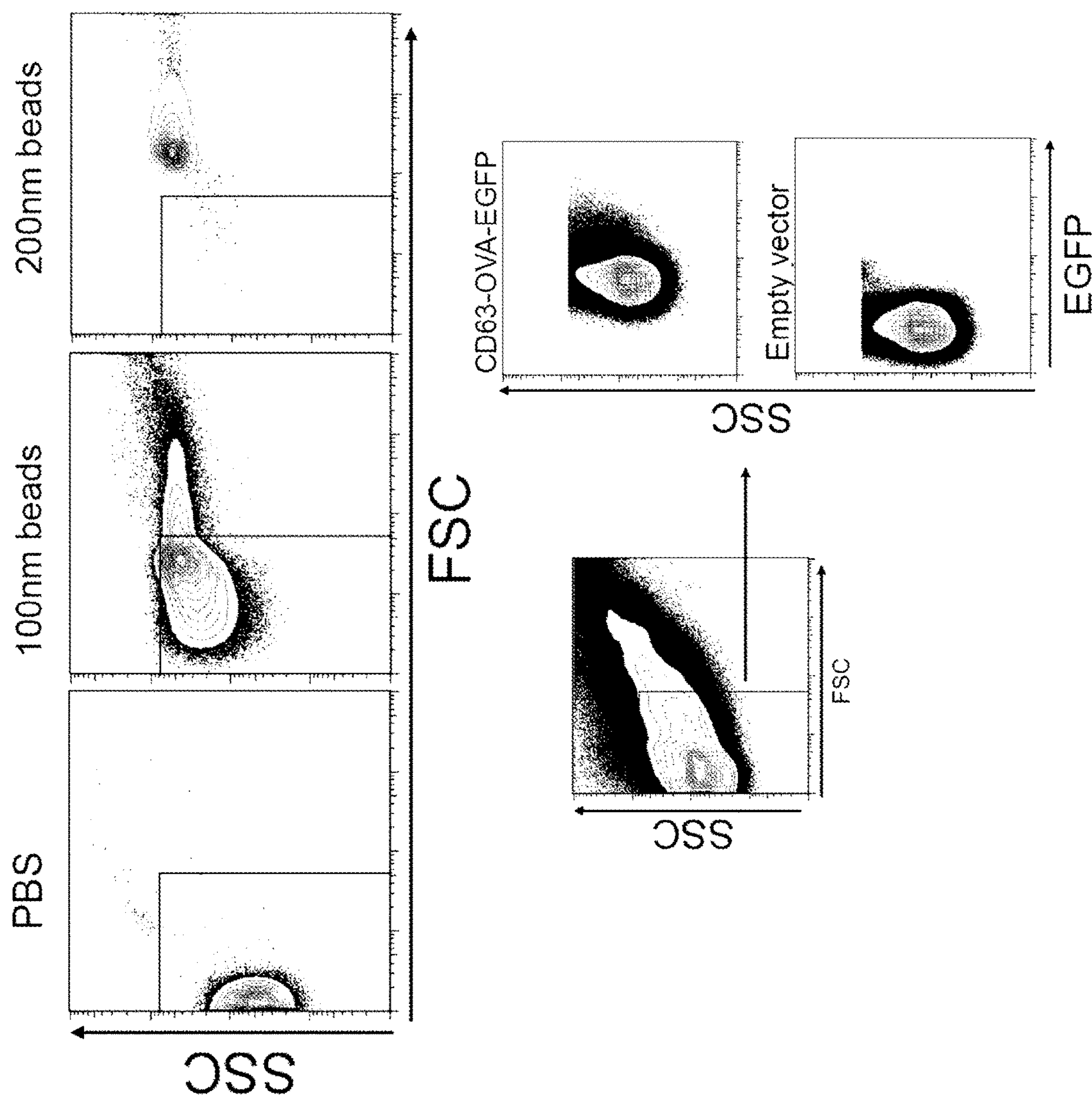
FIG. 5 CD63-OVA-EGFP (EGFP indicates enhanced GFP) in the exosome fraction. Either a pCD63-OVA-EGFP vector or an empty vector was transiently transfected into 293F cells. The supernatant of each culture was collected after 48 days from transfection. The gating strategy for determining an exosome fraction was based on SSC to FCS by using PBS, 100 nm beads, and 200 nm beads. The results of analysis by flow cytometry are shown. The top row shows cases of using, from the left, PBS, 100 nm beads, and 200 nm beads. The left side of the bottom row shows analysis of supernatant. The right side shows the exosome fraction after gating.

Flow Cytometry Analysis 293F cells ($1\times10^6$/ml) were transfected with pCD63-OVA-EGFP. The culture medium comprising the transfected cells was collected after 48 hours from transfection and centrifuged. The properties of the resulting supernatant were evaluated with INFLUX (BD Bioscience) (18). 100 nm beads and 200 nm beads (Polysciences, Inc.) were used to determine the suitable gating for the exosome fraction (FIG. 5).

Animal and Immunization 6 week old female C57BL/6J mice were purchased from CLEA Japan, Inc. The mice were immunized (50 μl/muscle) by intramuscular electroporation (imEPT) using a plasmid DNA (50 μg) encoding a control or fusion protein (OVA, CD63, CD63-OVA, CD9-OVA, CD81-OVA, or Cal-OVA) in nuclease free saline.

For exosome immunization, the mice were immunized twice at the tail base on day 7 after the first immunization with 600 μg of exosome protein (OVA 40 ng) or OVA protein (40 ng) (Hyglos Gmbh) (total volume: 100 μl/mouse) in PBS. The purified exosomes used for immunizing the mice were isolated from cells that were transfected with pOVA-, pCD63-OVA, or pCal-OVA. The concentrations of the purified exosome protein and cell culture supernatant were tested using RC DC Protein Assay (BIO-RAD) according to the manufacturer's protocol. After 1 week from the last vaccination, the mice were slaughtered to measure antigen specific immune responses of the mice.

All animal experiments were conducted in accordance with the institutional guidelines for the animal facility of the National Institutes of Biomedical Innovation, Health and Nutrition.

Evaluation of Cell-Mediated Immune Response

In order to evaluate the cell-mediated immune responses, splenocytes ($2\times10^6$/well) were prepared and incubated in a RPMI-1640 complete medium containing 20 μg/ml of OVA peptide ($OVA_{257-264}$, H-$2K^b$ restricted OVA class I epitope, or $OVA_{323-339}$, I-A(d)-restricted OVA class II epitope) or OVA antigen (Calbiochem). Cell-mediated immune responses were measured as described previously (Onishi, M., et al., 2015. J Immunol 194: 2673-2682.)

ELISA 293T cells ($1\times10^6$/ml) were transfected with each expression plasmid. The cells were incubated for 48 hours after transfection, and the concentration of OVA expression in cell culture supernatant and cells was measured with ELISA (Institute of Tokyo Environmental Allergy) according to the manufacturer's protocol. The OVA specific serum Ab titer was measured as described previously (Onishi, M., et al., 2015. J Immunol 194: 2673-2682.)

Tetramer Assay

A tetramer assay was conducted as described previously (Kobiyama, K., et al., 2014. Proc Natl Acad Sci USA 111: 3086-3091.) In short, splenocytes were stained at room temperature for 20 minutes using a PE labeled H-$2K^b$ OVA tetramer (SIINFEKL) (MEDICAL & BIOLOGICAL LABORATORIES CO., LTD.). Next, the cells were stained with FITC labeled anti-CD8a (KT15, BioLegend), PC labeled anti-TCRB chain (H57-597, BioLegend), Brilliant Violet 421™ labeled anti-CD62L (MEL-14, BioLegend), and APC/Cy7 labeled anti-CD44 (IM7, BioLegend) Ab in PBS. The OVA $tetramer^+CD44^+CD8a^+TCRb^+$ cell count was determined by flow cytometry.

In Vivo CTL Assay in vivo CTL assay was conducted as described previously (Kobiyama, K., et al., 2014. Proc Natl Acad Sci USA 111: 3086-3091.) In short, 6 week old C57BL/6J mice were vaccinated with a DNA vaccine. On day 21, naïve C57BL/6J mouse derived splenocytes were labeled for 10 minutes at 37° C. with 2 or 0.2 μM of CFSE. The CFSE labeled cells were incubated for 90 minutes at 37° C. with $OVA_{257-264}$ (10 μg/ml) to subject to peptide pulsing. The cells were then washed and the same number from each treatment group was delivered to immunized mice through an intravascular route. Splenocytes were isolated after 24 hours from the delivery to analyze CFSE labeled cells by flow cytometry.

Tumor Challenge

The hair on the back of mice was shaved. $1\times10^6$ E.G7 cells in 100 μl of PBS were subcutaneously injected into the mice. When the average tumor volume reached 1 $cm^3$, the mice were subjected to primary immunization with pOVA, pCD63-OVA, pCal-OVA, or pCIneo-FLAG (as a negative control). In the tumor prevention experiment, mice were immunized with such plasmid DNA vaccines, and E.G7 cells were injected at $1\times10^6$ cells in 100 μl of PBS after 10 days. The tumor volume was measured at regular intervals using a digital caliper to calculate the length×width×height.

Statistical Analysis

The statistical significant of the difference among the groups was determined using Mann-Whitney U test.

(Results)

CD63 fusion antigens captured in exosomes act as a vaccine

It has been previously reported that antigen containing exosome vaccine inoculation induces Th1 responses and CTL activation (Wolfers, J., et al., 2001. Nat Med 7: 297-303., Qazi, K. R., et al., 2009. Blood 113: 2673-2683). To find out whether expression of CD63 fused with an antigen in a cell induces highly efficient antigen secretion by simple expression of only antigens, the inventors constructed a plasmid DNA (pCD63-OVA) encoding a fusion protein of CD63 and OVA. The inventors have decided to target OVA antigens to exosomes via CD63 because CD63 is expressed on the exosome membrane and is already used as a common exosome marker (Pols, M. S., and J. Klumperman. 2009. Experimental cell research 315: 1584-1592.) In addition, the inventors prepared aa control plasmid DNA (pCal-OVA) encoding a calnexin-OVA fusion protein as a control. pCal-OVA targets an encoded antigen to the membrane of endoplasmic reticulum (Baietti, M. F., Z. et al., 2012. Nat Cell Biol 14: 677-685.; Gross, J. C., V. Chaudhary, K. Bartscherer, and M. Boutros. 2012. Nat Cell Biol 14: 1036-1045.; Lasser, C., V. S. Alikhani, K. Ekstrom, M. Eldh, P. T. Paredes, A. Bossios, M. Sjostrand, S. Gabrielsson, J. Lotvall, and H. Valadi. 2011. J Transl Med 9: 9.)

Figure 1B:
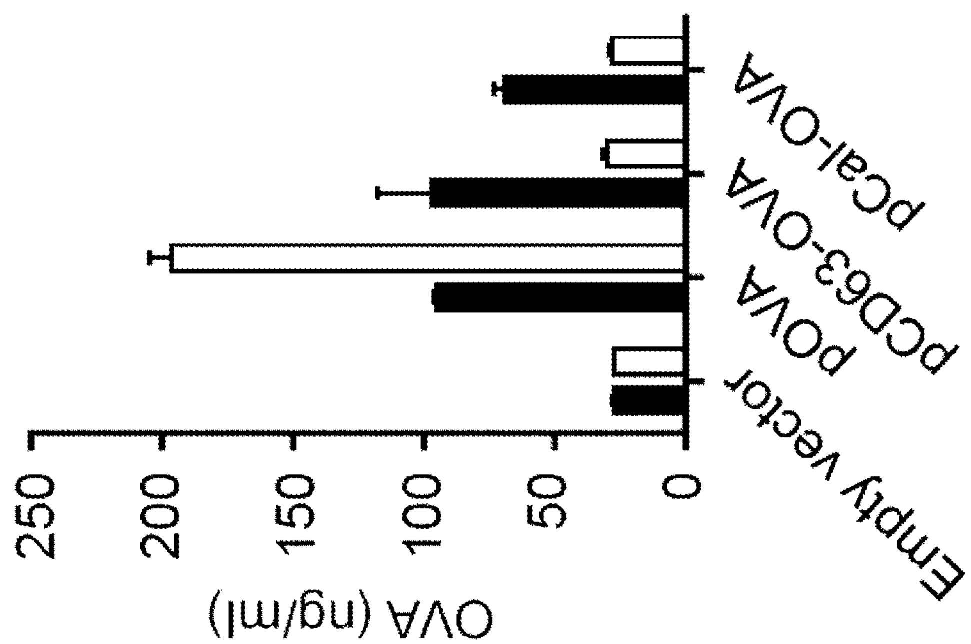
FIG. 1B Evaluation of antigen expressing exosomes as a CTL inducing immunogen. (A, B) An empty vector, pOVA, pCD63, pCD63-OVA, or pCal-OVA was transiently transfected into 293-F cells and 293T cells. After 48 hours from transfection, the supernatant was separated from the cells, and the exosome fraction was purified. (A) The cell, supernatant, and exosome fractions were analyzed by immunoblotting. (B) ELISA was used on the cells and supernatant to analyze the OVA protein concentration. The error bar represents the SD. The black bars indicate cells, and white bars indicate supernatant.
Figure 1C:
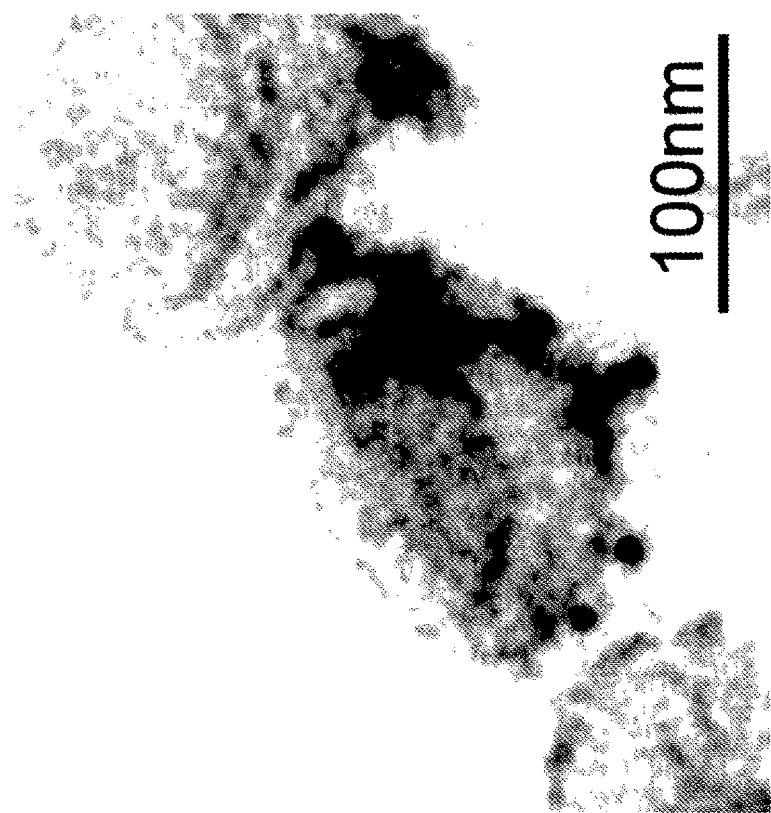
FIG. 1C Evaluation of antigen expressing exosomes as a CTL inducing immunogen. (C) Detection of exosomes with a scanning electron microscope. The left scanning electron microscope image shows an empty vector transfected 293F cell derived exosome, which is a negative control. The right scanning electron microscope image shows a pCD63-OVA transfected 293F cell derived exosome. The scale bar indicates 100 nm.
Figure 1C:
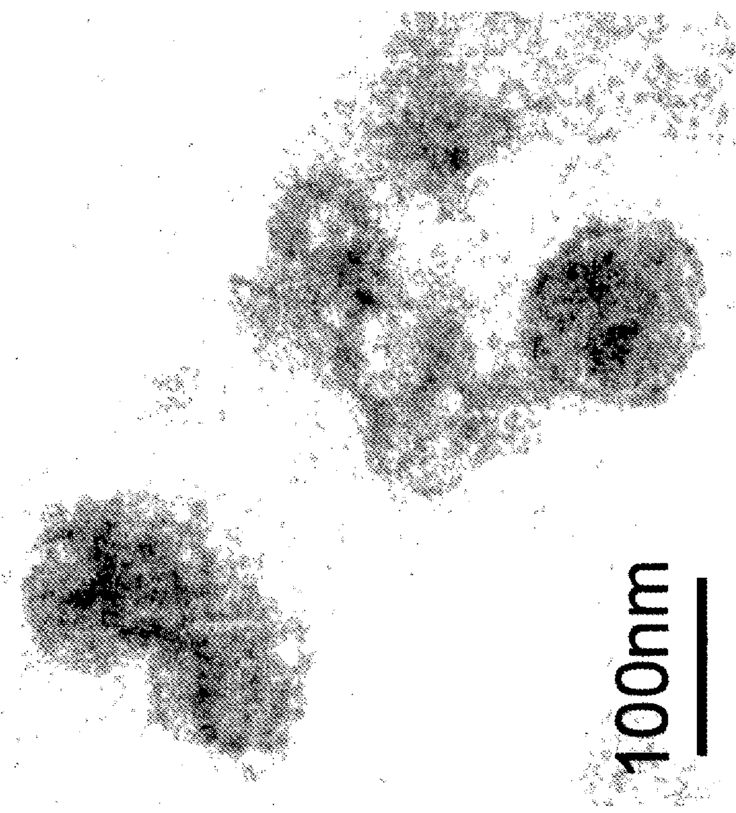

Serum (exogenous exosome) free 293-F cells were transfected with each of the aforementioned plasmid DNAs. The exosomes in the serum were collected and purified from a cell culture medium using an exosome isolation reagent. The inventors then used a Western blot assay to analyze the expression of a fusion protein encoded in the cell lysate, serum, and exosome fraction (FIGS. 1A and 1B). Exosome fractions in all groups contained CD81, which is another exosome marker, but not serum. Furthermore, only the cell fraction contained calnexin. In addition, the purity of each fraction was studied (FIG. 1A). Under these conditions, OVA proteins were also detected in the serum after pOVA transfection (FIGS. 1A and 1B). In contrast, neither CD63 nor CD63-OVA fusion protein were detected in the serum, but they were both detected from the cell lysate and exosome fractions (FIGS. 1A and 1B). An endoplasmic reticulum (ER) targeting calnexin-OVA fusion protein was detected in a cell lysate, but not in the exosome fraction (FIGS. 1A and 1B). The inventors then investigated whether a CD63-OVA protein is localized on/in an exosome. The inventors used a plasmid encoding an EGFP- or FLAG-fusion protein to analyze the CD63 expression by flow cytometry and electron microscopy. Results of both analyses suggest that CD63-OVA fusion proteins in fact target exosomes (FIGS. 1C and 5).

Figure 1D:
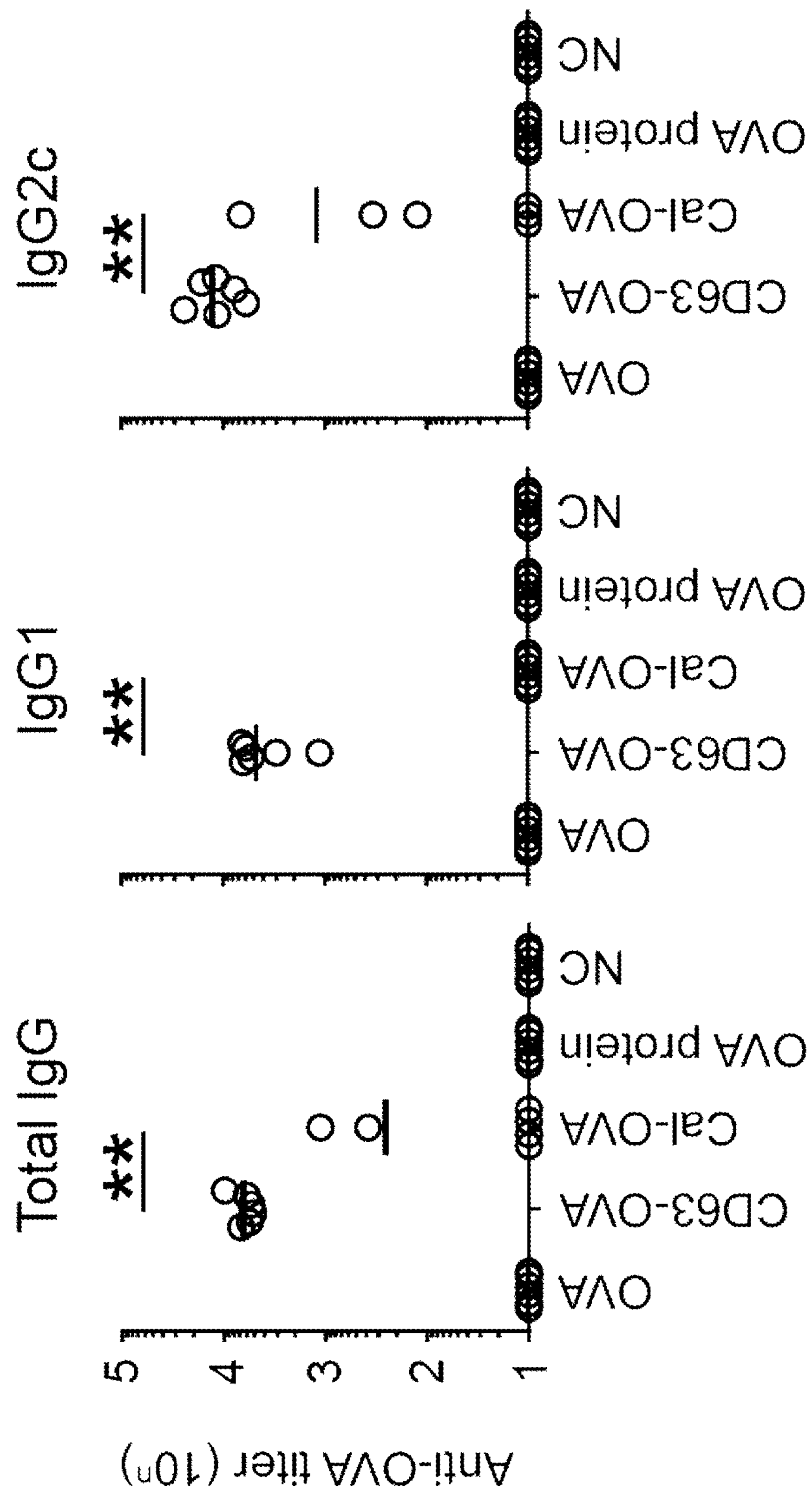
FIG. 1D Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the OVA specific IgG titer, OVA specific serum IgG1 titer, and OVA specific serum IgG2c titer. The vertical axis indicates the respective logarithmic antibody titer. Data represents two independent experiments. The error bar represents the SD. ** indicates $p<0.005$ (Mann-Whitney U test). As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.
Figure 1E:
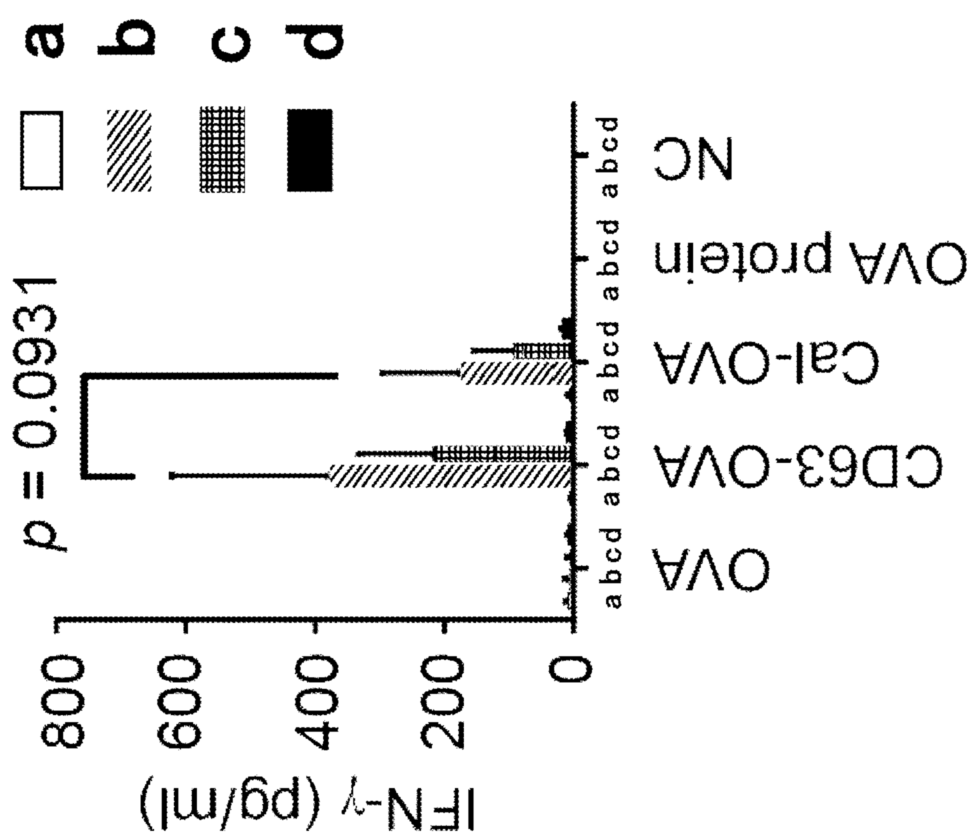
FIG. 1E Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the IFN-γ level induced in splenocytes by OVA, $OVA_{257-264}$, $OVA_{323-339}$, or a medium. Data represents two independent experiments. The error bar represents the SD. As for the labels of the bars, a indicates the medium, b indicates $OVA_{257-264}$, c indicates $OVA_{323-339}$, and d indicates OVA. As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.
Figure 1F:
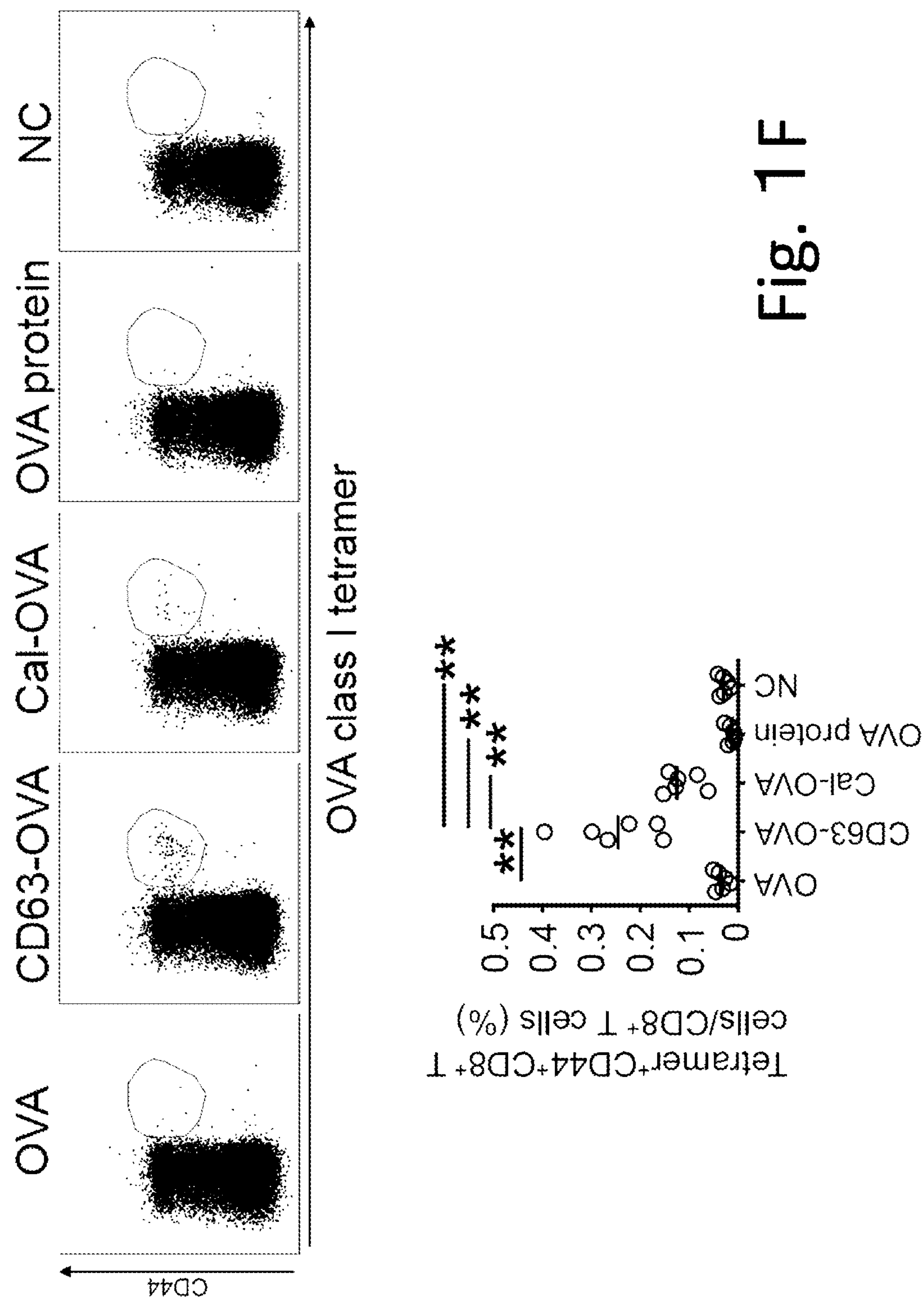
FIG. 1F Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the ratio of $CD8^+$ T cells recognized by an $OVA_{257-264}$ specific tetramer. The top diagram shows results of FACS analysis on CD44 and OVA class I tetramer, and the bottom diagram shows the ratio of cells in the encircled region in the top diagram. Data represents two independent experiments. ** indicates $p<0.005$ (Mann-Whitney U test). As for the bar labels, a, b, c, and d indicate medium, $OVA_{257-264}$, $OVA_{323-339}$, and OVA, respectively. As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.

The inventors then investigated whether a purified exosome derived from serum free cell culture supernatant of cells that were transiently transfected with a CD63-OVA protein acts as a vaccine that induces sufficient OVA specific immune responses. The inventors transfected cells with pOVA, pCD63-OVA, or pCalnexin-OVA and then collected exosomes from the cell culture supernatant, and subcutaneously immunized C57/BL6 naïve mice at the tail base with the purified exosomes. After one week from the primary immunization, both antigen specific humoral and cellular immune responses were evaluated. CD63-OVA containing exosome immunization induced a higher antigen specific antibody response than any other tested immunization (FIG. 1D). More interestingly, immunization with CD63-OVA containing exosomes induced antigen specific IFN-γ acidic $CD8^+$ T cells, but such induction was not observed for other tested immunization (FIGS. 1E and 1F). These results strongly suggest that exosome fraction derived CD63-OVA induce a more potent $CD8^+$ T cell response than exosome fraction derived OVA alone or calnexin-OVA.

Figure 1G:
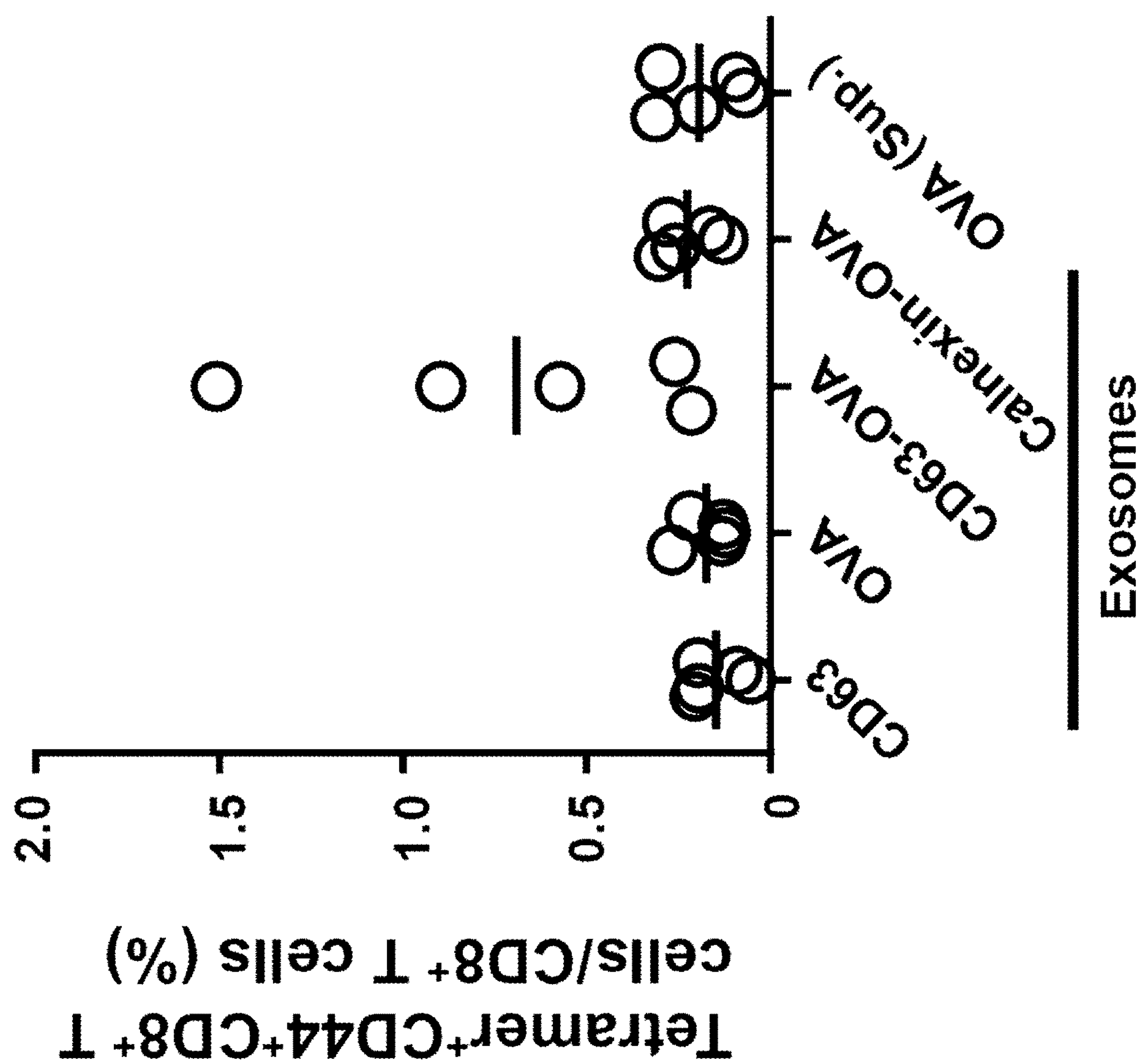
FIG. 1G C57BL/6J mice (n=5) were immunized by introducing an OVA protein or purified exosome isolated from pCD63 transfected cells, pOVA transfected cells, pCD63-OVA transfected cells, or pCalnexin-OVA transfected cells through a transdermal route. On day 35 after immunization on day 0, day 14, and day 28, the spleen was used to measure the ratio of $CD8^+$ T cells recognized by an $OVA_{257-264}$ specific tetramer. As for the horizontal axis labels, CD63, OVA, CD63-OVA, and Calnexin-OVA indicate the use of a purified exosome isolated from, from the left, pCD63 transfected cells, pOVA transfected cells, pCD63-OVA transfected cells, and pCalnexin-OVA transfected cells, respectively.

The same experiment as FIG. 1F was repeated. In other words, C57BL/6J mice (n=5) were immunized by introducing an OVA protein or a purified exosome isolated from pCD63 transfected cells, pOVA transfected cells, pCD63-OVA transfected cells, or pCalnexin-OVA transfected cells through a transdermal route. FIG. 1G shows the results of measuring the ratio of $CD8^+$ T cells recognized by an $OVA_{257-264}$ specific tetramer using a spleen on day 35 after immunization on day 0, day 14, and day 28. FIG. 1G show the same result as FIG. 1F.

Targeting of Antigen to Exosome Improves Immunogenicity of DNA Vaccine

Figure 2A:
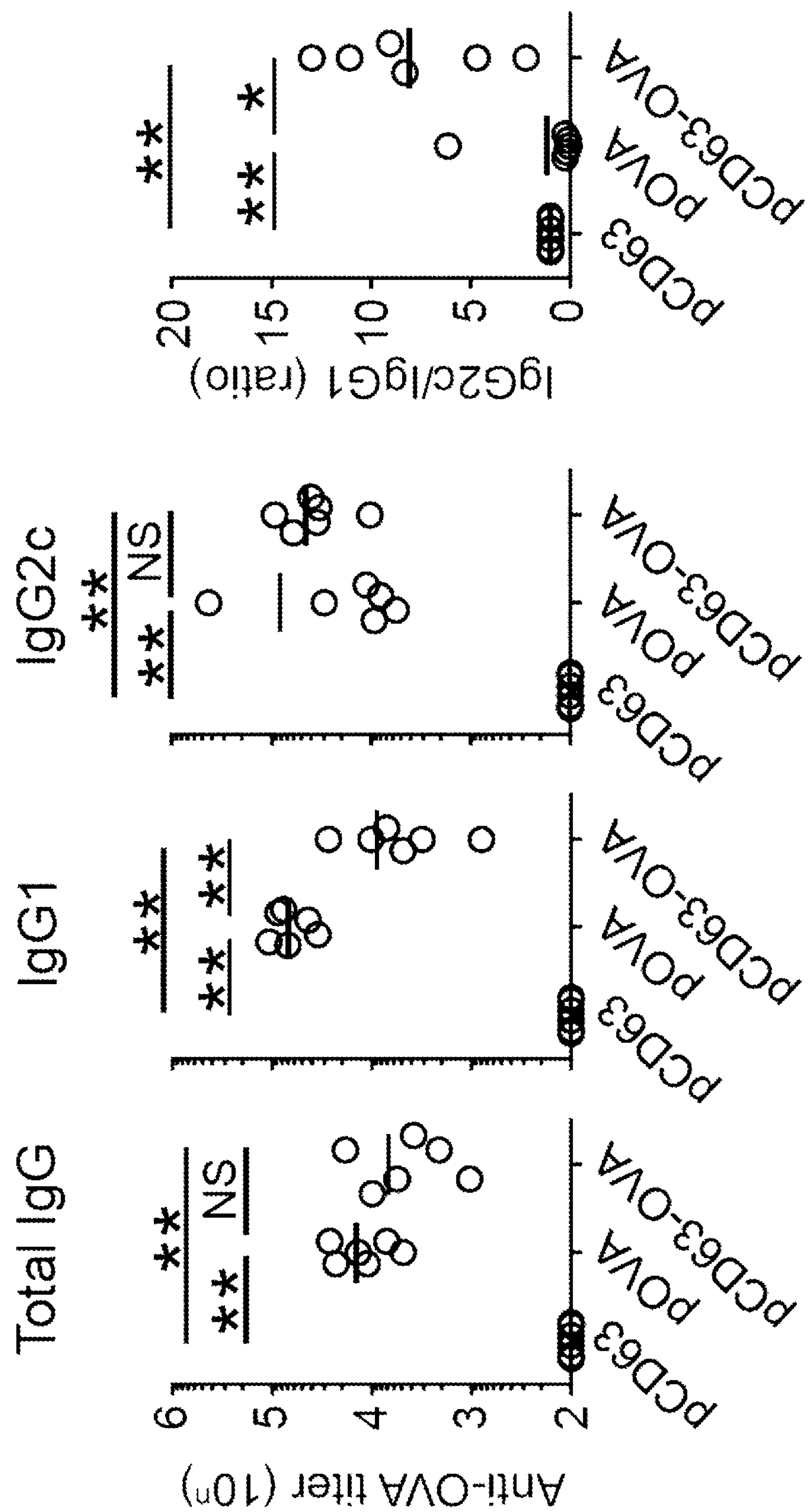
FIG. 2A The effect of antigen targeting to an exosome on immunogenicity of a DNA vaccine. (A-C) C57BL/6J mice (n=6) were immunized by introducing pOVA, pCD63, or pCD63-OVA by intramuscular electroporation (50 μg/mouse). On day 21 after immunization with these plasmids on day 0 and day 14, OVA specific IgG titer, OVA specific serum IgG1 titer and OVA specific serum IgG2c titer were measured to monitor the ratio of OVA specific serum IgG2c to OVA specific serum IgG1. Data represents two independent experiments. * indicates $p<0.05$, and ** indicates $p<0.005$ (Mann-Whitney U test).
Figure 2B:
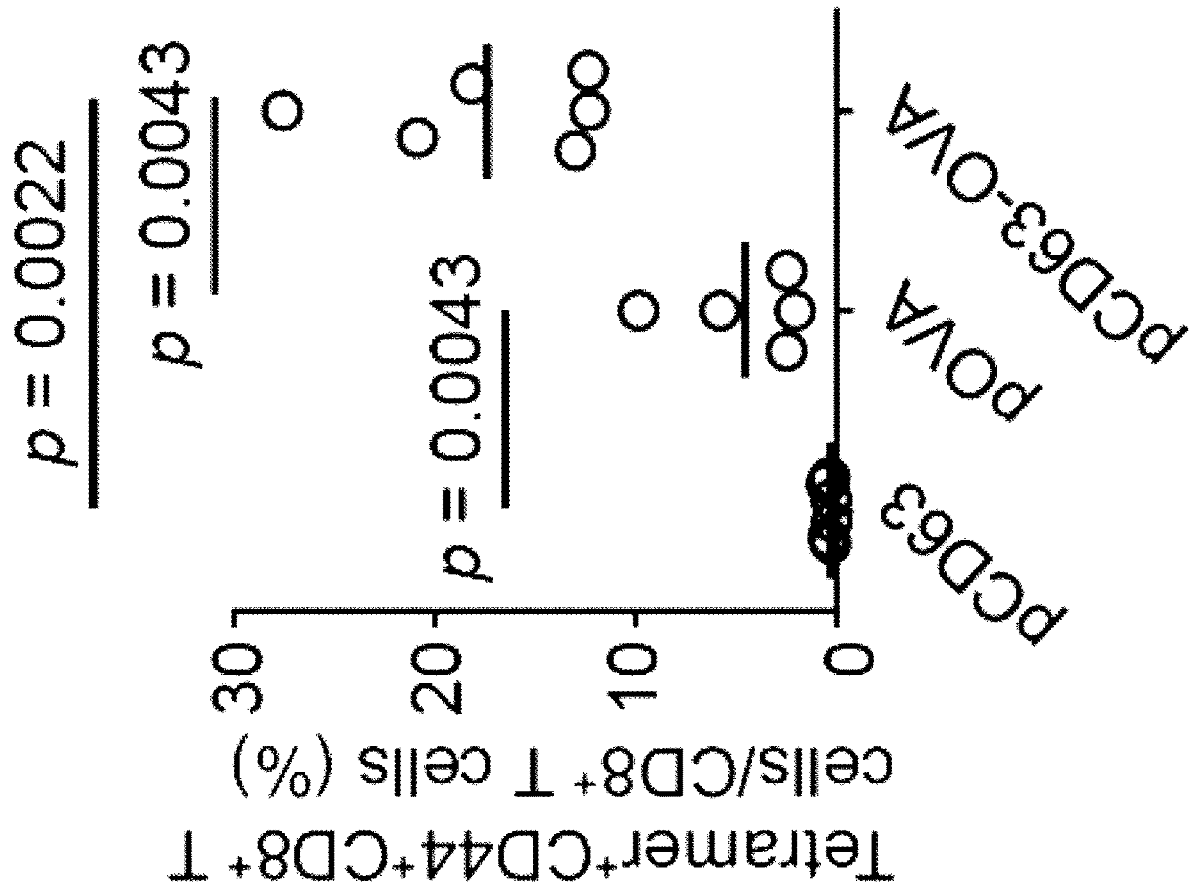
FIG. 2B The effect of antigen targeting to an exosome on immunogenicity of a DNA vaccine. C57BL/6J mice (n=6) were immunized by introducing pOVA, pCD63, or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (B), and IFN-γ level induced in splenocytes by OVA, $OVA_{257-264}$, $OVA_{323-339}$, or a medium were monitored. Data represents two independent experiments. The error bar represents the SD. * indicates $p<0.05$ and ** indicates $p<0.005$ (Mann-Whitney U test).
Figure 2C:
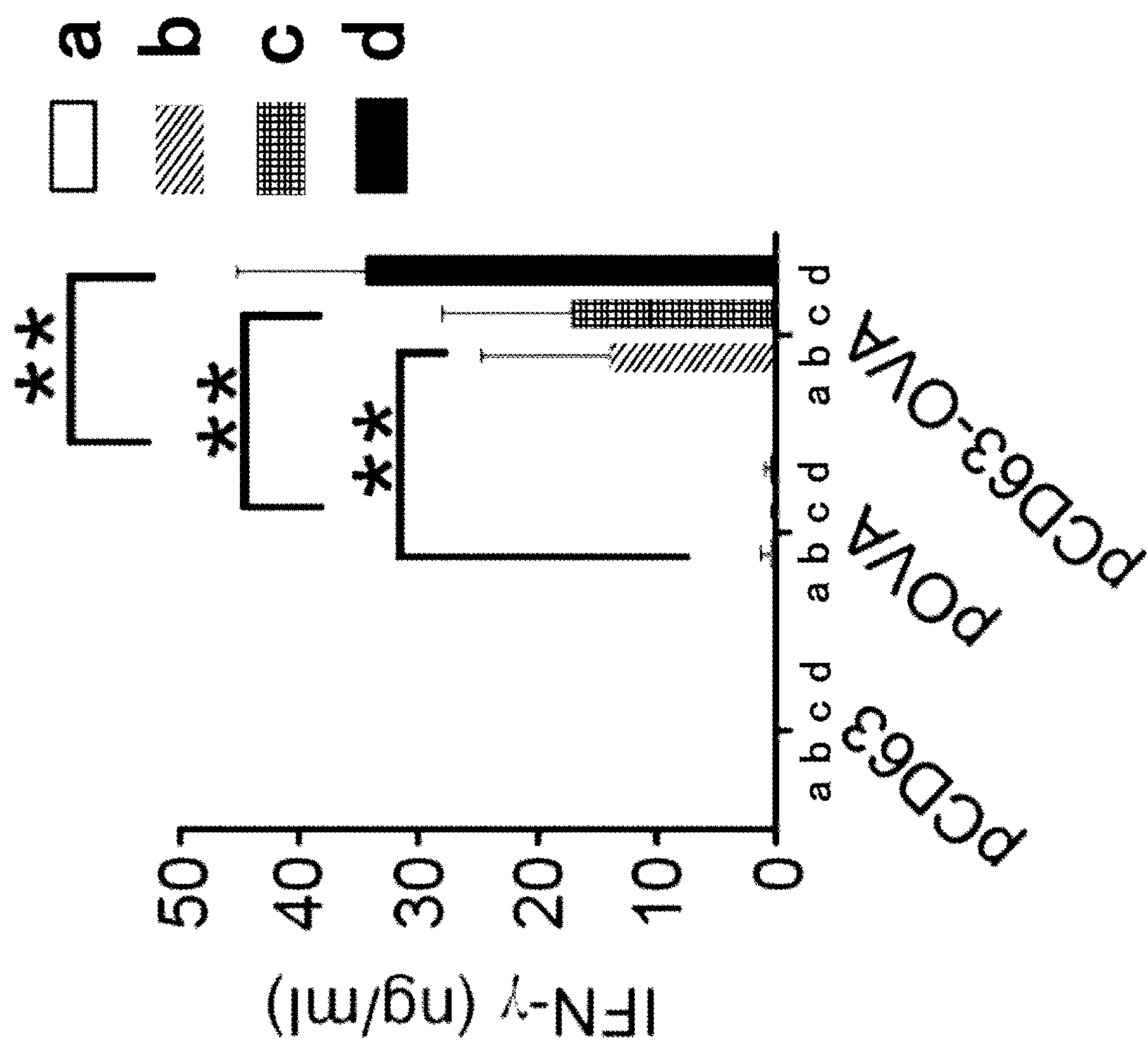
FIG. 2C The effect of antigen targeting to an exosome on immunogenicity of a DNA vaccine. C57BL/6J mice (n=6) were immunized by introducing pOVA, pCD63, or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (B), and IFN-γ level induced in splenocytes by OVA, $OVA_{257-264}$, $OVA_{323-339}$, or a medium were monitored. Data represents two independent experiments. The error bar represents the SD. * indicates $p<0.05$ and ** indicates $p<0.005$ (Mann-Whitney U test). For the bar labels, a, b, c, and d indicate medium, $OVA_{257-264}$, $OVA_{323-339}$, and OVA, respectively.

Based on the above results, the inventors hypothesized that a DNA vaccine with an antigen targeting an exosome incorporated therein would have increased immunogenicity. To investigate whether a DNA vaccine with pCD63-OVA has increased immunogenicity compared to other control DNA vaccines, the inventors immunized mice twice with a plasmid DNA using imEPT to induce efficient transfection in vivo. After 1 week from booster immunization, pCD63-OVA immunized mice had significantly lower serum anti-OVA IgG1 titer than pOVA immunized mice, but there was no difference in anti-OVA total IgG and IgG2c between the two groups (FIG. 2A). If the anti-OVA IgG2c/G1 ratios of the pCD63-OVA and pOVA are compared, a higher value of anti-OVA IgG2c/G1 was observed in pCD63-OVA immunized mice relative to pOVA (FIG. 2A). The inventors then studied the frequency of $OVA_{257-264}$ specific $tetramer^+$ $CD44^+CD8^+$ T cells in these immunized mice. A high frequency of $OVA_{257-264}$ specific $tetramer^+CD44^+CD8^+$ T cells was observed in pCD63-OVA immunized mice relative to pOVA immunized mice (FIG. 2B). The inventors also stimulated splenocytes with either class I ($OVA_{257-264}$) or class II ($OVA_{323-333}$) OVA peptide ex vivo and then measured cytokine production from the splenocytes by ELISA. A significantly higher level of IFN-γ production was detected for each peptide stimulation with pCD63-OVA vaccination relative to pOVA (FIG. 2C).

Figure 6A:
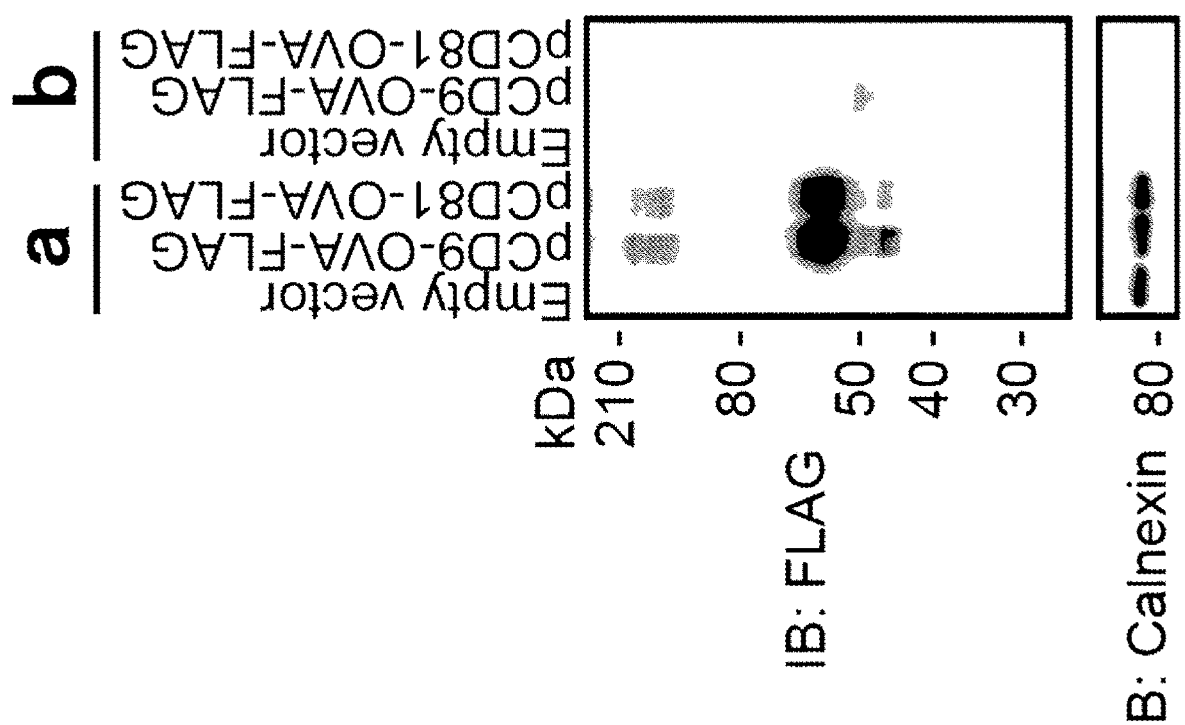
FIG. 6A Evaluation of immunological benefit of other exosome markers fused with OVA for DNA vaccine preparation. (A, B) An empty vector, pCD9-OVA-FL antigen, or CD81-OVA-FL antigen was transiently transfected into 293-F cells and 293T cells. Exosomes were purified from the cell supernatant after 48 days from transfection. (A) Cells and exosomes were analyzed by immunoblotting. (B) The OVA protein concentrations of the cells and supernatant were analyzed by ELISA. The labels a and b indicate the cell and exosome fractions, respectively.
Figure 6B:
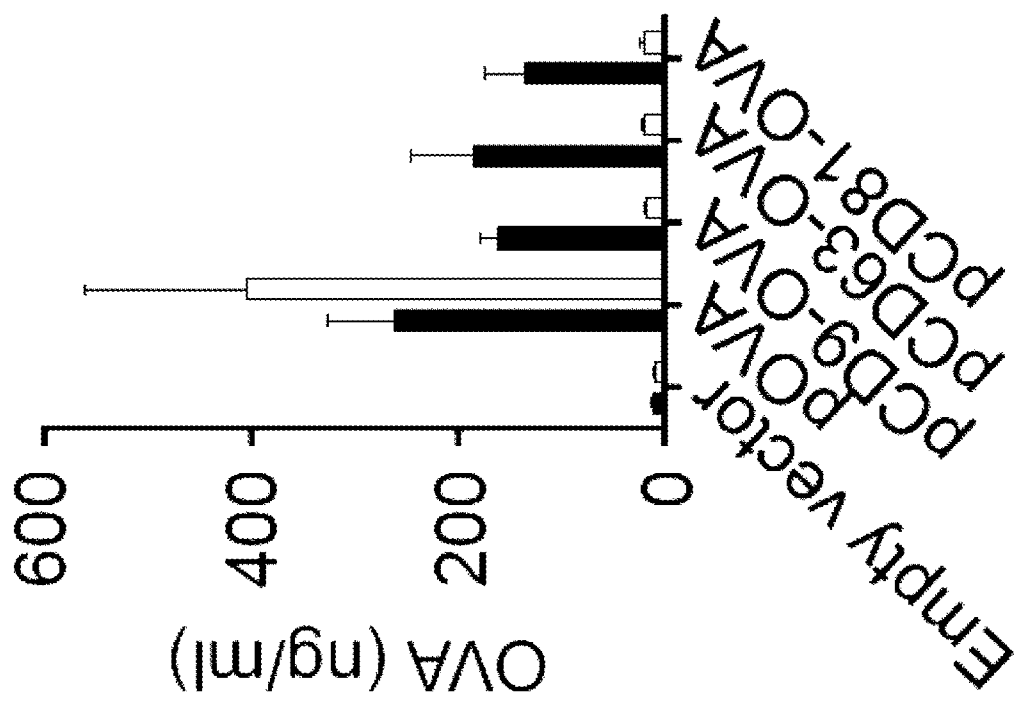
FIG. 6B Evaluation of immunological benefit of other exosome markers fused with OVA for DNA vaccine preparation. (A, B) An empty vector, pCD9-OVA-FL antigen, or CD81-OVA-FL antigen was transiently transfected into 293-F cells and 293T cells. Exosomes were purified from the cell supernatant after 48 days from transfection. (A) Cells and exosomes were analyzed by immunoblotting. (B) The OVA protein concentrations of the cells and supernatant were analyzed by ELISA. The black bars indicate cells and the white bars indicate supernatant.
Figure 6C:
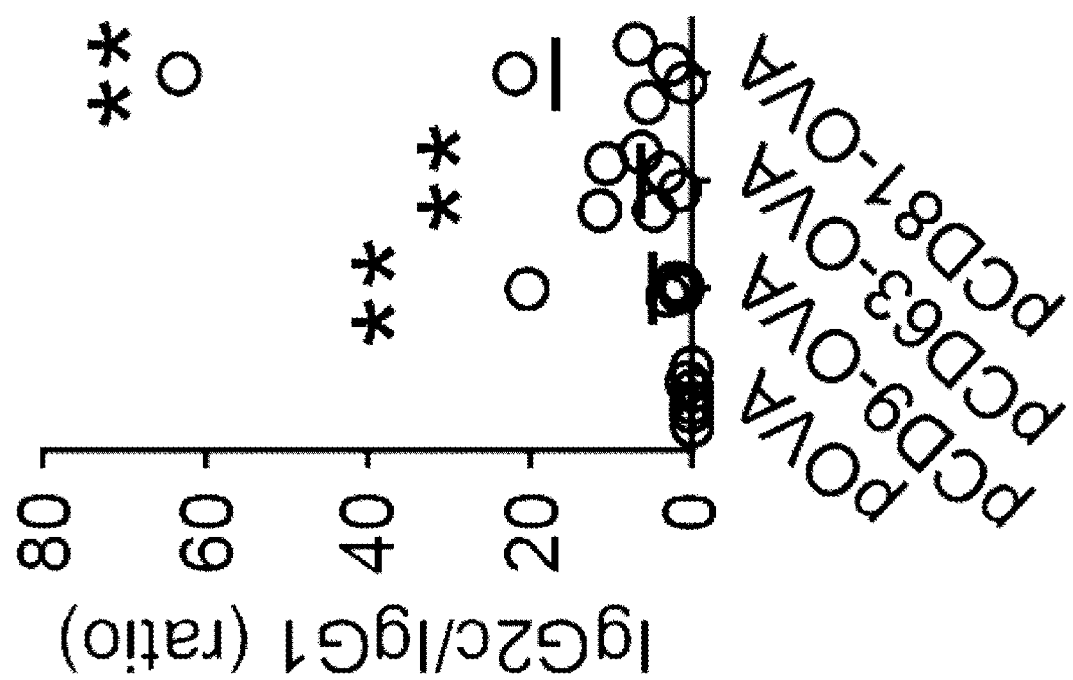
FIG. 6C C57BL/6J mice (n=6) were immunized by introducing pOVA, pCD9-OVA, pCD63-OVA, or CD81-OVA by intramuscular electroporation (50 μg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates $p<0.05$ and ** indicates $p<0.005$ (Mann-Whitney U test).
Figure 6D:
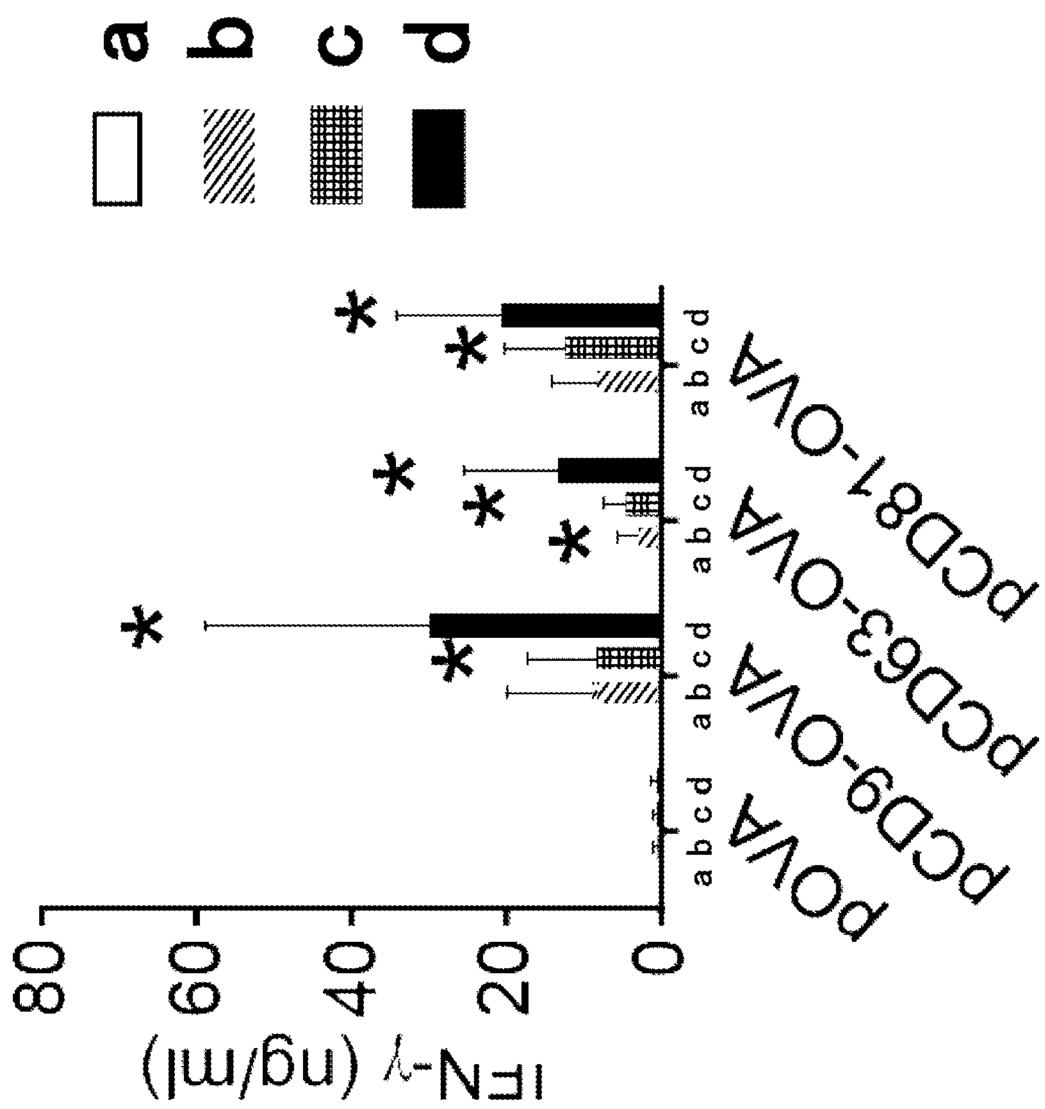
FIG. 6D C57BL/6J mice (n=6) were immunized by introducing pOVA, pCD9-OVA, pCD63-OVA, or CD81-OVA by intramuscular electroporation (50 μg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates $p<0.05$ and ** indicates $p<0.005$ (Mann-Whitney U test). The bar labels a, b, c, and d indicate the medium, $OVA_{257-264}$, $OVA_{323-339}$, and OVA, respectively.
Figure 6E:
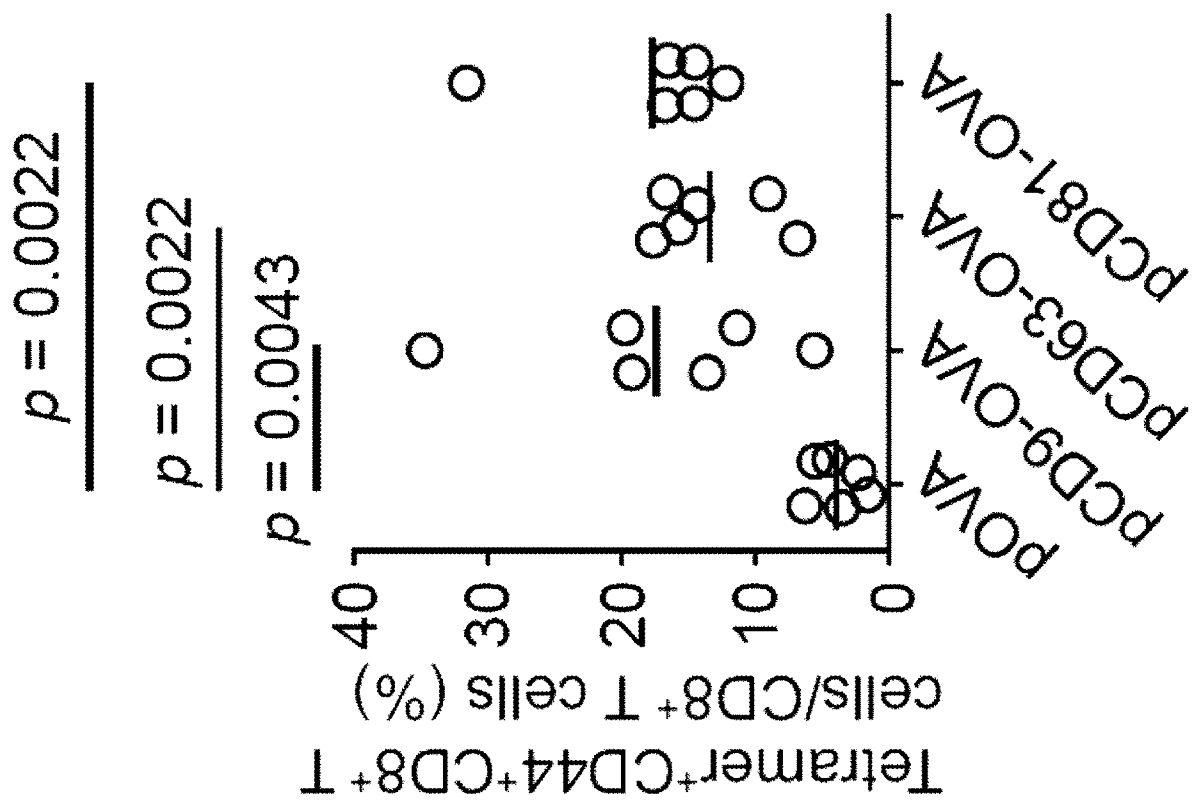
FIG. 6E C57BL/6J mice (n=6) were immunized by introducing pOVA, pCD9-OVA, pCD63-OVA, or CD81-OVA by intramuscular electroporation (50 μg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates $p<0.05$ and ** indicates $p<0.005$ (Mann-Whitney U test).

In addition to CD63-based fusion proteins, the inventors also prepared plasmid DNA encoding a CD9-OVA (pCD9-OVA) or CD81-OVA (pCD81-OVA) fusion protein. These plasmid DNAs also target the encoded antigen to exosomes (Thery, C., L. Zitvogel, and S. Amigorena. 2002. Nat Rev Immunol 2: 569-579) (Fujita, Y., N. Kosaka, J. Araya, K. Kuwano, and T. Ochiya. 2015. Trends in molecular medicine.) The inventors confirmed that both CD9-OVA proteins and CD81-OVA proteins are expressed in exosomes (FIGS. 6A and 6B). DNA vaccine inoculation with pCD9-OVA or pCD81-OVA resulted in a higher anti-OVA IgG2c/G1 ratio than vaccination with control pOVA. Furthermore, antigen specific $CD8^+$ T cell responses also increased, and the level thereof was equivalent to that of pCD63-OVA vaccination (FIGS. 6C to 6E).

The results indicate that antigen targeting to exosomes in DNA vaccine inoculation improves immunogenicity of a DNA vaccine, especially the $CD8^+$ T cell responses.

Figure 2D:
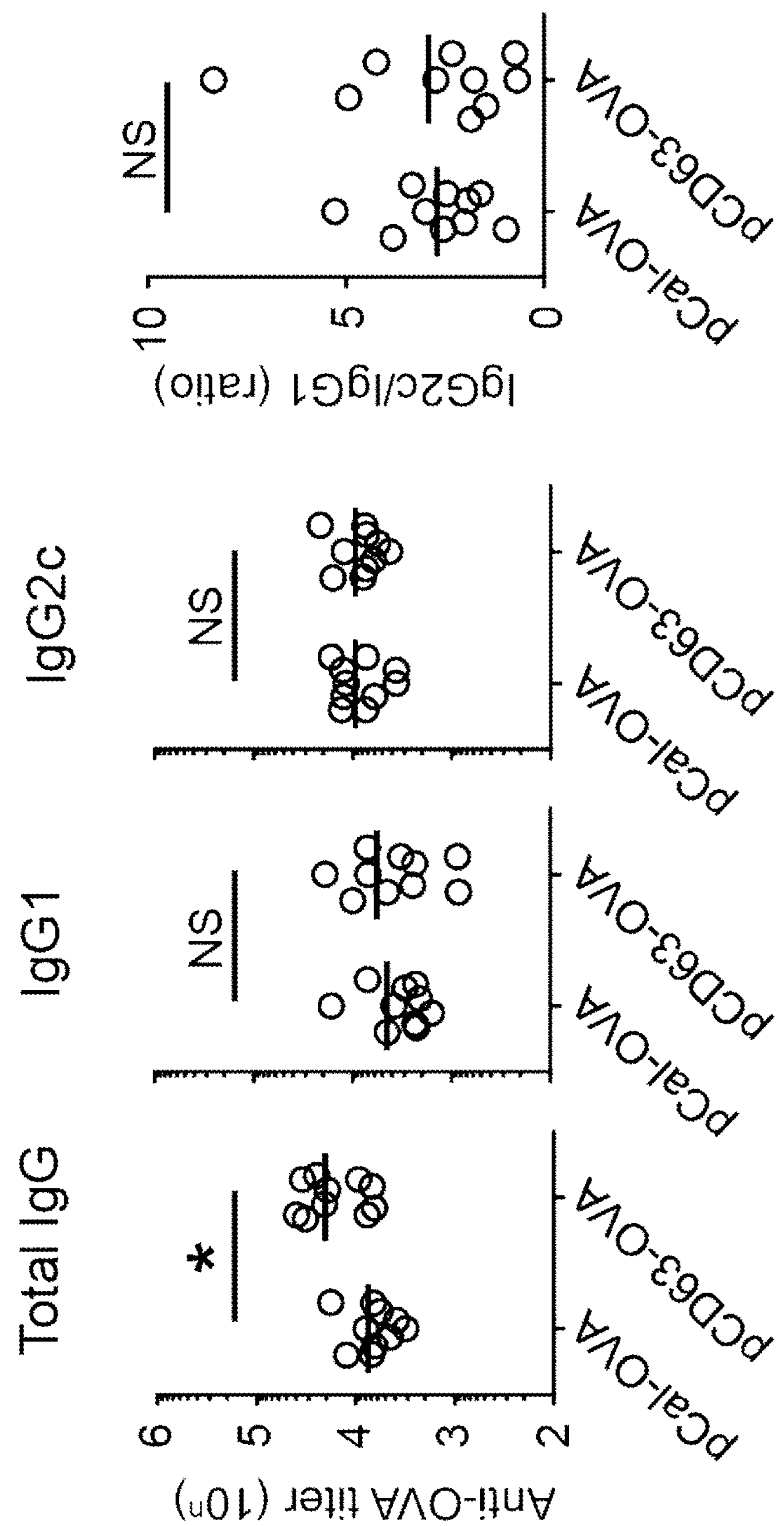
FIG. 2D The effect of antigen targeting to an exosome on immunogenicity of a DNA vaccine. C57BL/6J mice (n=10) were immunized by introducing pCal-OVA or pCD63-OVA by intramuscular electroporation (50 μg/mouse). On day 21 after immunization with these plasmids on day 0 and day 14, OVA specific IgG titer, OVA specific serum IgG1 titer, and OVA specific serum IgG2c titer were measured to monitor the ratio of OVA specific serum IgG2c to OVA specific serum IgG1. The leftmost graph shows the logarithmic OVA specific IgG titer (antibody OVA titer) for total IgG. Second and third graphs from the left show results of observing the same numerical value for IgG1 and IgG2c. The rightmost graph shows the ratio of OVA specific serum IgG2c to OVA specific serum IgG1 (IgG2c/IgG1). * indicates $p<0.05$ (Mann-Whitney U test). NS indicates that a statistically significant difference was not found.
Figure 2E:
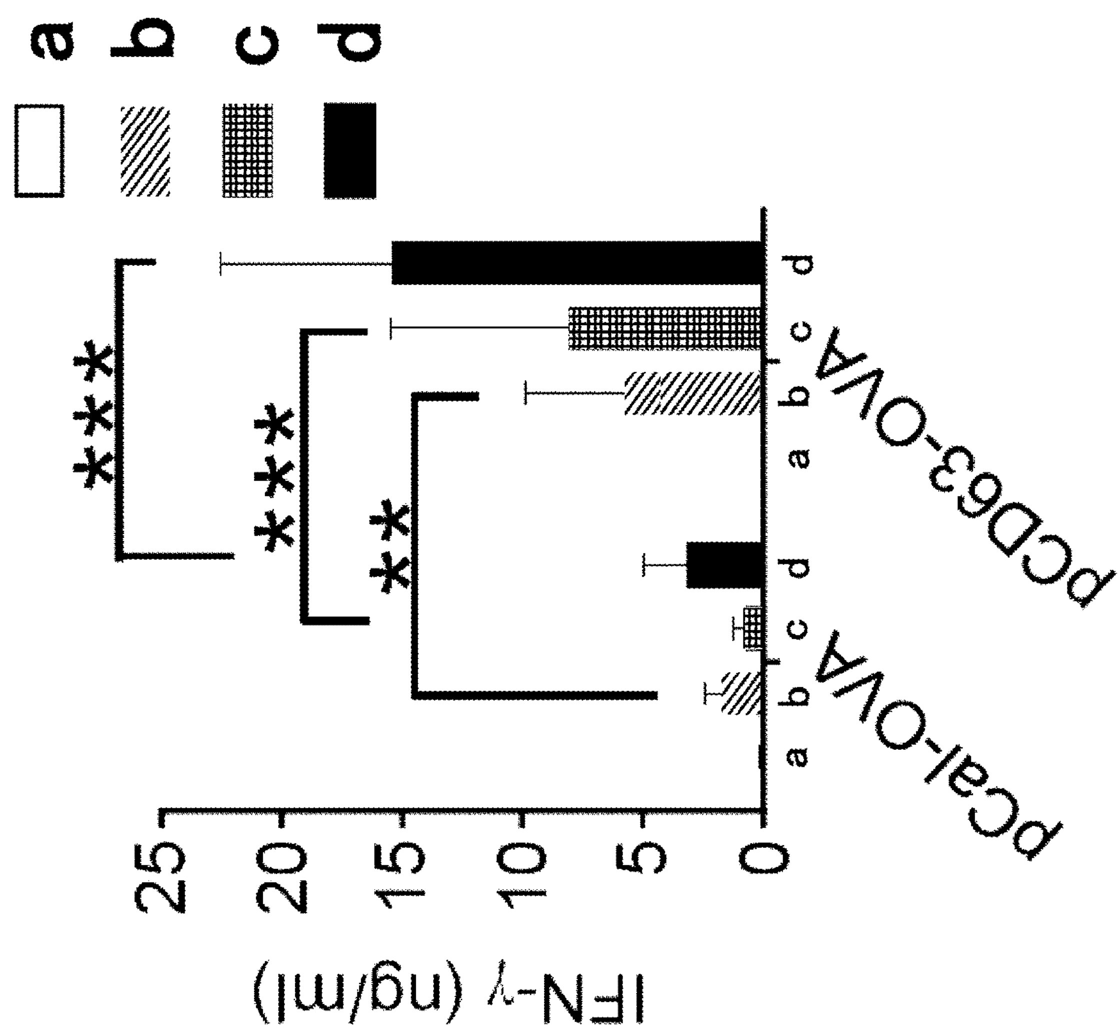
FIG. 2E The effect of antigen targeting to an exosome on immunogenicity of a DNA vaccine. C57BL/6J mice (n=10) were immunized by introducing pCal-OVA or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (F), and IFN-γ level induced in spenocytes by OVA, $OVA_{257-264}$, $OVA_{323-339}$, or a medium (E) were monitored. Data represents three independent experiments. The error bar represents the SD. * indicates $p<0.05$ and ** indicates $p<0.005$ (Mann-Whitney U test). For the bar labels, a, b, c, and d indicate medium, $OVA_{257-264}$, $OVA_{323-339}$, and OVA, respectively.
Figure 2F:
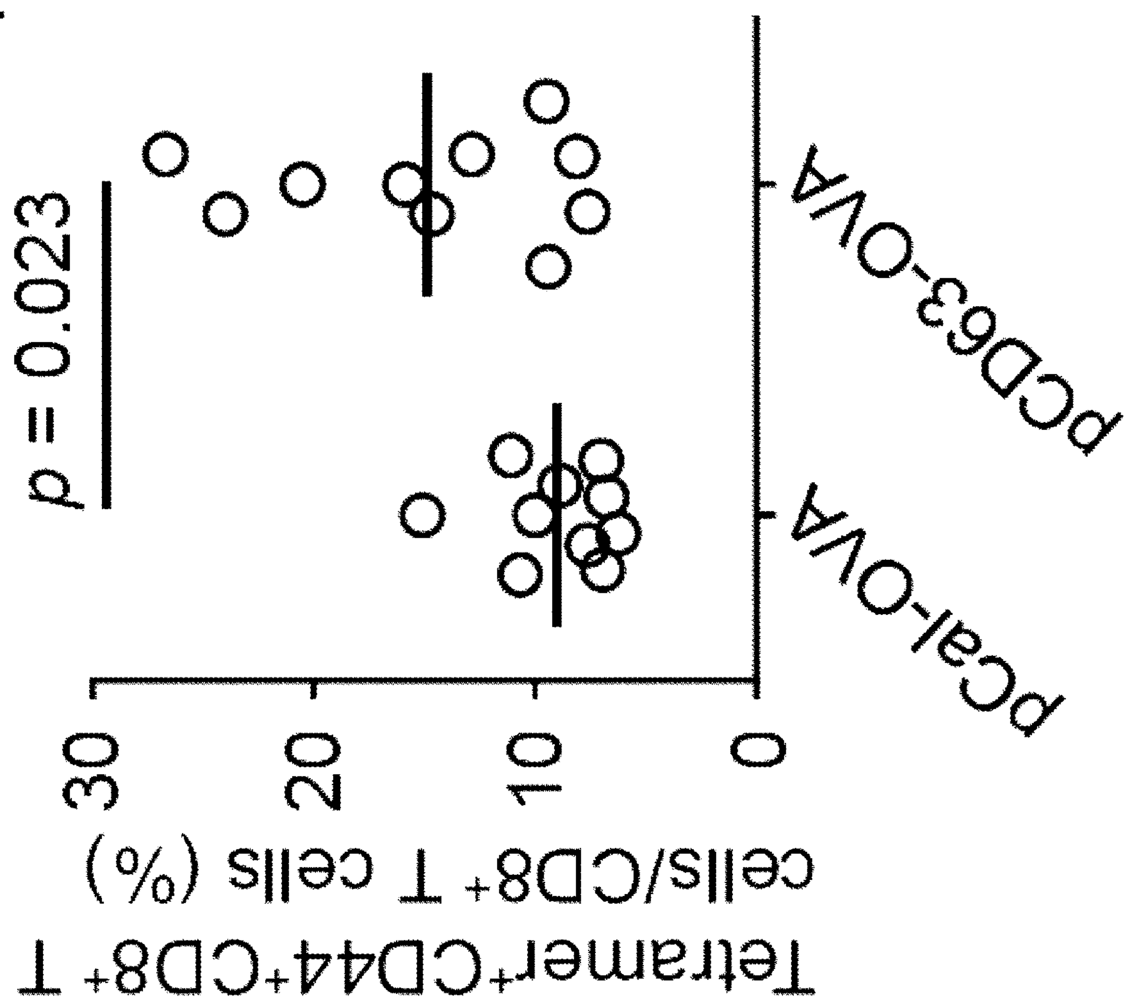
FIG. 2F The effect of antigen targeting to an exosome on immunogenicity of a DNA vaccine. C57BL/6J mice (n=10) were immunized by introducing pOVA, pCal-OVA, or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (F), and IFN-γ level induced in splenocytes by OVA, $OVA_{257-264}$, $OVA_{323-339}$, or a medium (E) were monitored. Data represents three independent experiments. * indicates $p<0.05$ (Mann-Whitney U test) (the p value of pCD63-OVA with respect to pCal-OVA was 0.023).

Exosome Targeting of Antigen is Important for Improving Immunogenicity of a DNA Vaccine Next, the inventors investigated whether the strategy to target the encoded antigen to exosomes is advantageous over an alternative strategy to promote T cell activation by DNA vaccine inoculation (e.g., targeting of an antigen to another plasma membrane such as endoplasmic reticulum). For this objective, the inventors compared the scale and type of immunogenicity of two plasmid DNAs encoding different fusion proteins: pCD63-OVA targeting exosomes and pCal-OVA targeting ER. Mice subjected to two DNA vaccine inoculations through imEPT by pCD63-OVA or pCal-OVA exhibited similar anti-OVA Ab titer and anti-OVA IgG2c/G1 ratio (FIG. 2D). However, mice that have been vaccinated with pCal-OVA exhibited higher frequency of $OVA_{257-264}$ specific $tetramer^+CD44^+CD8^+$ T cells than mice that have been vaccinated with pCD63-OVA (FIG. 2E). In addition, pCD63-OVA vaccinated mouse derived splenocytes produced a significantly higher amount of IFN-γ upon stimulation relative to pCal-OVA immunized mouse derived splenocytes (FIG. 2F). The results indicate that targeting of an antigen to the exosome membrane, not other membranes, is sufficient to improve the immunogenicity of a DNA vaccine.

CD63 does not Act as a Genetic Adjuvant for Co-Administered DNA Vaccine

Figure 3A:
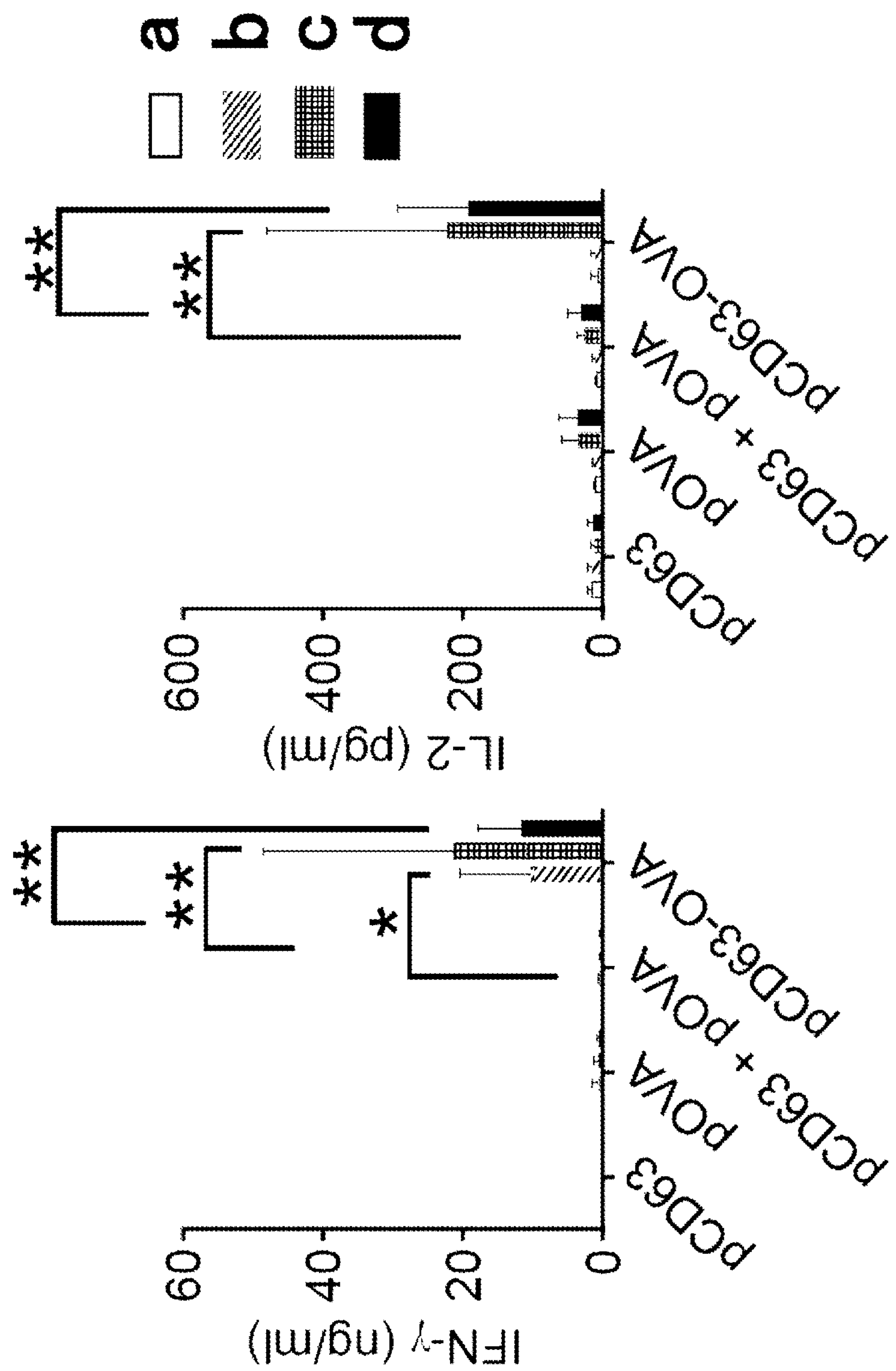
FIG. 3A Evaluation of CD63 expression plasmid as a gene adjuvant for a co-administered DNA vaccine. (A, B) C57BL/6J mice (n=5) were immunized by introducing pOVA, pCD63, pOVA+pCD63, or pCD63-OVA by intramuscular electroporation (50 μg/mouse). On day 21 after immunization with these plasmids on day 0 and day 14, IFN-γ or IL-2 level induced in splenocytes by OVA, $OVA_{257-264}$, $OVA_{323-339}$, or a medium (A) and the ratio of $CD8^+$ T cells recognized by an $OVA_{257-264}$ specific tetramer (B) were monitored. Data represents two independent experiments. The error bar represents the SD. * indicates $p<0.05$ and ** indicates $p<0.005$ (Mann-Whitney U test). For the bar labels, a, b, c, and d indicate medium, $OVA_{257-264}$, $OVA_{323-339}$, and OVA, respectively.
Figure 3B:
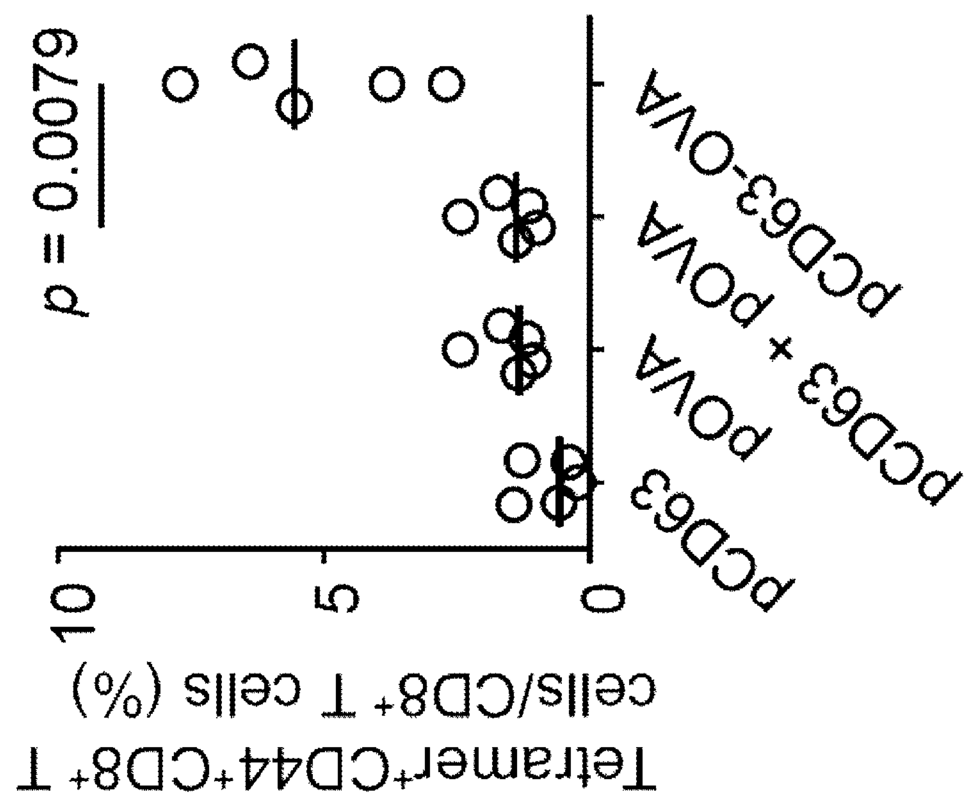
FIG. 3B Evaluation of CD63 expression plasmid as a gene adjuvant for a co-administered DNA vaccine. (A, B) C57BL/6J mice (n=5) were immunized by introducing pOVA, pCD63, pOVA+pCD63, or pCD63-OVA by intramuscular electroporation (50 μg/mouse). On day 21 after immunization with these plasmids on day 0 and day 14, IFN-γ or IL-2 level induced in splenocytes by OVA, $OVA_{257-264}$, $OVA_{323-339}$, or a medium (A) and the ratio of $CD8^+$ T cells recognized by an $OVA_{257-264}$ specific tetramer (B) were monitored. Data represents two independent experiments. The error bar represents the SD. * indicates $p<0.05$ and ** indicates $p<0.005$ (Mann-Whitney U test).

Since pCD63-OVA vaccines induce a potent $CD8^+$ T cell response (FIG. 2), the inventors investigated whether a plasmid DNA expressing CD63 acts as a genetic adjuvant for a DNA vaccine expressing OVA. In order to evaluate the potential adjuvant effect of CD63, mice were immunized with pOVA, pCD63, mixture of pOVA and pCD63, or pCD63-OVA. After 1 week from secondary immunization, OVA specific $CD4^+$ and $CD8^+$ T cell responses were not promoted in mice subjected to pCD63 together with pOVA relative to mice subjected to pOVA alone. However, mice that were vaccinated with pCD63-OVA exhibited a significant increase in OVA specific $CD4^+$ and $CD8^+$ T cell responses (FIGS. 3A and 3B). These results indicate that CD63 itself does not function as a genetic adjuvant unless conjugated to an OVA antigen as a fusion protein. Therefore, delivery of an antigen into or on an exosome can improve the immunogenicity of a DNA vaccine.

Targeting of an Antigen to an Exosome is Useful in a Tumor Vaccine

Figure 4A:
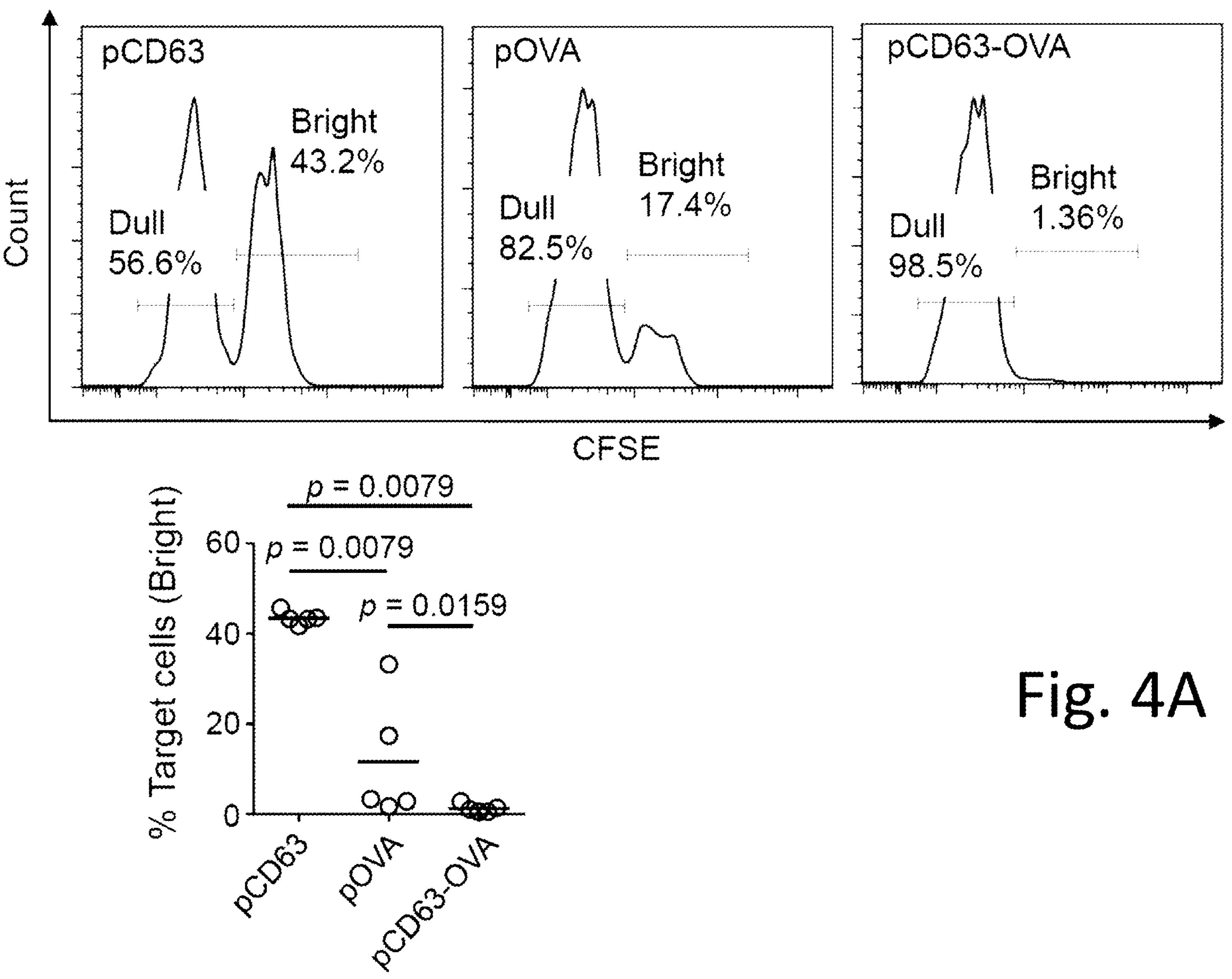
FIG. 4A The effect of antigen targeting to an exosome on prophylactic or therapeutic tumor vaccine. (A) An in vivo CTL assay was conducted after 7 days from DNA vaccine preparation using pOVA (n=5), pCD63-OVA (n=5), or pCD63 (n=5). Data represents two independent experiments. The horizontal axis of the top diagram depicts the logarithmic fluorescence intensity of CFSE, and the vertical axis indicates the cell count corresponding to the fluorescence intensity. In the bottom diagram, an experiment was conducted, where cells were stained with CFSE and cells with strong fluorescence intensity were killed by cytotoxic T cells to evaluate how much cytotoxic T cells are induced in mice by the ratio of killed cells. The bottom diagram shows the ratio of surviving cells with strong fluorescence intensity. The error bar represents the SD.
Figure 4B:
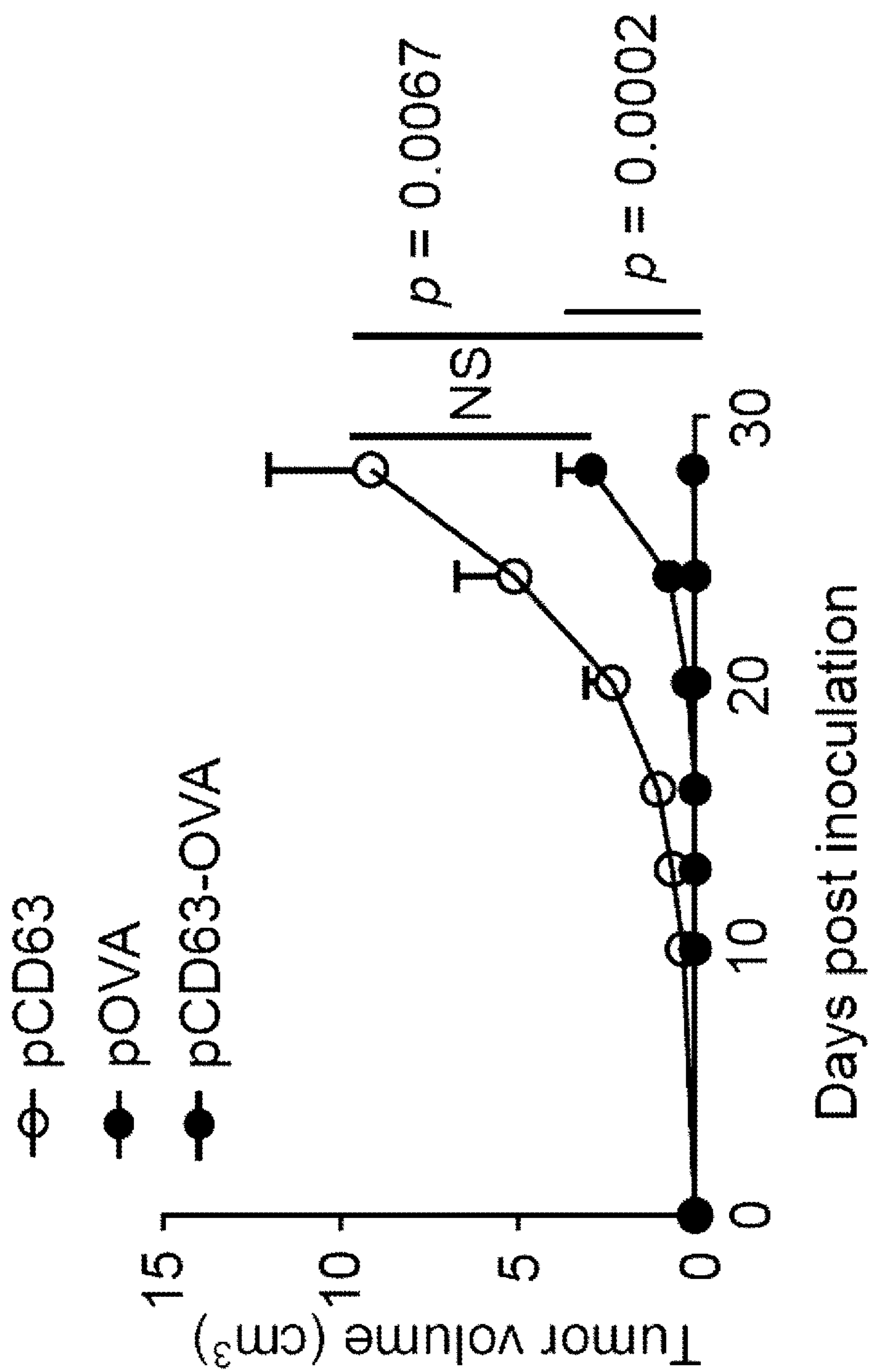
FIG. 4B (B) C57BL/6J mice (n=10) were immunized by introducing pOVA, pCD63, or pCD63-OVA by intramuscular electroporation (50 μg/mouse). 7 days after the last immunization, mice were inoculated with $1\times10^6$ E.G7 cells. Tumor growth was monitored thereafter for 28 days. Data represents two independent experiments. The error bar represents SEM.

Lastly, the inventors investigated whether a pCD63-OVA vaccine is applicable to a cancer vaccine and/or immunotherapy. Since a CTL response is important for the efficacy of a cancer vaccine, an in vivo CTL cytotoxicity assay was conducted to evaluate the level of functional $CD8^+$ T cell activity. Immunization of mice with pCD63-OVA significantly increased the OVA specific $CD8^+$ T cell mediated functional cytotoxicity relative to that induced by immunization with pOVA alone (FIG. 4A). In order to investigate whether pCD63-OVA can suppress tumor growth, explant syngeneic tumor models having E.G-7 cells, which are OVA overexpressing mouse lymphoma cells, were used. Mice were immunized with pCD63-OVA or another control plasmid DNA vaccine before seeding E.G-7 tumor cells. After seeding of tumor, tumor growth was suppressed significantly more in pCD63-OVA immunized mice compared to the control plasmid DNA immunized mice (FIG. 4B).

Figure 4C:
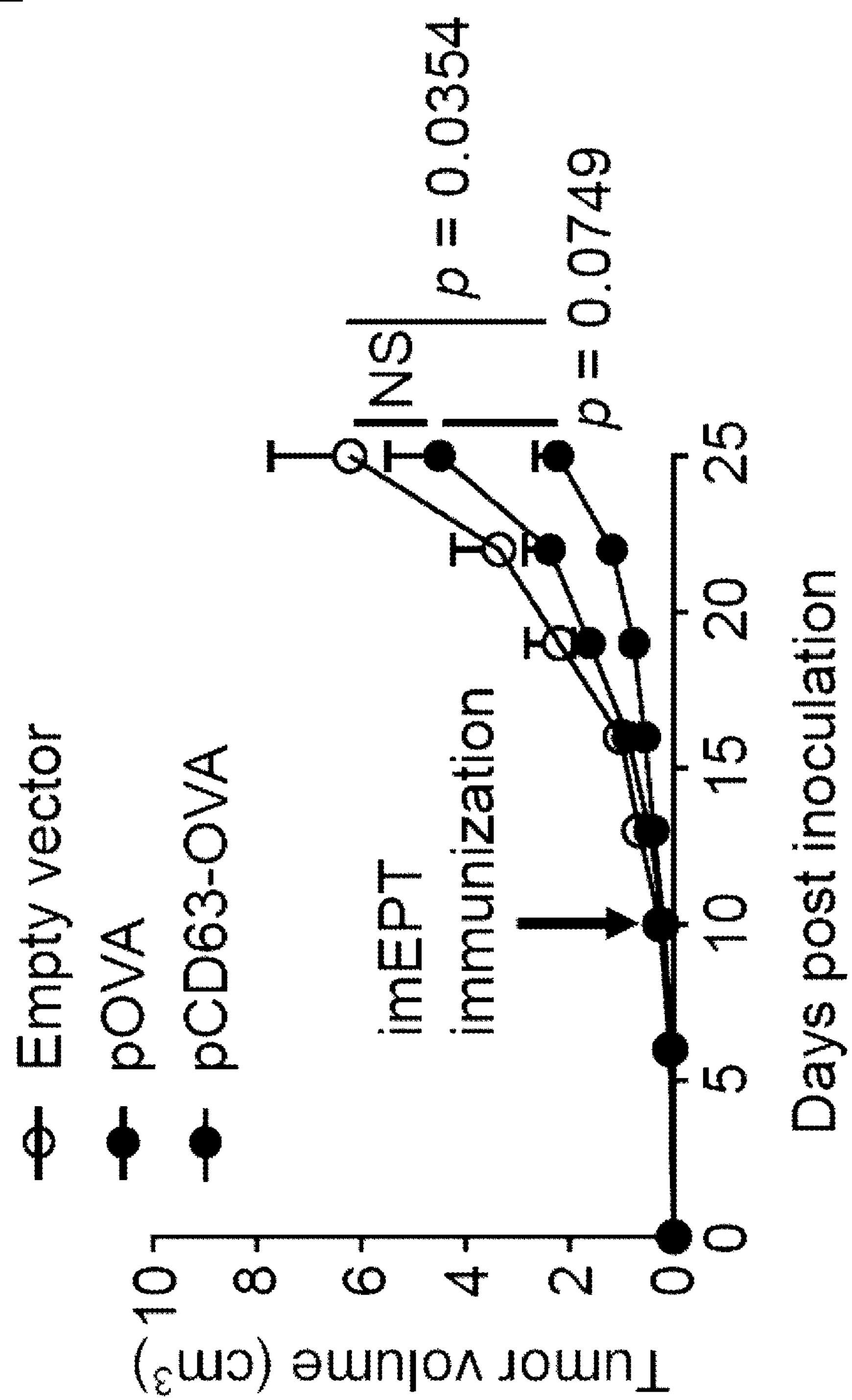
FIG. 4C (C) 10 days before the immunization, mice were inoculated with $1\times10^6$ E.G7 cells. 10 mice for each group were immunized with 50 μg of pOVA-FL antigen, pCD63-OVA-FL antigen, or an empty vector. Tumor growth was monitored thereafter for 25 days. Data represents three independent experiments. The error bar represents SEM.
Figure 4D:
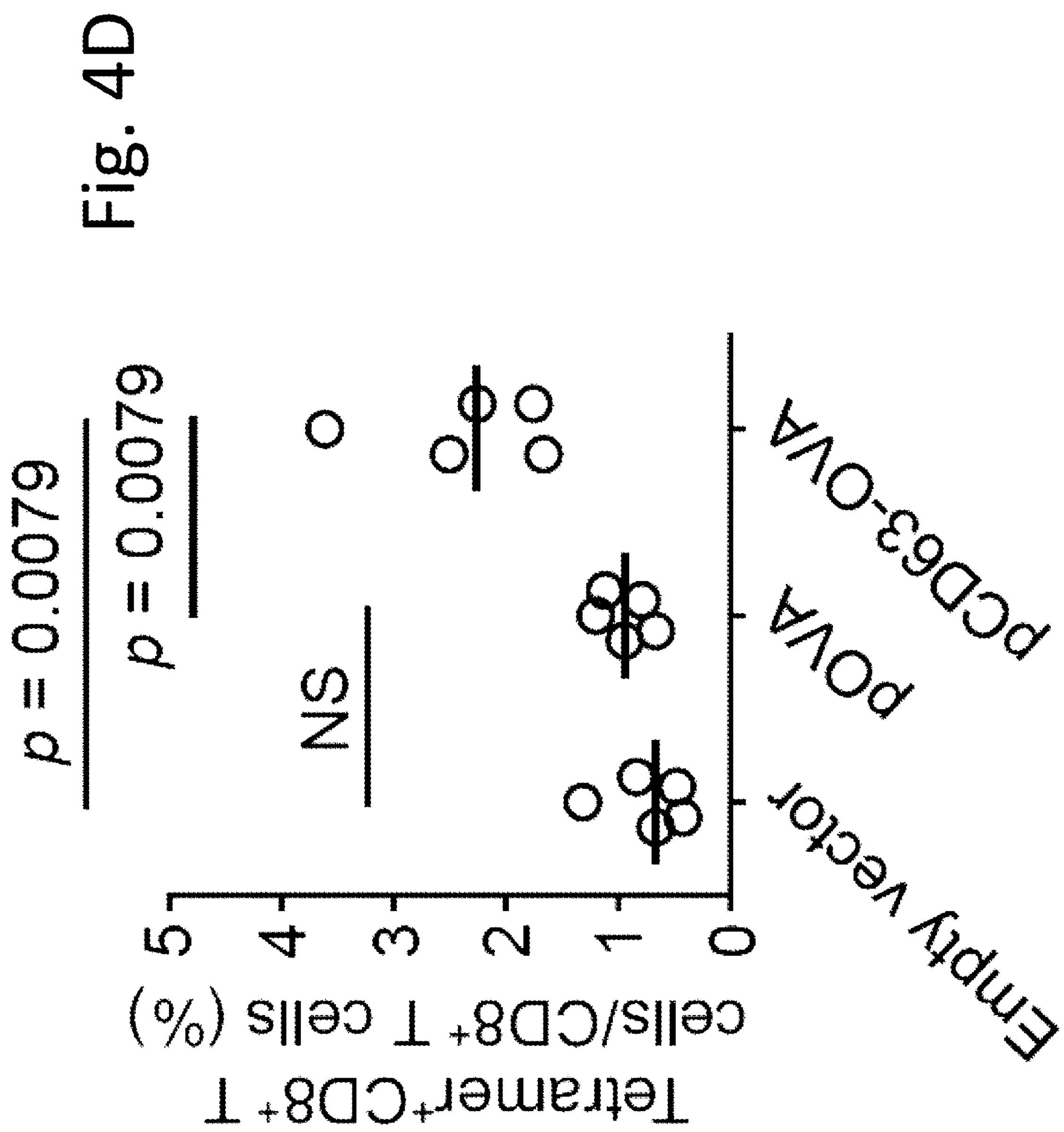
FIG. 4D (D) The ratio of $CD8^+$ T cells recognized by T cells recognized by an $OVA_{257-264}$ specific tetramer was monitored on day 25 after inoculation of E.G7 cells. Data represents two independent experiments. The error bar represents the SD.

In order to further evaluate the potential ability of pCD63-OVA to act as a therapeutic vaccine, mice were immunized with a DNA vaccine after 10 days from tumor seeding in the same E.G-7 tumor model. Mice immunized with pCD63-OVA exhibited significantly lower tumor growth than mice in other DNA vaccine inoculation groups (FIG. 4C). There was no statistically significant difference between pOVA and pCD63-OVA vaccination from the viewpoint of tumor suppression ($p=0.0749$), but a better tendency of controlled tumor growth can be clearly observed with pCD63-OVA vaccination relative to pOVA vaccination. The OVA specific $CD8^+$ T cell count increased by pCD63-OVA vaccination (FIG. 4D). These results indicate that targeting of an antigen to an exosome during DNA immunization can be a novel strategy for eliciting an antigen specific $CD8^+$ T cell response. In addition, this strategy can also be applicable for use in cancer vaccines.

(Discussion)

Both humoral and cell-mediated immune responses were induced by DNA vaccine inoculation in animal models. However, an immunological response to a DNA vaccine is often weaker than expected in humans. The study of the inventors demonstrated the efficacy of pCD63-OVA DNA vaccine inoculation and suggested that immunogenicity of a DNA vaccine can be improved by targeting an antigen to an exosome. The results in this Example suggest that: 1) pCD63-OVA vaccination successfully targets the encoded OVA antigen to a secreted exosome; 2) pCD63-OVA vaccination induces a potent type I immune response such as an antigen specific and functionally cytotoxic $CD8^+$ T cell response in vivo; and 3) pCD63-OVA vaccination suppresses explant syngeneic E.G-7 cell derived tumor growth in both prophylactic and therapeutic manner.

After DNA vaccine inoculation, stroma cells and DC at the injection site were directly transfected with a plasmid DNA (Herrada, A. A., et al., 2012. Hum Vaccin Immunother 8: 1682-1693.). The transfected cells then transcribed and translated the encoded antigen. The antigen was subsequently presented to T cells directly by DC or indirectly through stroma cells. This results in not only induction of $CD4^+$ Th1 cells specific to the encoded antigen, but also induction of $CD8^+$ T cells through an indirect mechanism of cross-presentation (Liu, M. A. 2003. 253: 402-410.) At the same time, a plasmid DNA is detected by an intracellular DNA sensor and acts as an exogenous adjuvant for DNA vaccine induced humoral and cell-mediated immune responses to an encoded antigen (Thery, C., et al., 2002. Nat Immunol 3: 1156-1162., Zitvogel, L., et al., 1998. Nat Med 4: 594-600.) Both the cellular immunological mechanism of DNA vaccine inoculation and immunological function of exosomes have been extensively studied in recent years (Gentili, M., et al. 2015. Science (New York, N.Y.) 349: 1232-1236.), while the role of exosomes in DNA vaccine induced immune responses have not been sufficiently studied. There are several previous reports of investigating the role of exosomes in immune response induction (Qazi, K. R., et al., 2009. Blood 113: 2673-2683., Cheng, Y., and J. S. Schorey. 2013. Eur J Immunol 43: 3279-3290), but the data of the inventors clearly demonstrated for the first time that a plasmid DNA encoding an antigen protein fused with CD63 increases the immunogenicity of a vaccine.

The most noteworthy feature of a plasmid DNA encoding a CD63-OVA fusion protein antigen is the ability to induce a potent $CD8^+$ T cell response. The increased $CD8^+$ T cell response to the encoded antigen can be attributed to exosome targeting of the encoded antigen via CD63. However, further research is required to confirm whether cross presentation of an antigen to a $CD8^+$ T cell via an exosome is present and whether this is important for a DNA vaccine induced $CD8^+$ T cell response. It is also conceivable that CD63 and other tested tetraspanins do not exclusively target exosomes, but similarly direct the encoded antigen to other plasma membranes. More evidence is required to elucidate the detailed mechanism of cross presentation that is required for a DNA vaccine to induce a $CD8^+$ T cell response.

E.G-7 tumor cells that express OVA proteins as a tumor antigen were used in the tumor model of the inventors. Previous reports suggested that growth of tumor cells expressing OVA is reduced by immunization with an OVA protein and an adjuvant or a DNA vaccine comprised of an OVA expressing plasmid DNA (Chamoto, K., et al., 2006. Cancer Res 66: 1809-1817., Teramoto, K., et al., 2003. Cancer Res 63: 7920-7925.) Other reports have already shown that exosomes can mediate $CD4^+$ and $CD8^+$ T cell dependent antitumor effects (Wolfers, J., et al., 2001. Nat Med 7: 297-303.) Meanwhile, the results of the inventors confirm these findings and demonstrate, for the first time as far as the inventors are aware, that growth of E.G-7 tumor cells can be further suppressed by DNA vaccine inoculation with pCD63-OVA targeting an encoded antigen to an exosome.

The OVA-specific $tetramer^+CD8^+$ T cell count in tumor transplanted mice significantly increased with DNA vaccine inoculation with pCD63-OVA (FIG. 4D). This indicates that it can be possible to overcome the resistance or depletion of tumor antigen specific $CD8^+$ T cells by vaccination with a DNA encoding a fusion protein of a tumor antigen and an exosome targeting molecule such as CD63, CD9, or CD81. However, it should be noted that these tetraspanin exosome marker proteins are also expressed in other plasma membranes. Therefore, potential contribution of other plasma membranes to the increased immunogenicity cannot be excluded. Since the low endosome specificity can also lead to an off-target effect from a fusion protein with tetraspanin, there are concerns about safety in clinical application.

DNA vaccines are approved and used in veterinary applications (Redding, L., and D. B. Weiner. 2009. Expert review of vaccines 8: 1251-1276.). In humans, DNA vaccines for many infectious diseases or cancer therapy are currently in clinical trials (Escudier, B., et al., 2005. J Transl Med 3: 10.; Morse, M. A., et al., 2005. J Transl Med 3: 9.; Viaud, S., et al., 2009. DPLoS One 4: e4942.; Viaud, S., et al., 2010. Cancer Res 70: 1281-1285. 38-41). These vaccines and vaccine candidates utilize various strategies for improving the low immunogenicity of DNA vaccines. The results of the inventors suggest that strategies for targeting an encoded antigen to an exosome through fusion of an antigen and an exosome marker (e.g., CD63) can be another feasible method for improving the immunogenicity of a DNA vaccine. This strategy is suitable especially for increasing the $CD8^+$ T cell response to an encoded antigen. The finding of the inventors provides insight into how the immunogenicity and efficacy of DNA vaccines can be improved. The findings of the inventors also improves the biological and immunological understanding of how an antigen encoded in DNA in a DNA vaccine is delivered/processed by the immune system to provide an antigen specific immune response.

(Conclusion)

In view of the above, the nucleic acid construct of the invention was shown to be able to improve immunogenicity of a vaccine DNA, enhance immune responses, enhance T cell responses, and achieve an effect of treating or preventing cancer and the like.

Example 2: Formulation Example

A formulation can be manufactured by the following manufacturing methods.

(Ex. 1) A suitable volume of saline can be directly added to a suitable amount of lyophilized vaccine DNA to prepare an injectable solution formulation.

(Ex. 2) A suitable volume of isotonizing solution/5% glucose solution can be added to a suitable amount of lyophilized vaccine DNA to prepare an injectable solution formulation.

(Ex. 3) A suitable volume of electrolyte corrective solution/Otsuka sodium chloride injection 10% and the like are added to a suitable amount of vaccine DNA dissolved in water to prepare an injectable solution formulation adjusted to a 0.9% NaCl concentration.

(Ex. 4) A suitable amount of vaccine DNA dissolved in water can be lyophilized to prepare a lyophilized formulation of vaccine DNA sodium salt.

Ex. 1, 3, and 4 are preferred. Ex. 2 can also be used depending on the administration method.

REFERENCE DOCUMENTS

The following are documents referenced in the Examples. The list of the following document does not constitute acquiescence that they are prior art to the present invention.

1. Donnelly, J. J., B. Wahren, and M. A. Liu. 2005. J Immunol 175: 633-639.
2. Gurunathan, S., D. M. Klinman, and R. A. Seder. 2000. Annual review of immunology 18: 927-974.
3. Kutzler, M. A., and D. B. Weiner. 2008. Nat Rev Genet 9: 776-788.
4. Ulmer, J. B., R. R. Deck, C. M. DeWitt, A. Friedman, J. J. Donnelly, and M. A. Liu. 1994. Vaccine 12: 1541-1544.
5. Tang, D. C., M. DeVit, and S. A. Johnston. 1992. Nature 356: 152-154.
6. Reed, S. G., M. T. Orr, and C. B. Fox. 2013. Nat Med 19: 1597-1608.
7. Thery, C., L. Zitvogel, and S. Amigorena. 2002. Nat Rev Immunol 2: 569-579.
8. Simons, M., and G. Raposo. 2009. Curr Opin Cell Biol 21: 575-581.
9. Milane, L., A. Singh, G. Mattheolabakis, M. Suresh, and M. M. Amiji. 2015. official journal of the Controlled Release Society.
10. Poutsiaka, D. D., D. D. Taylor, E. M. Levy, and P. H. Black. 1985. J Immunol 134: 145-150.
11. Robbins, P. D., and A. E. Morelli. 2014. Nat Rev Immunol 14: 195-208.
12. Bobrie, A., M. Colombo, G. Raposo, and C. Thery. 2011. Traffic 12: 1659-1668.
13. Montecalvo, A., A. T. Larregina, W. J. Shufesky, D. B. Stolz, M. L. Sullivan, J. M. Karlsson, C. J. Baty, G. A. Gibson, G. Erdos, Z. Wang, J. Milosevic, O. A. Tkacheva, S. J. Divito, R. Jordan, J. Lyons-Weiler, S. C. Watkins, and A. E. Morelli. 2012. Blood 119: 756-766.
14. Raposo, G., H. W. Nijman, W. Stoorvogel, R. Liejendekker, C. V. Harding, C. J. Melief, and H. J. Geuze. 1996. J Exp Med 183: 1161-1172.
15. Jounai, N., K. Kobiyama, M. Shiina, K. Ogata, K. J. Ishii, and F. Takeshita. 2011. J Immunol 186: 1646-1655.
16. Nagata, T., T. Higashi, T. Aoshi, M. Suzuki, M. Uchijima, and Y. Koide. 2001. Vaccine 20: 105-114.
17. Thery, C., S. Amigorena, G. Raposo, and A. Clayton. 2006. Current protocols in cell biology/editorial board, Juan S. Bonifacino . . . [et al.] Chapter 3: Unit 3.22.
18. van der Vlist, E. J., E. N. Nolte-'t Hoen, W. Stoorvogel, G. J. Arkesteijn, and M. H. Wauben. 2012. Nature protocols 7: 1311-1326.
19. Takeshita, F., T. Tanaka, T. Matsuda, M. Tozuka, K. Kobiyama, S. Saha, K. Matsui, K. J. Ishii, J Virol 80: 6218-6224.
20. Onishi, M., K. Ozasa, K. Kobiyama, K. Ohata, M. Kitano, K. Taniguchi, T. Homma, M. Kobayashi, A. Sato, Y. Katakai, Y. Yasutomi, E. Wijaya, Y. Igarashi, N. Nakatsu, W. Ise, T. Inoue, H. Yamada, A. Vandenbon, D. M. Standley, T. Kurosaki, C. Coban, T. Aoshi, E. Kuroda, and K. J. Ishii. 2015. J Immunol 194: 2673-2682.
21. Kobiyama, K., T. Aoshi, H. Narita, E. Kuroda, M. Hayashi, K. Tetsutani, S. Koyama, S. Mochizuki, K. Sakurai, Y. Katakai, Y. Yasutomi, S. Saijo, Y. Iwakura, S. Akira, C. Coban, and K. J. Ishii. 2014. Proc Natl Acad Sci USA 111: 3086-3091.
22. Wolfers, J., A. Lozier, G. Raposo, A. Regnault, C. Thery, C. Masurier, C. Flament, S. Pouzieux, F. Faure, T. Tursz, E. Angevin, S. Amigorena, and L. Zitvogel. 2001. Nat Med 7: 297-303.
23. Qazi, K. R., U. Gehrmann, E. Domange Jordo, M. C. Karlsson, and S. Gabrielsson. 2009. Blood 113: 2673-2683.
24. Pols, M. S., and J. Klumperman. 2009. Experimental cell research 315: 1584-1592.
25. Baietti, M. F., Z. Zhang, E. Mortier, A. Melchior, G. Degeest, A. Geeraerts, Y. Ivarsson, F. Depoortere, C. Coomans, E. Vermeiren, P. Zimmermann, and G. David. 2012. Nat Cell Biol 14: 677-685.
26. Gross, J. C., V. Chaudhary, K. Bartscherer, and M. Boutros. 2012. Nat Cell Biol 14: 1036-1045.
27. Lasser, C., V. S. Alikhani, K. Ekstrom, M. Eldh, P. T. Paredes, A. Bossios, M. Sjostrand, S. Gabrielsson, J. Lotvall, and H. Valadi. 2011. J Transl Med 9: 9.
28. Fujita, Y., N. Kosaka, J. Araya, K. Kuwano, and T. Ochiya. 2015. Trends in molecular medicine.
29. Herrada, A. A., N. Rojas-Colonelli, P. Gonzalez-Figueroa, J. Roco, C. Oyarce, M. A. Ligtenberg, and A. Lladser. 2012. Hum Vaccin Immunother 8: 1682-1693.
30. Liu, M. A. 2003. Journal of internal medicine 253: 402-410.
31. Thery, C., L. Duban, E. Segura, P. Veron, O. Lantz, and S. Amigorena. 2002. Nat Immunol 3: 1156-1162.
32. Zitvogel, L., A. Regnault, A. Lozier, J. Wolfers, C. Flament, D. Tenza, P. Ricciardi-Castagnoli, G. Raposo, and S. Amigorena. 1998. Nat Med 4: 594-600.
33. Gentili, M., J. Kowal, M. Tkach, T. Satoh, X. Lahaye, C. Conrad, M. Boyron, B. Lombard, S. Durand, G. Kroemer, D. Loew, M. Dalod, C. Thery, and N. Manel. 2015. Science (New York, N.Y.) 349: 1232-1236.
34. Cheng, Y., and J. S. Schorey. 2013. *Mycobacterium tuberculosis* infection. Eur J Immunol 43: 3279-3290.
35. Chamoto, K., D. Wakita, Y. Narita, Y. Zhang, D. Noguchi, H. Ohnishi, T. Iguchi, T. Sakai, H. Ikeda, and T. Nishimura. 2006. Cancer Res 66: 1809-1817.

36. Teramoto, K., K. Kontani, Y. Ozaki, S. Sawai, N. Tezuka, T. Nagata, S. Fujino, Y. Itoh, O. Taguchi, Y. Koide, T. Asai, I. Ohkubo, and K. Ogasawara. 2003. Cancer Res 63: 7920-7925.

37. Redding, L., and D. B. Weiner. 2009. Expert review of vaccines 8: 1251-1276.

38. Escudier, B., T. Dorval, N. Chaput, F. Andre, M. P. Caby, S. Novault, C. Flament, C. Leboulaire, C. Borg, S. Amigorena, C. Boccaccio, C. Bonnerot, O. Dhellin, M. Movassagh, S. Piperno, C. Robert, V. Serra, N. Valente, J. B. Le Pecq, A. Spatz, O. Lantz, T. Tursz, E. Angevin, and L. Zitvogel. 2005. J Transl Med 3: 10.

39. Morse, M. A., J. Garst, T. Osada, S. Khan, A. Hobeika, T. M. Clay, N. Valente, R. Shreeniwas, M. A. Sutton, A. Delcayre, D. H. Hsu, J. B. Le Pecq, and H. K. Lyerly. 2005. J Transl Med 3: 9.

40. Viaud, S., M. Terme, C. Flament, J. Taieb, F. Andre, S. Novault, B. Escudier, C. Robert, S. Caillat-Zucman, T. Tursz, L. Zitvogel, and N. Chaput. 2009. PLoS One 4: e4942.

41. Viaud, S., C. Thery, S. Ploix, T. Tursz, V. Lapierre, O. Lantz, L. Zitvogel, and N. Chaput. 2010. Cancer Res 70: 1281-1285.

(Note)

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein.

INDUSTRIAL APPLICABILITY

The present invention can be utilized in any industry that is associated with DNA vaccines, such as the vaccine industry and pharmaceutical industry.

[Sequence Listing Free Text]

SEQ ID NO: 1: nucleic acid sequence of human CD63, NM_001040034

SEQ ID NO: 2: amino acid sequence of human CD63, NP_001244318

SEQ ID NO: 3: nucleic acid sequence of mouse CD63, NM_001042580

SEQ ID NO: 4: amino acid sequence of mouse CD63, NP_001036045

SEQ ID NO: 5: nucleic acid sequence of human CD9, NM_001769

SEQ ID NO: 6: amino acid sequence of human CD9, NP_001760

SEQ ID NO: 7: nucleic acid sequence of mouse CD9, NM_007657

SEQ ID NO: 8: amino acid sequence of mouse CD9, NP_031683

SEQ ID NO: 9: nucleic acid sequence of human CD81, NM_001297649

SEQ ID NO: 10: amino acid sequence of human CD81, NP_001284578

SEQ ID NO: 11: nucleic acid sequence of mouse CD81, NM_133655

SEQ ID NO: 12: amino acid sequence of mouse CD81, NP_598416

SEQ ID NO: 13: nucleic acid sequence of calnexin used in the Examples (mouse)

SEQ ID NO: 14: amino acid sequence of calnexin used in the Examples (mouse)

SEQ ID NO: 15: nucleic acid sequence of OVA used in the Examples, V00383.1

SEQ ID NO: 16: amino acid sequence of OVA used in the Examples, CAA23682.1

The invention claimed is:

1. A method of enhancing an immune response in a subject, comprising administering to the subject an effective amount of a composition that comprises at least one selected from the group of: (a) a nucleic acid construct comprising a first nucleic acid sequence encoding an exosome marker protein and a second nucleic acid sequence encoding a vaccine antigen, wherein the exosome marker protein and the vaccine antigen are expressed in a fused form; (b) a protein in a form of a vaccine antigen protein fused with an exosome marker protein so that the fused protein is present in an exosome; and (c) an exosome comprising a vaccine antigen protein and an exosome marker protein in a fused form, wherein the exosome is an extracellular membrane vesicle.

2. The method of claim 1, wherein the exosome marker protein is a protein that is present in a membrane of an exosome.

3. The method of claim 1, wherein the exosome marker protein belongs to the tetraspanin family.

4. The method of claim 1, wherein the exosome marker protein is selected from the group consisting of CD63, CD81, CD9, CD31, HLA-G, TSG101, Rab5b, and ALIX.

5. The method of claim 1, wherein the exosome marker protein is selected from the group consisting of CD63, CD81, and CD9.

6. The method of claim 1, wherein the antigen is selected from a cancer antigen and a viral antigen.

7. The method of claim 1, wherein the nucleic acid construct is a plasmid DNA.

8. The method of claim 1, wherein the immune response is Th1-type immunity induction.

9. The method of claim 1, wherein the composition comprises (a) the nucleic acid construct comprising the first nucleic acid sequence encoding the exosome marker protein and the second nucleic acid sequence encoding a vaccine antigen.

10. The method of claim 1, wherein the composition comprises (b) the protein in the form of the vaccine antigen protein fused with the exosome marker protein.

11. The method of claim 1, wherein the composition comprises (c) the exosome comprising the vaccine antigen protein and the exosome marker protein in the fused form.

* * * * *

SEQUENCE LISTING

```
<160> NUMBER OF SEQ ID NOS: 16

<210> SEQ ID NO 1
<211> LENGTH: 1025
<212> TYPE: DNA
<213> ORGANISM: Homo sapiens
<220> FEATURE:
<221> NAME/KEY: CDS
<222> LOCATION: (186)..(896)

<400> SEQUENCE: 1

cagctgttac cgcgtcacat gagggaggcc ggcggccact cggcggggga ggggaccgtg      60

gctggagccc ggggcggggc cgcgcggcag gcggggcggg agccgggggg cgcagctaga     120

gagccccgga gccgcggcgg gagaggaacg cgcagccagc cttgggaagc ccaggcccgg     180

cagcc atg gcg gtg gaa gga gga atg aaa tgt gtg aag ttc ttg ctc tac     230
      Met Ala Val Glu Gly Gly Met Lys Cys Val Lys Phe Leu Leu Tyr
      1               5                   10                  15

gtc ctc ctg ctg gcc ttt tgc gcc tgt gca gtg gga ctg att gcc gtg       278
Val Leu Leu Leu Ala Phe Cys Ala Cys Ala Val Gly Leu Ile Ala Val
                20                  25                  30

ggt gtc ggg gca cag ctt gtc ctg agt cag acc ata atc cag ggg gct       326
Gly Val Gly Ala Gln Leu Val Leu Ser Gln Thr Ile Ile Gln Gly Ala
            35                  40                  45

acc cct ggc tct ctg ttg cca gtg gtc atc atc gca gtg ggt gtc ttc       374
Thr Pro Gly Ser Leu Leu Pro Val Val Ile Ile Ala Val Gly Val Phe
```

```
        50                  55                  60

ctc ttc ctg gtg gct ttt gtg ggc tgc tgc ggg gcc tgc aag gag aac      422
Leu Phe Leu Val Ala Phe Val Gly Cys Cys Gly Ala Cys Lys Glu Asn
    65                  70                  75

tat tgt ctt atg atc acg ttt gcc atc ttt ctg tct ctt atc atg ttg      470
Tyr Cys Leu Met Ile Thr Phe Ala Ile Phe Leu Ser Leu Ile Met Leu
80                  85                  90                  95

gtg gag gtg gcc gca gcc att gct ggc tat gtg ttt aga gat aag gtg      518
Val Glu Val Ala Ala Ala Ile Ala Gly Tyr Val Phe Arg Asp Lys Val
                100                 105                 110

atg tca gag ttt aat aac aac ttc cgg cag cag atg gag aat tac ccg      566
Met Ser Glu Phe Asn Asn Asn Phe Arg Gln Gln Met Glu Asn Tyr Pro
            115                 120                 125

aaa aac aac cac act gct tcg atc ctg gac agg atg cag gca gat ttt      614
Lys Asn Asn His Thr Ala Ser Ile Leu Asp Arg Met Gln Ala Asp Phe
        130                 135                 140

aag tgc tgt ggg gct gct aac tac aca gat tgg gag aaa atc cct tcc      662
Lys Cys Cys Gly Ala Ala Asn Tyr Thr Asp Trp Glu Lys Ile Pro Ser
    145                 150                 155

atg tcg aag aac cga gtc ccc gac tcc tgc tgc att aat gtt act gtg      710
Met Ser Lys Asn Arg Val Pro Asp Ser Cys Cys Ile Asn Val Thr Val
160                 165                 170                 175

ggc tgt ggg att aat ttc aac gag aag gcg atc cat aag gag ggc tgt      758
Gly Cys Gly Ile Asn Phe Asn Glu Lys Ala Ile His Lys Glu Gly Cys
                180                 185                 190

gtg gag aag att ggg ggc tgg ctg agg aaa aat gtg ctg gtg gta gct      806
Val Glu Lys Ile Gly Gly Trp Leu Arg Lys Asn Val Leu Val Val Ala
            195                 200                 205

gca gca gcc ctt gga att gct ttt gtt ttg gga att gtc ttt gcc tgc      854
Ala Ala Ala Leu Gly Ile Ala Phe Val Leu Gly Ile Val Phe Ala Cys
        210                 215                 220

tgc ctc gtg aag agt atc aga agt ggc tac gag gtg atg tag              896
Cys Leu Val Lys Ser Ile Arg Ser Gly Tyr Glu Val Met
    225                 230                 235

gggtctggtc tcctcagcct cctcatctgg gggagtggaa tagtatcctc caggtttttc    956

aattaaacgg attatttttt cagaccgaaa agagatggtc tgagtttgtc ttagaaaaaa   1016

aaaaaaaaa                                                           1025


<210> SEQ ID NO 2
<211> LENGTH: 236
<212> TYPE: PRT
<213> ORGANISM: Homo sapiens

<400> SEQUENCE: 2

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
```

```
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190

Glu Lys Ile Gly Gly Trp Leu Arg Lys Asn Val Leu Val Val Ala Ala
        195                 200                 205

Ala Ala Leu Gly Ile Ala Phe Val Leu Gly Ile Val Phe Ala Cys Cys
    210                 215                 220

Leu Val Lys Ser Ile Arg Ser Gly Tyr Glu Val Met
225                 230                 235


<210> SEQ ID NO 3
<211> LENGTH: 959
<212> TYPE: DNA
<213> ORGANISM: Mus musculus
<220> FEATURE:
<221> NAME/KEY: CDS
<222> LOCATION: (146)..(862)

<400> SEQUENCE: 3

agtaagcaac tcaaggcaga aggagctgcg gagaaaagga caaagttcag gttaggagtg      60

taaggccggt cggtcctatc tgagcttttt acaacagttc cttctgtgaa ccaccagcgg     120

cacacgggag aaaggcccaa cagcc atg gcg gtg gaa gga gga atg aag tgt       172
                            Met Ala Val Glu Gly Gly Met Lys Cys
                            1               5

gtc aag ttt ttg ctc tac gtt ctc ctg ctg gcc ttc tgc gcc tgt gca       220
Val Lys Phe Leu Leu Tyr Val Leu Leu Leu Ala Phe Cys Ala Cys Ala
10                  15                  20                  25

gtg gga ttg atc gcc att ggt gta gcg gtt cag gtt gtc ttg aag cag       268
Val Gly Leu Ile Ala Ile Gly Val Ala Val Gln Val Val Leu Lys Gln
                30                  35                  40

gcc att acc cat gag act act gct ggc tcg ctg ttg cct gtg gtc atc       316
Ala Ile Thr His Glu Thr Thr Ala Gly Ser Leu Leu Pro Val Val Ile
            45                  50                  55

att gca gtg ggt gcc ttc ctc ttc ctg gtg gcc ttt gtg ggc tgc tgt       364
Ile Ala Val Gly Ala Phe Leu Phe Leu Val Ala Phe Val Gly Cys Cys
        60                  65                  70

ggg gcc tgc aag gag aac tac tgt ctc atg att aca ttt gcc atc ttc       412
Gly Ala Cys Lys Glu Asn Tyr Cys Leu Met Ile Thr Phe Ala Ile Phe
    75                  80                  85

ctg tct ctt atc atg ctt gtg gag gtg gct gtg gcc att gct ggc tat       460
Leu Ser Leu Ile Met Leu Val Glu Val Ala Val Ala Ile Ala Gly Tyr
90                  95                  100                 105

gtg ttt aga gac cag gtg aag tca gag ttt aat aaa agc ttc cag cag       508
Val Phe Arg Asp Gln Val Lys Ser Glu Phe Asn Lys Ser Phe Gln Gln
                110                 115                 120

cag atg cag aat tac ctt aaa gac aac aaa aca gcc act att ttg gac       556
Gln Met Gln Asn Tyr Leu Lys Asp Asn Lys Thr Ala Thr Ile Leu Asp
            125                 130                 135

aaa ttg cag aaa gaa aat aac tgc tgt gga gct tct aac tac aca gac       604
Lys Leu Gln Lys Glu Asn Asn Cys Cys Gly Ala Ser Asn Tyr Thr Asp
```

```
        140                 145                 150

tgg gaa aac atc ccc ggc atg gcc aag gac aga gtc ccc gat tct tgc      652
Trp Glu Asn Ile Pro Gly Met Ala Lys Asp Arg Val Pro Asp Ser Cys
    155                 160                 165

tgc atc aac ata act gtg ggc tgt ggg aat gat ttc aag gaa tcc act      700
Cys Ile Asn Ile Thr Val Gly Cys Gly Asn Asp Phe Lys Glu Ser Thr
170                 175                 180                 185

atc cat acc cag ggc tgc gtg gag act ata gca ata tgg cta agg aag      748
Ile His Thr Gln Gly Cys Val Glu Thr Ile Ala Ile Trp Leu Arg Lys
                190                 195                 200

aac ata ctg ctg gtg gct gca gcg gcc ctg ggc att gct ttt gtg gag      796
Asn Ile Leu Leu Val Ala Ala Ala Ala Leu Gly Ile Ala Phe Val Glu
            205                 210                 215

gtc ttg gga att atc ttc tcc tgc tgt ctg gtg aag agt att cga agt      844
Val Leu Gly Ile Ile Phe Ser Cys Cys Leu Val Lys Ser Ile Arg Ser
        220                 225                 230

ggc tat gaa gta atg tag gggtgggggg cgtttggtct tttcatggag             892
Gly Tyr Glu Val Met
    235

tggattctcc aggtttttca attaaacgga ttattttttc agacctaaaa aaaaaaaaaa    952

aaaaaaa                                                              959


<210> SEQ ID NO 4
<211> LENGTH: 238
<212> TYPE: PRT
<213> ORGANISM: Mus musculus

<400> SEQUENCE: 4

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Ile Gly
            20                  25                  30

Val Ala Val Gln Val Val Leu Lys Gln Ala Ile Thr His Glu Thr Thr
        35                  40                  45

Ala Gly Ser Leu Leu Pro Val Val Ile Ile Ala Val Gly Ala Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Val Ala Ile Ala Gly Tyr Val Phe Arg Asp Gln Val Lys
            100                 105                 110

Ser Glu Phe Asn Lys Ser Phe Gln Gln Gln Met Gln Asn Tyr Leu Lys
        115                 120                 125

Asp Asn Lys Thr Ala Thr Ile Leu Asp Lys Leu Gln Lys Glu Asn Asn
    130                 135                 140

Cys Cys Gly Ala Ser Asn Tyr Thr Asp Trp Glu Asn Ile Pro Gly Met
145                 150                 155                 160

Ala Lys Asp Arg Val Pro Asp Ser Cys Cys Ile Asn Ile Thr Val Gly
                165                 170                 175

Cys Gly Asn Asp Phe Lys Glu Ser Thr Ile His Thr Gln Gly Cys Val
            180                 185                 190

Glu Thr Ile Ala Ile Trp Leu Arg Lys Asn Ile Leu Leu Val Ala Ala
        195                 200                 205

Ala Ala Leu Gly Ile Ala Phe Val Glu Val Leu Gly Ile Ile Phe Ser
    210                 215                 220
```

```
Cys Cys Leu Val Lys Ser Ile Arg Ser Gly Tyr Glu Val Met
225                 230                 235


<210> SEQ ID NO 5
<211> LENGTH: 1321
<212> TYPE: DNA
<213> ORGANISM: Homo sapiens
<220> FEATURE:
<221> NAME/KEY: CDS
<222> LOCATION: (185)..(871)

<400> SEQUENCE: 5

cttttcccgg cacatgcgca ccgcagcggg tcgcgcgccc taaggagtgg cactttttaa      60

aagtgcagcc ggagaccagc ctacagccgc ctgcatctgt atccagcgcc aggtcccgcc     120

agtcccagct gcgcgcgccc cccagtcccg cacccgttcg gcccaggcta agttagccct     180

cacc atg ccg gtc aaa gga ggc acc aag tgc atc aaa tac ctg ctg ttc      229
     Met Pro Val Lys Gly Gly Thr Lys Cys Ile Lys Tyr Leu Leu Phe
     1               5                   10                  15

gga ttt aac ttc atc ttc tgg ctt gcc ggg att gct gtc ctt gcc att      277
Gly Phe Asn Phe Ile Phe Trp Leu Ala Gly Ile Ala Val Leu Ala Ile
                20                  25                  30

gga cta tgg ctc cga ttc gac tct cag acc aag agc atc ttc gag caa      325
Gly Leu Trp Leu Arg Phe Asp Ser Gln Thr Lys Ser Ile Phe Glu Gln
            35                  40                  45

gaa act aat aat aat aat tcc agc ttc tac aca gga gtc tat att ctg      373
Glu Thr Asn Asn Asn Asn Ser Ser Phe Tyr Thr Gly Val Tyr Ile Leu
        50                  55                  60

atc gga gcc ggc gcc ctc atg atg ctg gtg ggc ttc ctg ggc tgc tgc      421
Ile Gly Ala Gly Ala Leu Met Met Leu Val Gly Phe Leu Gly Cys Cys
    65                  70                  75

ggg gct gtg cag gag tcc cag tgc atg ctg gga ctg ttc ttc ggc ttc      469
Gly Ala Val Gln Glu Ser Gln Cys Met Leu Gly Leu Phe Phe Gly Phe
80                  85                  90                  95

ctc ttg gtg ata ttc gcc att gaa ata gct gcg gcc atc tgg gga tat      517
Leu Leu Val Ile Phe Ala Ile Glu Ile Ala Ala Ala Ile Trp Gly Tyr
                100                 105                 110

tcc cac aag gat gag gtg att aag gaa gtc cag gag ttt tac aag gac      565
Ser His Lys Asp Glu Val Ile Lys Glu Val Gln Glu Phe Tyr Lys Asp
            115                 120                 125

acc tac aac aag ctg aaa acc aag gat gag ccc cag cgg gaa acg ctg      613
Thr Tyr Asn Lys Leu Lys Thr Lys Asp Glu Pro Gln Arg Glu Thr Leu
        130                 135                 140

aaa gcc atc cac tat gcg ttg aac tgc tgt ggt ttg gct ggg ggc gtg      661
Lys Ala Ile His Tyr Ala Leu Asn Cys Cys Gly Leu Ala Gly Gly Val
    145                 150                 155

gaa cag ttt atc tca gac atc tgc ccc aag aag gac gta ctc gaa acc      709
Glu Gln Phe Ile Ser Asp Ile Cys Pro Lys Lys Asp Val Leu Glu Thr
160                 165                 170                 175

ttc acc gtg aag tcc tgt cct gat gcc atc aaa gag gtc ttc gac aat      757
Phe Thr Val Lys Ser Cys Pro Asp Ala Ile Lys Glu Val Phe Asp Asn
                180                 185                 190

aaa ttc cac atc atc ggc gca gtg ggc atc ggc att gcc gtg gtc atg      805
Lys Phe His Ile Ile Gly Ala Val Gly Ile Gly Ile Ala Val Val Met
            195                 200                 205

ata ttt ggc atg atc ttc agt atg atc ttg tgc tgt gct atc cgc agg      853
Ile Phe Gly Met Ile Phe Ser Met Ile Leu Cys Cys Ala Ile Arg Arg
        210                 215                 220

aac cgc gag atg gtc tag agtcagctta catccctgag caggaaagtt             901
Asn Arg Glu Met Val
```

225 tacccatgaa gattggtggg attttttgtt tgtttgtttt gttttgtttg ttgtttgttg 961 tttgtttttt tgccactaat tttagtattc attctgcatt gctagataaa agctgaagtt 1021 actttatgtt tgtcttttaa tgcttcattc aatattgaca tttgtagttg agcgggggt 1081 ttggtttgct ttggtttata ttttttcagt tgtttgtttt tgcttgttat attaagcaga 1141 aatcctgcaa tgaaaggtac tatatttgct agactctaga caagatattg tacataaaag 1201 aattttttg tctttaaata gatacaaatg tctatcaact ttaatcaagt tgtaacttat 1261 attgaagaca atttgataca taataaaaaa ttatgacaat gtcctggact ggtaaaaaaa 1321

<210> SEQ ID NO 6
<211> LENGTH: 228
<212> TYPE: PRT
<213> ORGANISM: Homo sapiens

<400> SEQUENCE: 6

```
Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225
```

<210> SEQ ID NO 7
<211> LENGTH: 1306
<212> TYPE: DNA
<213> ORGANISM: Mus musculus
<220> FEATURE:
<221> NAME/KEY: CDS
<222> LOCATION: (117)..(797)

<400> SEQUENCE: 7

```
tttttaaaag tggagcctca ggccagcccc tagccgcagc gtgtctcagt cggttgtcga      60

gtcccttctg tcccagtcgt tcgtgcctct tgtcccacgc aactccagct tgtacc atg     119
                                                              Met
                                                              1

ccg gtc aaa gga ggt agc aag tgc atc aaa tac ctg ctc ttc gga ttt      167
Pro Val Lys Gly Gly Ser Lys Cys Ile Lys Tyr Leu Leu Phe Gly Phe
            5                   10                  15

aac ttc atc ttc tgg ctc gct ggc att gca gtg ctt gct att gga cta      215
Asn Phe Ile Phe Trp Leu Ala Gly Ile Ala Val Leu Ala Ile Gly Leu
        20                  25                  30

tgg ctc cga ttc gac tct cag acc aag agc atc ttc gag caa gag aat      263
Trp Leu Arg Phe Asp Ser Gln Thr Lys Ser Ile Phe Glu Gln Glu Asn
    35                  40                  45

aac cat tcc agt ttc tac aca gga gtg tac att ctg att gga gcc ggg      311
Asn His Ser Ser Phe Tyr Thr Gly Val Tyr Ile Leu Ile Gly Ala Gly
50                  55                  60                  65

gcc ctc atg atg ctg gtt ggt ttc ctg ggc tgc tgt gga gct gta caa      359
Ala Leu Met Met Leu Val Gly Phe Leu Gly Cys Cys Gly Ala Val Gln
                70                  75                  80

gag tcc cag tgc atg ctg gga ttg ttc ttc ggg ttc ctc ttg gtg ata      407
Glu Ser Gln Cys Met Leu Gly Leu Phe Phe Gly Phe Leu Leu Val Ile
            85                  90                  95

ttc gcc att gag ata gcc gcc gcc gtc tgg ggc tat acc cac aag gat      455
Phe Ala Ile Glu Ile Ala Ala Ala Val Trp Gly Tyr Thr His Lys Asp
        100                 105                 110

gag gtg att aaa gaa ctc cag gag ttt tac aag gac acc tac caa aag      503
Glu Val Ile Lys Glu Leu Gln Glu Phe Tyr Lys Asp Thr Tyr Gln Lys
    115                 120                 125

tta cgg agc aag gat gaa ccc cag cgg gaa aca ctc aaa gcc atc cat      551
Leu Arg Ser Lys Asp Glu Pro Gln Arg Glu Thr Leu Lys Ala Ile His
130                 135                 140                 145

atg gcg ttg gac tgc tgt ggc ata gct ggt cct ttg gag cag ttt atc      599
Met Ala Leu Asp Cys Cys Gly Ile Ala Gly Pro Leu Glu Gln Phe Ile
                150                 155                 160

tcg gac acc tgc ccc aag aaa cag ctt ttg gaa agt ttc cag gtt aag      647
Ser Asp Thr Cys Pro Lys Lys Gln Leu Leu Glu Ser Phe Gln Val Lys
            165                 170                 175

ccc tgc cct gaa gcc atc agt gag gtc ttc aac aac aag ttc cac atc      695
Pro Cys Pro Glu Ala Ile Ser Glu Val Phe Asn Asn Lys Phe His Ile
        180                 185                 190

att gga gca gtg ggt atc ggc atc gcc gtg gtg atg atc ttc ggc atg      743
Ile Gly Ala Val Gly Ile Gly Ile Ala Val Val Met Ile Phe Gly Met
    195                 200                 205

atc ttc agc atg atc ctg tgc tgc gcc atc cgc agg agc cga gaa atg      791
Ile Phe Ser Met Ile Leu Cys Cys Ala Ile Arg Arg Ser Arg Glu Met
210                 215                 220                 225

gtc tag agtctgccca accccgagca ggaacaacgg ccctgaagac tgtccgggcc       847
Val

atttgggttt tttttgccac taatattagt attcattatg catttctaaa taacagtcat    907

tctgtttgtc tttttaatgc tttattcatt attgacattt gtagttgagg gatccggggg    967

ttcaatttat tttgattttt ttttttggtt gtttattttt gcttgttatg ttaagcaaaa   1027

atcctgcaat gaaaggtact atatttgcca gactctagac ataagatatt gtacataaag   1087

agaatttttt ttgcctttaa atagataaaa gtatctatca gataaaaatc aggttgtaag   1147

ttatattgaa gacaatttga tacataataa aagattataa cagtgaaaaa aaaaaaaaaa   1207

aaaaaaaaaa aaaaaaaaaa aaaaaaaaaa aaaaaaaaaa aaaaaaaaaa aaaaaaaaaa   1267
```

```
aaaaaaaaaa aaaaaaaaaa aaaaaaaaaa aaaaaaaaa                          1306


<210> SEQ ID NO 8
<211> LENGTH: 226
<212> TYPE: PRT
<213> ORGANISM: Mus musculus

<400> SEQUENCE: 8

Met Pro Val Lys Gly Gly Ser Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Asn Asn His Ser Ser Phe Tyr Thr Gly Val Tyr Ile Leu Ile Gly Ala
    50                  55                  60

Gly Ala Leu Met Met Leu Val Gly Phe Leu Gly Cys Cys Gly Ala Val
65                  70                  75                  80

Gln Glu Ser Gln Cys Met Leu Gly Leu Phe Phe Gly Phe Leu Leu Val
                85                  90                  95

Ile Phe Ala Ile Glu Ile Ala Ala Ala Val Trp Gly Tyr Thr His Lys
            100                 105                 110

Asp Glu Val Ile Lys Glu Leu Gln Glu Phe Tyr Lys Asp Thr Tyr Gln
        115                 120                 125

Lys Leu Arg Ser Lys Asp Glu Pro Gln Arg Glu Thr Leu Lys Ala Ile
    130                 135                 140

His Met Ala Leu Asp Cys Cys Gly Ile Ala Gly Pro Leu Glu Gln Phe
145                 150                 155                 160

Ile Ser Asp Thr Cys Pro Lys Lys Gln Leu Leu Glu Ser Phe Gln Val
                165                 170                 175

Lys Pro Cys Pro Glu Ala Ile Ser Glu Val Phe Asn Asn Lys Phe His
            180                 185                 190

Ile Ile Gly Ala Val Gly Ile Gly Ile Ala Val Val Met Ile Phe Gly
        195                 200                 205

Met Ile Phe Ser Met Ile Leu Cys Cys Ala Ile Arg Arg Ser Arg Glu
    210                 215                 220

Met Val
225


<210> SEQ ID NO 9
<211> LENGTH: 1379
<212> TYPE: DNA
<213> ORGANISM: Homo sapiens
<220> FEATURE:
<221> NAME/KEY: CDS
<222> LOCATION: (329)..(826)

<400> SEQUENCE: 9

tttggttcct tgtggccaca tttccagtac ccagtagtca tctgtgccag gggttatcc      60

aggtacagaa cattcccatc gttgcagaag gttctatcag ctagcactgg gttggacgac    120

acttgccaag acgagctggc tagaggatgg ttctccggac ctggtcccac gtggttccca    180

gctggctgga ggcgtgatcc tgggtgtggc cctgtggctc cgccatgacc cgcagaccac    240

caacctcctg tatctggagc tgggagacaa gcccgcgccc aacaccttct atgtaggcat    300

ctacatcctc atcgctgtgg gcgctgtc atg atg ttc gtt ggc ttc ctg ggc       352
                               Met Met Phe Val Gly Phe Leu Gly
```

-continued

```
                             1              5

tgc tac ggg gcc atc cag gaa tcc cag tgc ctg ctg ggg acg ttc ttc      400
Cys Tyr Gly Ala Ile Gln Glu Ser Gln Cys Leu Leu Gly Thr Phe Phe
    10                  15                  20

acc tgc ctg gtc atc ctg ttt gcc tgt gag gtg gcc gcc ggc atc tgg      448
Thr Cys Leu Val Ile Leu Phe Ala Cys Glu Val Ala Ala Gly Ile Trp
25                  30                  35                  40

ggc ttt gtc aac aag gac cag atc gcc aag gat gtg aag cag ttc tat      496
Gly Phe Val Asn Lys Asp Gln Ile Ala Lys Asp Val Lys Gln Phe Tyr
                45                  50                  55

gac cag gcc cta cag cag gcc gtg gtg gat gat gac gcc aac aac gcc      544
Asp Gln Ala Leu Gln Gln Ala Val Val Asp Asp Asp Ala Asn Asn Ala
            60                  65                  70

aag gct gtg gtg aag acc ttc cac gag acg ctt gac tgc tgt ggc tcc      592
Lys Ala Val Val Lys Thr Phe His Glu Thr Leu Asp Cys Cys Gly Ser
        75                  80                  85

agc aca ctg act gct ttg acc acc tca gtg ctc aag aac aat ttg tgt      640
Ser Thr Leu Thr Ala Leu Thr Thr Ser Val Leu Lys Asn Asn Leu Cys
    90                  95                  100

ccc tcg ggc agc aac atc atc agc aac ctc ttc aag gag gac tgc cac      688
Pro Ser Gly Ser Asn Ile Ile Ser Asn Leu Phe Lys Glu Asp Cys His
105                 110                 115                 120

cag aag atc gat gac ctc ttc tcc ggg aag ctg tac ctc atc ggc att      736
Gln Lys Ile Asp Asp Leu Phe Ser Gly Lys Leu Tyr Leu Ile Gly Ile
                125                 130                 135

gct gcc atc gtg gtc gct gtg atc atg atc ttc gag atg atc ctg agc      784
Ala Ala Ile Val Val Ala Val Ile Met Ile Phe Glu Met Ile Leu Ser
            140                 145                 150

atg gtg ctg tgc tgt ggc atc cgg aac agc tcc gtg tac tga              826
Met Val Leu Cys Cys Gly Ile Arg Asn Ser Ser Val Tyr
        155                 160                 165

ggccccgcag ctctggccac agggacctct gcagtgcccc ctaagtgacc cggacacttc    886

cgagggggcc atcaccgcct gtgtatataa cgtttccggt attactctgc tacacgtagc    946

ctttttactt ttggggtttt gtttttgttc tgaactttcc tgttaccttt tcagggctga   1006

cgtcacatgt aggtggcgtg tatgagtgga gacgggcctg ggtcttgggg actggagggc   1066

aggggtcctt ctgccctggg gtcccagggt gctctgcctg ctcagccagg cctctcctgg   1126

gagccactcg cccagagact cagcttggcc aacttggggg gctgtgtcca cccagcccgc   1186

ccgtcctgtg ggctgcacag ctcaccttgt tccctcctgc cccggttcga gagccgagtc   1246

tgtgggcact ctctgccttc atgcacctgt cctttctaac acgtcgcctt caactgtaat   1306

cacaacatcc tgactccgtc atttaataaa gaaggaacat caggcatgct accaggcctg   1366

tgcagtccct cag                                                      1379


<210> SEQ ID NO 10
<211> LENGTH: 165
<212> TYPE: PRT
<213> ORGANISM: Homo sapiens

<400> SEQUENCE: 10

Met Met Phe Val Gly Phe Leu Gly Cys Tyr Gly Ala Ile Gln Glu Ser
1               5                   10                  15

Gln Cys Leu Leu Gly Thr Phe Phe Thr Cys Leu Val Ile Leu Phe Ala
            20                  25                  30

Cys Glu Val Ala Ala Gly Ile Trp Gly Phe Val Asn Lys Asp Gln Ile
        35                  40                  45
```

```
Ala Lys Asp Val Lys Gln Phe Tyr Asp Gln Ala Leu Gln Gln Ala Val
    50                  55                  60

Val Asp Asp Asp Ala Asn Asn Ala Lys Ala Val Val Lys Thr Phe His
65                  70                  75                  80

Glu Thr Leu Asp Cys Cys Gly Ser Ser Thr Leu Thr Ala Leu Thr Thr
                85                  90                  95

Ser Val Leu Lys Asn Asn Leu Cys Pro Ser Gly Ser Asn Ile Ile Ser
            100                 105                 110

Asn Leu Phe Lys Glu Asp Cys His Gln Lys Ile Asp Asp Leu Phe Ser
        115                 120                 125

Gly Lys Leu Tyr Leu Ile Gly Ile Ala Ala Ile Val Val Ala Val Ile
    130                 135                 140

Met Ile Phe Glu Met Ile Leu Ser Met Val Leu Cys Cys Gly Ile Arg
145                 150                 155                 160

Asn Ser Ser Val Tyr
                165


<210> SEQ ID NO 11
<211> LENGTH: 1534
<212> TYPE: DNA
<213> ORGANISM: Mus musculus
<220> FEATURE:
<221> NAME/KEY: CDS
<222> LOCATION: (252)..(962)

<400> SEQUENCE: 11

gaggtctata aagagtgagg agctaggcgc gcgcgcccgg tccgagcgag cgcgtccttg      60

cttcaaagag atagtgactc tcgcgcctcc ggctaggcct ccagcccttc tctaccctac     120

gtctcattct ccgcaacgca gttctccggc ccgcaagcgc tccaggctat ctgccagtcc     180

cggaccccgg tactgcgtcc ccataccgcc cgctccagga ccaatccaag ctccgcaggc     240

cgcgcaccgc c atg ggg gtg gag ggc tgc acc aaa tgc atc aaa tac ctg      290
             Met Gly Val Glu Gly Cys Thr Lys Cys Ile Lys Tyr Leu
             1               5                   10

ctc ttc gtc ttc aat ttc gtc ttc tgg ctg gct gga ggc gtg atc cta      338
Leu Phe Val Phe Asn Phe Val Phe Trp Leu Ala Gly Gly Val Ile Leu
    15                  20                  25

ggt gta gct ctg tgg ttg cgt cat gat cca cag acc acc agc ctg ctg      386
Gly Val Ala Leu Trp Leu Arg His Asp Pro Gln Thr Thr Ser Leu Leu
30                  35                  40                  45

tac ctg gaa ctg gga aac aaa ccg gca ccc aac acc ttc tac gtg ggc      434
Tyr Leu Glu Leu Gly Asn Lys Pro Ala Pro Asn Thr Phe Tyr Val Gly
                50                  55                  60

atc tac att ctc att gct gtg gga gct gtg atg atg ttt gta ggc ttc      482
Ile Tyr Ile Leu Ile Ala Val Gly Ala Val Met Met Phe Val Gly Phe
            65                  70                  75

ctg ggg tgc tat ggg gcc atc cag gag tcc cag tgt ctg ctg ggg acg      530
Leu Gly Cys Tyr Gly Ala Ile Gln Glu Ser Gln Cys Leu Leu Gly Thr
        80                  85                  90

ttc ttc acc tgc ctt gtg atc ctg ttt gcc tgt gag gtg gct gca ggc      578
Phe Phe Thr Cys Leu Val Ile Leu Phe Ala Cys Glu Val Ala Ala Gly
    95                  100                 105

atc tgg ggc ttc gta aac aaa gac cag atc gcc aag gat gtg aag cag      626
Ile Trp Gly Phe Val Asn Lys Asp Gln Ile Ala Lys Asp Val Lys Gln
110                 115                 120                 125

ttc tat gac cag gcc ctt cag caa gct gtg atg gat gat gat gcc aac      674
Phe Tyr Asp Gln Ala Leu Gln Gln Ala Val Met Asp Asp Asp Ala Asn
                130                 135                 140
```

```
aat gcc aag gct gtg gtg aag act ttc cat gag acg ctc aac tgt tgt      722
Asn Ala Lys Ala Val Val Lys Thr Phe His Glu Thr Leu Asn Cys Cys
            145                 150                 155

ggc tcc aac gca ctg acc aca ctg act acc acc ata ctg agg aac agc      770
Gly Ser Asn Ala Leu Thr Thr Leu Thr Thr Thr Ile Leu Arg Asn Ser
        160                 165                 170

ctg tgt ccc tca ggc ggc aac ata ctc acc ccc tta ctg cag caa gat      818
Leu Cys Pro Ser Gly Gly Asn Ile Leu Thr Pro Leu Leu Gln Gln Asp
    175                 180                 185

tgt cat cag aaa atc gat gag ctc ttc tct ggg aag ctg tac ctc att      866
Cys His Gln Lys Ile Asp Glu Leu Phe Ser Gly Lys Leu Tyr Leu Ile
190                 195                 200                 205

gga att gca gcc att gtg gta gct gtc att atg atc ttt gag atg att      914
Gly Ile Ala Ala Ile Val Val Ala Val Ile Met Ile Phe Glu Met Ile
                210                 215                 220

ctg agc atg gtg ctg tgc tgt ggc atc cgg aac agc tcc gtg tac tga      962
Leu Ser Met Val Leu Cys Cys Gly Ile Arg Asn Ser Ser Val Tyr
            225                 230                 235

ggccctttgc attgcaccag aggatccctg gagtgaccag aggccacctt gggggacatg   1022

gcctgtgtat ataatatttc tgtatcactc tgctacactt agtcttttta cttttgagtt   1082

ttttgttttg ttttgttttg tttttgtttt agttttttt tttgtcctga acttttcctg   1142

ttacctttg ggagctgaca tcacacatgg gtggcatatg tgggatgtag ggtggagct     1202

ggccctggct tgcagggccc tgtacgtctg ggacccctgg agagttctgc ctgctgagcc   1262

aaacctcctc tacagctact tgcccagagg ctttgtagcc tagctagagg gccatgccca   1322

cccactcaac ccactgtggg tcacattgct cacatctttt taatctttgt tcctttcctg   1382

cctccatttc aagagctggg tttgtaagcc ctcttatgcc ttcaatgcac ttattctttc   1442

taacgtgtca ccttcaactg taattaaatc ttgaaacagt catttaataa aggaggaaaa   1502

aaatcaggca tgctaaaaaa aaaaaaaaaa aa                                  1534


<210> SEQ ID NO 12
<211> LENGTH: 236
<212> TYPE: PRT
<213> ORGANISM: Mus musculus

<400> SEQUENCE: 12

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Ser Leu Leu Tyr Leu Glu
        35                  40                  45

Leu Gly Asn Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Met Asp Asp Asp Ala Asn Asn Ala Lys
    130                 135                 140
```

```
Ala Val Val Lys Thr Phe His Glu Thr Leu Asn Cys Cys Gly Ser Asn
145                 150                 155                 160

Ala Leu Thr Thr Leu Thr Thr Thr Ile Leu Arg Asn Ser Leu Cys Pro
                165                 170                 175

Ser Gly Gly Asn Ile Leu Thr Pro Leu Leu Gln Gln Asp Cys His Gln
            180                 185                 190

Lys Ile Asp Glu Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235


<210> SEQ ID NO 13
<211> LENGTH: 4288
<212> TYPE: DNA
<213> ORGANISM: Mus musculus
<220> FEATURE:
<221> NAME/KEY: CDS
<222> LOCATION: (185)..(1960)

<400> SEQUENCE: 13

ggacgcgggg ttgggcttcg tgcggtgggg ctcgctcgcg cggcggccgt agccgaggcc      60

tcttagttct gcggcacgtg acggtcgggc cgcctctgcc gctgtctcca ctgcagcacg     120

gggccgggtg tgcgggtggg agaaggtgag ggagccgcca gtggtccccg ggaggctcga     180

gatc atg gaa ggg aag tgg tta ctg tgt ttg ctg ctg gtc ctt gga act      229
     Met Glu Gly Lys Trp Leu Leu Cys Leu Leu Leu Val Leu Gly Thr
     1               5                   10                  15

gca gct gtt gag gct cat gat gga cat gat gat gac gcg att gat att      277
Ala Ala Val Glu Ala His Asp Gly His Asp Asp Asp Ala Ile Asp Ile
                20                  25                  30

gaa gat gat ctt gat gat gtt att gaa gag gta gaa gat tca aaa tct      325
Glu Asp Asp Leu Asp Asp Val Ile Glu Glu Val Glu Asp Ser Lys Ser
            35                  40                  45

aaa tca gat gcc agc act cct cca tct cca aag gtc acc tac aaa gct      373
Lys Ser Asp Ala Ser Thr Pro Pro Ser Pro Lys Val Thr Tyr Lys Ala
        50                  55                  60

cca gtt cca aca ggg gag gtt tat ttt gct gac tcc ttt gac aga ggg      421
Pro Val Pro Thr Gly Glu Val Tyr Phe Ala Asp Ser Phe Asp Arg Gly
    65                  70                  75

tct ctg tca ggg tgg att tta tct aaa gcc aaa aaa gat gac act gat      469
Ser Leu Ser Gly Trp Ile Leu Ser Lys Ala Lys Lys Asp Asp Thr Asp
80                  85                  90                  95

gat gaa att gcc aaa tat gat gga aag tgg gaa gta gat gag atg aag      517
Asp Glu Ile Ala Lys Tyr Asp Gly Lys Trp Glu Val Asp Glu Met Lys
                100                 105                 110

gaa aca aag ctt cca ggg gat aaa gga ctt gta ctg atg tct cgg gcc      565
Glu Thr Lys Leu Pro Gly Asp Lys Gly Leu Val Leu Met Ser Arg Ala
            115                 120                 125

aag cat cat gcc atc tct gct aaa ctg aat aag ccc ttc ctg ttt gat      613
Lys His His Ala Ile Ser Ala Lys Leu Asn Lys Pro Phe Leu Phe Asp
        130                 135                 140

acc aag cct ctc att gtt cag tat gag gtt aat ttt cag aat gga ata      661
Thr Lys Pro Leu Ile Val Gln Tyr Glu Val Asn Phe Gln Asn Gly Ile
    145                 150                 155

gaa tgt ggt ggt gcc tat gtg aag ctg ctt tcc aag acg gca gag ctc      709
Glu Cys Gly Gly Ala Tyr Val Lys Leu Leu Ser Lys Thr Ala Glu Leu
160                 165                 170                 175
```

```
agc ctg gat caa ttc cac gac aag act ccc tat act att atg ttt ggt      757
Ser Leu Asp Gln Phe His Asp Lys Thr Pro Tyr Thr Ile Met Phe Gly
                180                 185                 190

cca gat aag tgt gga gag gac tac aaa ctg cat ttc atc ttt cga cac      805
Pro Asp Lys Cys Gly Glu Asp Tyr Lys Leu His Phe Ile Phe Arg His
            195                 200                 205

aaa aat ccc aag aca ggt gta tat gaa gaa aaa cat gct aag agg cca      853
Lys Asn Pro Lys Thr Gly Val Tyr Glu Glu Lys His Ala Lys Arg Pro
        210                 215                 220

gat gca gat ctg aag acc tat ttc act gac aag aaa acg cat ctt tat      901
Asp Ala Asp Leu Lys Thr Tyr Phe Thr Asp Lys Lys Thr His Leu Tyr
    225                 230                 235

aca tta atc ttg aat cca gac aat agt ttt gaa ata tta gtt gac cag      949
Thr Leu Ile Leu Asn Pro Asp Asn Ser Phe Glu Ile Leu Val Asp Gln
240                 245                 250                 255

tct gtt gtg aac agt gga aat ctg cta aat gac atg act cct cct gta      997
Ser Val Val Asn Ser Gly Asn Leu Leu Asn Asp Met Thr Pro Pro Val
                260                 265                 270

aac cct tca cgt gaa att gaa gac cca gaa gac cgg aag cct gaa gat     1045
Asn Pro Ser Arg Glu Ile Glu Asp Pro Glu Asp Arg Lys Pro Glu Asp
            275                 280                 285

tgg gat gaa agg ccc aaa ata gca gat cca gat gct gtc aag cca gat     1093
Trp Asp Glu Arg Pro Lys Ile Ala Asp Pro Asp Ala Val Lys Pro Asp
        290                 295                 300

gac tgg gat gaa gac gcc cct tct aag atc cca gat gaa gag gcc acc     1141
Asp Trp Asp Glu Asp Ala Pro Ser Lys Ile Pro Asp Glu Glu Ala Thr
    305                 310                 315

aag cct gaa ggc tgg cta gac gac gaa cct gag tat att cca gac cct     1189
Lys Pro Glu Gly Trp Leu Asp Asp Glu Pro Glu Tyr Ile Pro Asp Pro
320                 325                 330                 335

gat gca gag aag cca gag gat tgg gat gag gat atg gac gga gaa tgg     1237
Asp Ala Glu Lys Pro Glu Asp Trp Asp Glu Asp Met Asp Gly Glu Trp
                340                 345                 350

gag gct cct cag att gcc aac ccc aag tgt gag tca gcc cct ggg tgt     1285
Glu Ala Pro Gln Ile Ala Asn Pro Lys Cys Glu Ser Ala Pro Gly Cys
            355                 360                 365

ggt gtc tgg cag cga cct atg att gac aac ccc aat tat aag ggc aaa     1333
Gly Val Trp Gln Arg Pro Met Ile Asp Asn Pro Asn Tyr Lys Gly Lys
        370                 375                 380

tgg aag cct cca atg att gac aac cct aac tac cag gga atc tgg aaa     1381
Trp Lys Pro Pro Met Ile Asp Asn Pro Asn Tyr Gln Gly Ile Trp Lys
    385                 390                 395

cca agg aaa ata cca aat cca gat ttc ttt gaa gac cta gaa cct ttt     1429
Pro Arg Lys Ile Pro Asn Pro Asp Phe Phe Glu Asp Leu Glu Pro Phe
400                 405                 410                 415

aag atg act cct ttc agt gct att ggt ttg gag ctc tgg tcc atg aca     1477
Lys Met Thr Pro Phe Ser Ala Ile Gly Leu Glu Leu Trp Ser Met Thr
                420                 425                 430

tcc gac atc ttt ttt gac aac ttt atc att agt ggt gac cga aga gta     1525
Ser Asp Ile Phe Phe Asp Asn Phe Ile Ile Ser Gly Asp Arg Arg Val
            435                 440                 445

gtt gat gat tgg gcc aat gat ggg tgg ggc ctg aag aaa gct gct gat     1573
Val Asp Asp Trp Ala Asn Asp Gly Trp Gly Leu Lys Lys Ala Ala Asp
        450                 455                 460

ggg gct gct gag cca ggt gta gtg ctg cag atg ctg gag gca gct gaa     1621
Gly Ala Ala Glu Pro Gly Val Val Leu Gln Met Leu Glu Ala Ala Glu
    465                 470                 475

gag cgt cca tgg ctt tgg gtg gtc tac att ttg act gta gct ttg cca     1669
Glu Arg Pro Trp Leu Trp Val Val Tyr Ile Leu Thr Val Ala Leu Pro
480                 485                 490                 495
```

```
gtg ttc ctt gtg atc ctc ttc tgc tgt tct gga aag aaa cag tcc aat     1717
Val Phe Leu Val Ile Leu Phe Cys Cys Ser Gly Lys Lys Gln Ser Asn
                500                 505                 510

gct atg gag tac aag aag acg gat gct ccc cag cca gat gtg aag gat     1765
Ala Met Glu Tyr Lys Lys Thr Asp Ala Pro Gln Pro Asp Val Lys Asp
            515                 520                 525

gaa gaa ggg aag gaa gaa gag aag aac aag agg gat gaa gag gaa gaa     1813
Glu Glu Gly Lys Glu Glu Glu Lys Asn Lys Arg Asp Glu Glu Glu Glu
        530                 535                 540

gag gag aag ctt gaa gag aaa cag aag agt gat gct gaa gaa gat ggt     1861
Glu Glu Lys Leu Glu Glu Lys Gln Lys Ser Asp Ala Glu Glu Asp Gly
    545                 550                 555

gtt act ggc agt caa gat gag gaa gat agc aag cct aaa gca gag gag     1909
Val Thr Gly Ser Gln Asp Glu Glu Asp Ser Lys Pro Lys Ala Glu Glu
560                 565                 570                 575

gat gaa att ttg aac aga tcg cca aga aac aga aag cca cga aga gag     1957
Asp Glu Ile Leu Asn Arg Ser Pro Arg Asn Arg Lys Pro Arg Arg Glu
                580                 585                 590

tga aacaatcttt aagaacttga tctgtgattt cctctccctc cccttcccct          2010

gcaaatgtgg tcctaggaga gggcctggtg taccttaggt gggagctcaa aacctcaaga   2070

tgtcaccatc aacaggttcc agtgaatact agcctgtaat tttaaacatc tagcagtaaa   2130

taattgcagt tgtaatgtaa aggaccctgt ttctgtagaa aggaaaacat ttaacataat   2190

ggttgtgaaa tgtaacatga agcaactaac tagtgttttg ttgtttttaa aattttccag   2250

gtttgtcttt ttttttttcc ttttcctttt tttttttttt ttagatacaa tgatagaatt   2310

tttgccagtt taaaatcttg gcttaattta atatattcat ttgttcatgc agaaataaca   2370

ccaacattag gaatgctagg gagaatgaat tgccgttttt ataataactt ttttaagttt   2430

ggtattaaag cattcatgtg tctgtcctaa aattgtaatc acgttcaagt gcagttattt   2490

gtggttataa atcttgtttt gtgtgcttcc attagttaat tcctcttaaa gacacaagag   2550

cgattggatg gaagcccaaa tttatatcaa agttcccttt acattgtatt gaatagaccc   2610

aaaaagaact aaaaggagac tttgacttgg tcatttcaca tcagatcata aagtgcagtg   2670

ttctgttgcc ctagagactg ctccattcac aagcaccttt gaagagggaa ggagctggct   2730

tcatgtagca gttcatactg tacttcccac ataggaggtc tgacagctcg ggtcctctgg   2790

agcacaaggc tttttaagga atgctggtgg tgcctgggta gataattaca tcacttgttc   2850

cactgtgttg acactgtttt cctcatggat ctcctccatt cctagctttc tctgctatgc   2910

attttcttca cagcgcagct tgcggtccgt tgctgaaaat tataagctct gcatagtgtt   2970

ggctttactg tgatgacatg tttcttcttt tttagctggc ccacaccttt ctagggtcca   3030

actacaggat agattacaga ctttccatta gtgtctattt cttttactct gtgtagactt   3090

tagaaagtct aatcaatcca gagatgggcc aattcagaat tgactataat tgaacacctg   3150

ctaaaagtat ttatgggagg attgacacac agcatgagtt atttgacttt tgtaggatat   3210

ttaaaatctt catttgcagt tcatgtaaca gttgtgtctt aaaattcaca taataaagca   3270

gtcctgttca aaaaaaaaat tttttttttg tggcttgtag aattttttaa aagtgtattt   3330

agggcttttt gtttttttgtt tgttttttttg ttttgttttt catgtggaat gcagatgggt   3390

gctagaggag cctctcccac atcactatag tgtaatatta ttacaccaca ctgaaatgta   3450

ttcagaaaca gatgtttcaa tttcattctt tctccagagg tggtccagtt gtaccaatga   3510

tactattcct tgcactgaat atatataaac actcttcagt gtttatattg ggaaatact    3570
```

```
gggaaagaaa tatatttgtt aaggatgaag gctgtatctg ttgtctttat aaacactggt   3630

tcatttcttt tgagggtgga atgcattttt cttcctgttc agtgctttat caccatctgt   3690

tgtttgtggt cacagtgacc atagctatgt agcggacgtt tccaaatgta tagagtgaaa   3750

taaacagtta ctagcaagaa atgaatacat gtctgcaggt ttctccttga agcaaacatg   3810

gggatgattg cttttctaga aatcggttta tctgtttcat cattctacat tgacattgtt   3870

ttgtgcctac tttatattca cccaggctgt acaatgacag gtttatttat gtcactggtg   3930

gtggtcattg ccttttttggg tccctcttcc tccctcaagg ttccattgaa gctccagcct   3990

ccttaaatac ctgactcgtt agtaaatgat cagcagtctt cagctcttaa aaaaagcgta   4050

gagggcaggt attgtagctg agtaggtaga actgctaagc gtgtgcaagg ttccgtgggt   4110

ctgattcctg gcactgaatt aagatagata aaggccctta tattctgatt ttctatgctg   4170

gactccttgt tgtaaaatgt ccatgccagt agtactcttc tattgtccac ttttcagatt   4230

gtcacactgc taaatgacat tatattaaag cccgtgttaa atatctgtat cataaaaa     4288
```

<210> SEQ ID NO 14
<211> LENGTH: 591
<212> TYPE: PRT
<213> ORGANISM: Mus musculus

<400> SEQUENCE: 14

```
Met Glu Gly Lys Trp Leu Leu Cys Leu Leu Leu Val Leu Gly Thr Ala
1               5                   10                  15

Ala Val Glu Ala His Asp Gly His Asp Asp Asp Ala Ile Asp Ile Glu
            20                  25                  30

Asp Asp Leu Asp Asp Val Ile Glu Glu Val Glu Asp Ser Lys Ser Lys
        35                  40                  45

Ser Asp Ala Ser Thr Pro Pro Ser Pro Lys Val Thr Tyr Lys Ala Pro
    50                  55                  60

Val Pro Thr Gly Glu Val Tyr Phe Ala Asp Ser Phe Asp Arg Gly Ser
65                  70                  75                  80

Leu Ser Gly Trp Ile Leu Ser Lys Ala Lys Lys Asp Asp Thr Asp Asp
                85                  90                  95

Glu Ile Ala Lys Tyr Asp Gly Lys Trp Glu Val Asp Glu Met Lys Glu
            100                 105                 110

Thr Lys Leu Pro Gly Asp Lys Gly Leu Val Leu Met Ser Arg Ala Lys
        115                 120                 125

His His Ala Ile Ser Ala Lys Leu Asn Lys Pro Phe Leu Phe Asp Thr
    130                 135                 140

Lys Pro Leu Ile Val Gln Tyr Glu Val Asn Phe Gln Asn Gly Ile Glu
145                 150                 155                 160

Cys Gly Gly Ala Tyr Val Lys Leu Leu Ser Lys Thr Ala Glu Leu Ser
                165                 170                 175

Leu Asp Gln Phe His Asp Lys Thr Pro Tyr Thr Ile Met Phe Gly Pro
            180                 185                 190

Asp Lys Cys Gly Glu Asp Tyr Lys Leu His Phe Ile Phe Arg His Lys
        195                 200                 205

Asn Pro Lys Thr Gly Val Tyr Glu Glu Lys His Ala Lys Arg Pro Asp
    210                 215                 220

Ala Asp Leu Lys Thr Tyr Phe Thr Asp Lys Lys Thr His Leu Tyr Thr
225                 230                 235                 240

Leu Ile Leu Asn Pro Asp Asn Ser Phe Glu Ile Leu Val Asp Gln Ser
                245                 250                 255
```

Val Val Asn Ser Gly Asn Leu Leu Asn Asp Met Thr Pro Pro Val Asn
260 265 270

Pro Ser Arg Glu Ile Glu Asp Pro Glu Asp Arg Lys Pro Glu Asp Trp
275 280 285

Asp Glu Arg Pro Lys Ile Ala Asp Pro Asp Ala Val Lys Pro Asp Asp
290 295 300

Trp Asp Glu Asp Ala Pro Ser Lys Ile Pro Asp Glu Glu Ala Thr Lys
305 310 315 320

Pro Glu Gly Trp Leu Asp Asp Glu Pro Glu Tyr Ile Pro Asp Pro Asp
325 330 335

Ala Glu Lys Pro Glu Asp Trp Asp Glu Asp Met Asp Gly Glu Trp Glu
340 345 350

Ala Pro Gln Ile Ala Asn Pro Lys Cys Glu Ser Ala Pro Gly Cys Gly
355 360 365

Val Trp Gln Arg Pro Met Ile Asp Asn Pro Asn Tyr Lys Gly Lys Trp
370 375 380

Lys Pro Pro Met Ile Asp Asn Pro Asn Tyr Gln Gly Ile Trp Lys Pro
385 390 395 400

Arg Lys Ile Pro Asn Pro Asp Phe Phe Glu Asp Leu Glu Pro Phe Lys
405 410 415

Met Thr Pro Phe Ser Ala Ile Gly Leu Glu Leu Trp Ser Met Thr Ser
420 425 430

Asp Ile Phe Phe Asp Asn Phe Ile Ile Ser Gly Asp Arg Arg Val Val
435 440 445

Asp Asp Trp Ala Asn Asp Gly Trp Gly Leu Lys Lys Ala Ala Asp Gly
450 455 460

Ala Ala Glu Pro Gly Val Val Leu Gln Met Leu Glu Ala Ala Glu Glu
465 470 475 480

Arg Pro Trp Leu Trp Val Val Tyr Ile Leu Thr Val Ala Leu Pro Val
485 490 495

Phe Leu Val Ile Leu Phe Cys Cys Ser Gly Lys Lys Gln Ser Asn Ala
500 505 510

Met Glu Tyr Lys Lys Thr Asp Ala Pro Gln Pro Asp Val Lys Asp Glu
515 520 525

Glu Gly Lys Glu Glu Glu Lys Asn Lys Arg Asp Glu Glu Glu Glu Glu
530 535 540

Glu Lys Leu Glu Glu Lys Gln Lys Ser Asp Ala Glu Glu Asp Gly Val
545 550 555 560

Thr Gly Ser Gln Asp Glu Glu Asp Ser Lys Pro Lys Ala Glu Glu Asp
565 570 575

Glu Ile Leu Asn Arg Ser Pro Arg Asn Arg Lys Pro Arg Arg Glu
580 585 590

<210> SEQ ID NO 15
<211> LENGTH: 1873
<212> TYPE: DNA
<213> ORGANISM: Gallus gallus
<220> FEATURE:
<221> NAME/KEY: CDS
<222> LOCATION: (66)..(1226)

<400> SEQUENCE: 15
gacatacagc tagaaagctg tattgccttt agcactcaag ctcaaaagac aactcagagt 60 tcacc atg ggc tcc atc ggc gca gca agc atg gaa ttt tgt ttt gat gta 110
Met Gly Ser Ile Gly Ala Ala Ser Met Glu Phe Cys Phe Asp Val -continued

```
  1               5                  10                 15

ttc aag gag ctc aaa gtc cac cat gcc aat gag aac atc ttc tac tgc      158
Phe Lys Glu Leu Lys Val His His Ala Asn Glu Asn Ile Phe Tyr Cys
                20                  25                  30

ccc att gcc atc atg tca gct cta gcc atg gta tac ctg ggt gca aaa      206
Pro Ile Ala Ile Met Ser Ala Leu Ala Met Val Tyr Leu Gly Ala Lys
            35                  40                  45

gac agc acc agg aca cag ata aat aag gtt gtt cgc ttt gat aaa ctt      254
Asp Ser Thr Arg Thr Gln Ile Asn Lys Val Val Arg Phe Asp Lys Leu
        50                  55                  60

cca gga ttc gga gac agt att gaa gct cag tgt ggc aca tct gta aac      302
Pro Gly Phe Gly Asp Ser Ile Glu Ala Gln Cys Gly Thr Ser Val Asn
    65                  70                  75

gtt cac tct tca ctt aga gac atc ctc aac caa atc acc aaa cca aat      350
Val His Ser Ser Leu Arg Asp Ile Leu Asn Gln Ile Thr Lys Pro Asn
80                  85                  90                  95

gat gtt tat tcg ttc agc ctt gcc agt aga ctt tat gct gaa gag aga      398
Asp Val Tyr Ser Phe Ser Leu Ala Ser Arg Leu Tyr Ala Glu Glu Arg
                100                 105                 110

tac cca atc ctg cca gaa tac ttg cag tgt gtg aag gaa ctg tat aga      446
Tyr Pro Ile Leu Pro Glu Tyr Leu Gln Cys Val Lys Glu Leu Tyr Arg
            115                 120                 125

gga ggc ttg gaa cct atc aac ttt caa aca gct gca gat caa gcc aga      494
Gly Gly Leu Glu Pro Ile Asn Phe Gln Thr Ala Ala Asp Gln Ala Arg
        130                 135                 140

gag ctc atc aat tcc tgg gta gaa agt cag aca aat gga att atc aga      542
Glu Leu Ile Asn Ser Trp Val Glu Ser Gln Thr Asn Gly Ile Ile Arg
    145                 150                 155

aat gtc ctt cag cca agc tcc gtg gat tct caa act gca atg gtt ctg      590
Asn Val Leu Gln Pro Ser Ser Val Asp Ser Gln Thr Ala Met Val Leu
160                 165                 170                 175

gtt aat gcc att gtc ttc aaa gga ctg tgg gag aaa aca ttt aag gat      638
Val Asn Ala Ile Val Phe Lys Gly Leu Trp Glu Lys Thr Phe Lys Asp
                180                 185                 190

gaa gac aca caa gca atg cct ttc aga gtg act gag caa gaa agc aaa      686
Glu Asp Thr Gln Ala Met Pro Phe Arg Val Thr Glu Gln Glu Ser Lys
            195                 200                 205

cct gtg cag atg atg tac cag att ggt tta ttt aga gtg gca tca atg      734
Pro Val Gln Met Met Tyr Gln Ile Gly Leu Phe Arg Val Ala Ser Met
        210                 215                 220

gct tct gag aaa atg aag atc ctg gag ctt cca ttt gcc agt ggg aca      782
Ala Ser Glu Lys Met Lys Ile Leu Glu Leu Pro Phe Ala Ser Gly Thr
    225                 230                 235

atg agc atg ttg gtg ctg ttg cct gat gaa gtc tca ggc ctt gag cag      830
Met Ser Met Leu Val Leu Leu Pro Asp Glu Val Ser Gly Leu Glu Gln
240                 245                 250                 255

ctt gag agt ata atc aac ttt gaa aaa ctg act gaa tgg acc agt tct      878
Leu Glu Ser Ile Ile Asn Phe Glu Lys Leu Thr Glu Trp Thr Ser Ser
                260                 265                 270

aat gtt atg gaa gag agg aag atc aaa gtg tac tta cct cgc atg aag      926
Asn Val Met Glu Glu Arg Lys Ile Lys Val Tyr Leu Pro Arg Met Lys
            275                 280                 285

atg gag gaa aaa tac aac ctc aca tct gtc tta atg gct atg ggc att      974
Met Glu Glu Lys Tyr Asn Leu Thr Ser Val Leu Met Ala Met Gly Ile
        290                 295                 300

act gac gtg ttt agc tct tca gcc aat ctg tct ggc atc tcc tca gca     1022
Thr Asp Val Phe Ser Ser Ser Ala Asn Leu Ser Gly Ile Ser Ser Ala
    305                 310                 315

gag agc ctg aag ata tct caa gct gtc cat gca gca cat gca gaa atc     1070
```

```
Glu Ser Leu Lys Ile Ser Gln Ala Val His Ala Ala His Ala Glu Ile
320                 325                 330                 335

aat gaa gca ggc aga gag gtg gta ggg tca gca gag gct gga gtg gat     1118
Asn Glu Ala Gly Arg Glu Val Val Gly Ser Ala Glu Ala Gly Val Asp
                340                 345                 350

gct gca agc gtc tct gaa gaa ttt agg gct gac cat cca ttc ctc ttc     1166
Ala Ala Ser Val Ser Glu Glu Phe Arg Ala Asp His Pro Phe Leu Phe
            355                 360                 365

tgt atc aag cac atc gca acc aac gcc gtt ctc ttc ttt ggc aga tgt     1214
Cys Ile Lys His Ile Ala Thr Asn Ala Val Leu Phe Phe Gly Arg Cys
        370                 375                 380

gtt tcc cct taa aaagaagaaa gctgaaaaac tctgtccctt ccaacaagac         1266
Val Ser Pro
    385

ccagagcact gtagtatcag gggtaaaatg aaaagtatgt tctctgctgc atccagactt   1326

cataaaagct ggagcttaat ctagaaaaaa aatcagaaag aaattacact gtgagaacag   1386

gtgcaattca cttttccttt acacagagta atactggtaa ctcatggatg aaggcttaag   1446

ggaatgaaat tggactcaca gtactgagtc atcacactga aaaatgcaac ctgatacatc   1506

agcagaaggt ttatggggga aaaatgcagc cttccaatta agccagatat ctgtatgacc   1566

aagctgctcc agaattagtc actcaaaatc tctcagatta aattatcaac tgtcaccaac   1626

cattcctatg ctgacaaggc aattgcttgt tctctgtgtt cctgatacta caaggctctt   1686

cctgacttcc taaagatgca ttataaaaat cttataattc acatttctcc ctaaactttg   1746

actcaatcat ggtatgttgg caaatatggt atattactat tcaaattgtt ttccttgtac   1806

ccatatgtaa tgggtcttgt gaatgtgctc ttttgttcct ttaatcataa taaaaacatg   1866

tttaagc                                                              1873


<210> SEQ ID NO 16
<211> LENGTH: 386
<212> TYPE: PRT
<213> ORGANISM: Gallus gallus

<400> SEQUENCE: 16

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160
```

-continued

```
Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385
```